(12) United States Patent
Chen et al.

(10) Patent No.: US 10,231,957 B2
(45) Date of Patent: *Mar. 19, 2019

(54) HISTONE DEMETHYLASE INHIBITORS

(71) Applicant: CELGENE QUANTICEL RESEARCH, INC., San Diego, CA (US)

(72) Inventors: Young K. Chen, San Marcos, CA (US); Michael Brennan Wallace, San Diego, CA (US)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,316

(22) Filed: Jun. 1, 2018

(65) Prior Publication Data

US 2018/0271843 A1  Sep. 27, 2018

Related U.S. Application Data

(63) Continuation of application No. 15/667,553, filed on Aug. 2, 2017, now Pat. No. 10,016,401, which is a continuation of application No. 14/852,860, filed on Sep. 14, 2015, now Pat. No. 9,758,517.

(60) Provisional application No. 62/051,850, filed on Sep. 17, 2014.

(51) Int. Cl.
| | |
|---|---|
| *C07D 471/04* | (2006.01) |
| *A61K 31/437* | (2006.01) |
| *C07D 487/04* | (2006.01) |
| *A61P 35/00* | (2006.01) |

(52) U.S. Cl.
CPC .......... *A61K 31/437* (2013.01); *A61P 35/00* (2018.01); *C07D 471/04* (2013.01); *C07D 487/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 6,232,320 B1 | 5/2001 | Stewart et al. | |
| 7,371,862 B2 | 5/2008 | Vanotti et al. | |
| 8,093,220 B2 | 1/2012 | Atadja | |
| 9,738,637 B2 | 8/2017 | Chen et al. | |
| 9,758,517 B2 * | 9/2017 | Chen | C07D 471/04 |
| 9,873,697 B2 | 1/2018 | Chen et al. | |
| 2007/0098816 A1 | 5/2007 | Nakanishi et al. | |
| 2008/0045561 A1 | 2/2008 | Nemecek et al. | |
| 2013/0053383 A1 | 2/2013 | Duquenne et al. | |
| 2014/0171432 A1 | 6/2014 | Kanouni et al. | |
| 2017/0326116 A1 * | 11/2017 | Chen | C07D 471/04 |

FOREIGN PATENT DOCUMENTS

| | | |
|---|---|---|
| JP | 2012107001 A | 6/2012 |
| WO | 01/02369 A2 | 1/2001 |
| WO | 2004/082638 A2 | 9/2004 |
| WO | 2007/056281 A2 | 5/2007 |
| WO | 2008/135786 A1 | 11/2008 |
| WO | 2013/028999 A1 | 2/2013 |
| WO | 2014/053491 A1 | 4/2014 |
| WO | 2014/164708 A1 | 10/2014 |

OTHER PUBLICATIONS

Berge et al., "Pharmaceutical Salts," Journal of Pharmaceutical Sciences, 66(1):1-19 (Jan. 1977).
Bundgard et al., Design of Prodrugs, pp. 7-9, 21-24 (1985)., front page and copyright page only.
Cheung et al., "Efficient and regioselective synthesis of 2-alkyl-2H-indazoles," J. Org Chem. 68(10):4093-4095 (May 2003).
Extended European Search Report, dated Feb. 7, 2018, issued in related European Application No. 15842582.7, filed Sep. 14, 2015.
Golub et al., "Molecular classification of cancer: class discovery and class prediction by gene expression monitoring," Science, 286(5439):531-7 (Oct. 1999).
Higuchi et al., Pro-drugs as Novel Delivery Systems, A.C.S. Symposium Series, vol. 14 (1975).
International Preliminary Report on Patentability dated Sep. 24, 2015, in International Application No. PCT/US2014/23273, filed Mar. 11, 2014.
International Preliminary Report on Patentability dated Mar. 30, 2017, in related International Patent Application No. PCT/US2015/049926, filed Sep. 14, 2015.
International Search Report and Written Opinion dated Jun. 18, 2014, in International Application No. PCT/US2014/23273, filed Mar. 11, 2014.
International Search Report and Written Opinion dated Dec. 4, 2015, in International Application No. PCT/US2015/049926, filed Sep. 14, 2015.
Lachner et al., "An epigenetic road map for histone lysine methylation," Journal of Cell Science, 116:2117-2124 (Jun. 1, 2003).
Lin et al., "Loss of the retinoblastoma binding protein 2 (RBP2) histone demethylase suppresses tumorigenesis in mice lacking RB1 or Men1," PNAS 108(33):13379-13386 (2011).
Margueron et al., "The key to development: interpreting the histone code?," Current Opinion in Genetics & Development, 15:163-176 (2005).
McLaughlin et al., "Efficient Access to Azaindoles and Indoles," Org. Lett. 8(15):3307-3310 (2006).

(Continued)

*Primary Examiner* — Laura L Stockton
(74) *Attorney, Agent, or Firm* — Wiley Rein LLP

(57) ABSTRACT

The present invention relates generally to compositions and methods for treating cancer and neoplastic disease. Provided herein are substituted pyrrolopyridine derivative compounds and pharmaceutical compositions comprising said compounds. The subject compounds and compositions are useful for inhibition of histone demethylase. Furthermore, the subject compounds and compositions are useful for the treatment of cancer, such as prostate cancer, breast cancer, bladder cancer, lung cancer and/or melanoma and the like.

4 Claims, No Drawings

(56) References Cited

OTHER PUBLICATIONS

Nazare et al., "Flexible, Palladium-Catalyzed Indole and Azaindole Synthesis by Direct Annulation of Chloroanilines and Chloroaminopyridines with Ketones," Angew. Chem. Int. ed. Engl. 43(34):4526-4528 (2004).
Search Report and Written Opinion, dated Nov. 22, 2017, issued in related Singapore Application No. 11201702119P, filed Sep. 14, 2015.
Sonogashira et al., A convenient synthesis of acetylenes: catalytic substitutions of acetylenic hydrogen with bromoalkenes, iodoarenes and bromopyridines. Tetrahedron Lett. 16(50):4467-4470 (1975).
Stahl et al., "Handbook of Pharmaceutical Salts," Verlag Helvetica Chimica Acta, Zurich (2002), Table of Contents only.

* cited by examiner

HISTONE DEMETHYLASE INHIBITORS

RELATED APPLICATIONS

This application is a continuation of U.S. patent application Ser. No. 15/667,553, filed Aug. 2, 2017, which is a continuation of U.S. patent application Ser. No. 14/852,860, filed Sep. 14, 2015, now U.S. Pat. No. 9,758,517, which claims priority benefit of U.S. Provisional Application No. 62/051,850, filed Sep. 17, 2014, the contents of which are hereby incorporated by reference in their entireties for all purposes.

BACKGROUND

A need exists in the art for an effective treatment of cancer and neoplastic disease.

BRIEF SUMMARY OF THE INVENTION

Provided herein are substituted pyrrolopyridine derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like. The substituted pyrrolopyridine derivative compounds described herein are based upon a disubstituted pyrrolo[3,2-b]pyridine ring system bearing at the 7-position a carboxylic acid or bioisostere thereof, and a second substituent at the 2-position. The 2-position substituent, in various embodiments, is selected from a bicyclic heteroaryl group.

One embodiment provides a compound having the structure of Formula (I),

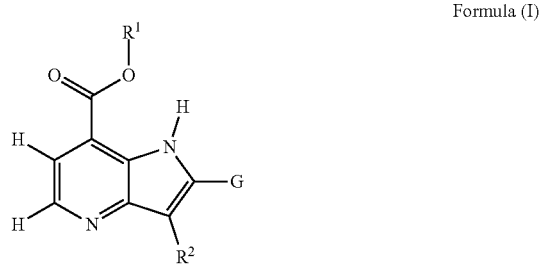

Formula (I)

or a pharmaceutically acceptable salt thereof,
wherein,
$R^1$ is hydrogen or alkyl;
$R^2$ is hydrogen, halogen or alkyl;
G is

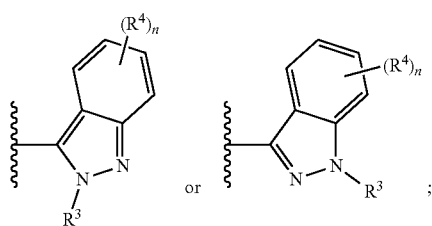

n is 0, 1, or 2;
$R^3$ is alkyl, carbocyclyl, carbocyclylalkyl, heterocyclyl, or heterocyclylalkyl;
$R^4$ is halogen, alkyl, alkoxy, carbocyclyl, heterocyclyl, aryl, heteroaryl, or X—$R^5$;
wherein:
X is —($C_1$-$C_6$)alkylene-, —O—, —S—, or —$NR^1$—; and
$R^5$ is carbocyclyl, heterocyclyl, aryl, or heteroaryl.

One embodiment provides a pharmaceutical composition comprising a compound of Formula (I), or a pharmaceutically acceptable salt thereof, and at least one pharmaceutically acceptable excipient.

One embodiment provides a method for inhibiting a histone demethylase enzyme comprising contacting the histone demethylase enzyme with a compound of Formula (I).

One embodiment provides a method for treating cancer in subject in need thereof comprising administering to the subject a composition comprising a compound of Formula (I) or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$), —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$NR$^a$ (where t is 1 or 2) and —S(O)$_t$N(R$^a$)2 (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—R—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—R—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

1 "Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydro-pyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^3$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$), —$R^b$—O—$R^c$—C(O)N($R^a$)$_2$, —$R^b$—N($R^3$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2-, 3-, or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo-[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocyclo-octa[d]pyrimidinyl, 5,6,7,8,9,10-hexahydrocycloocta[d]pyridazinyl, 5,6,7,8,9,10-hexahydro-cycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]-pyrimidinyl, 6,7,8,9-tetrahydro-5H-cyclohepta[4,5]thieno[2,3-d]pyrimidinyl, 5,6,7,8-tetrahydro-pyrido[4,5-c]pyridazinyl, thiazolyl, thiadiazolyl, triazolyl, tetrazolyl, triazinyl, thieno[2,3-d]-pyrimidinyl, thieno[3,2-d]pyrimidinyl, thieno[2,3-c]pyridinyl, and thiophenyl (i.e., thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)v$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and R is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to, and the like.

The compounds disclosed herein may contain one or more asymmetric centers and may thus give rise to enantiomers, diastereomers, and other stereoisomeric forms that may be defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans).

Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

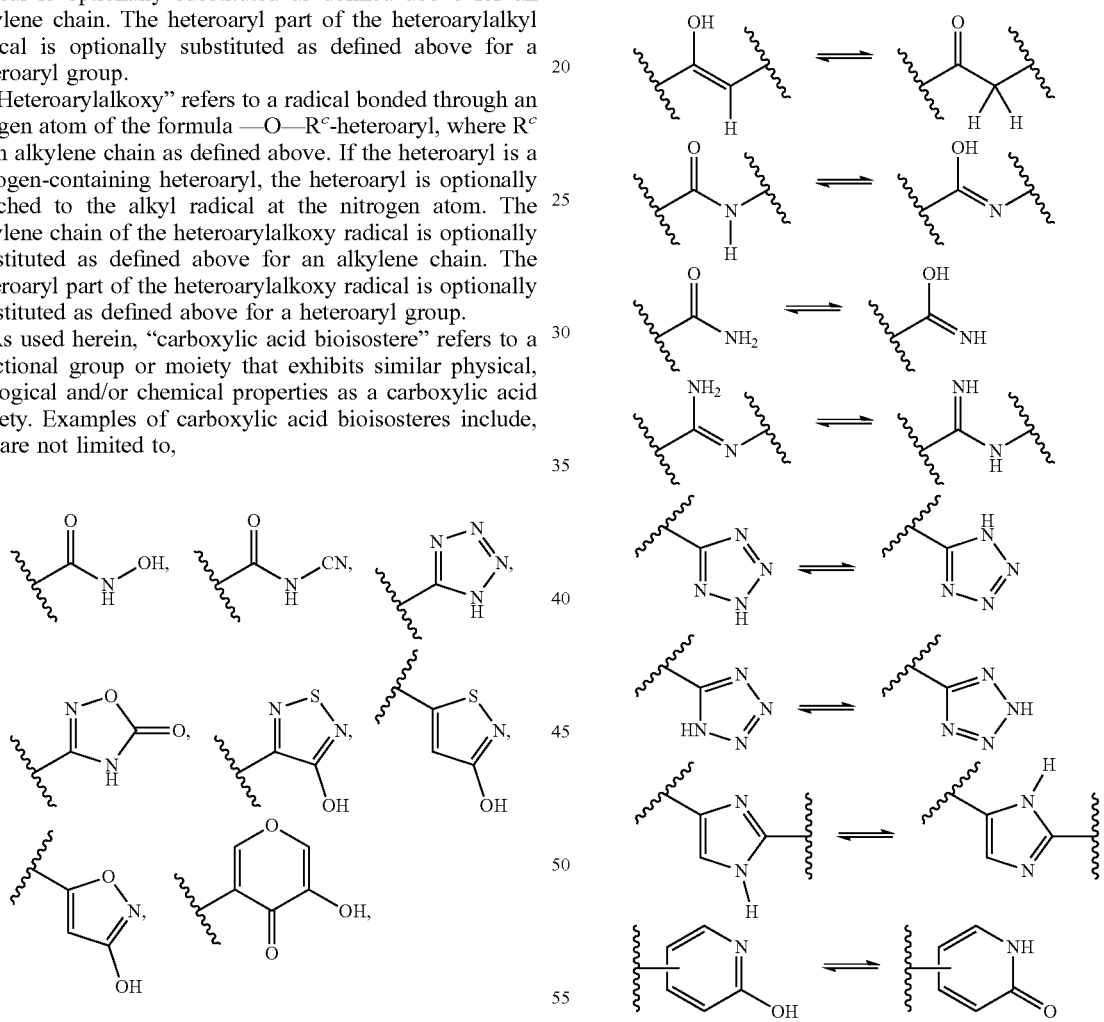

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted pyrrolopyridine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, e.g., Berge S. M. et al., *Pharmaceutical Salts*, J. Pharm. Sci. 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., DESIGN OF PRODRUGS (1985), pp. 7-9, 21-24 (Elsevier, Amsterdam).

A discussion of prodrugs is provided in Higuchi, T. et al., *Pro-drugs as Novel Delivery Systems*, A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo, when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like. In some embodiments, the substituted pyrrolopyridine derivative compounds described herein are obtained by the in vivo oxidation of an aldehyde prodrug, or aldehyde-equivalent prodrug precursor. As illustrated below, the aldehyde-equivalent prodrug precursor is transformed in vivo into an aldehyde prodrug. In vivo oxidation of the aldehyde prodrug affords the substituted pyrrolopyridine derivative compounds described herein. The aldehyde-equivalent prodrug precursor is an aldehyde derivate such as imine, hydrazone, oxime, or the like.

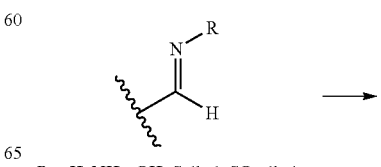

R = H, NH$_2$, OH, Salkyl, SO$_2$alkyl

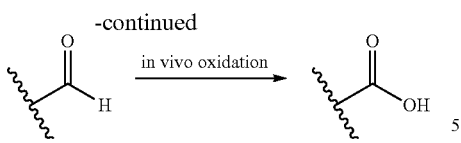

Substituted Pyrrolopyridine Derivative Compounds

Substituted pyrrolopyridine derivative compounds are described herein that inhibit a histone demethylase enzyme. These compounds, and compositions comprising these compounds, are useful for the treatment of cancer and neoplastic disease. The compounds described herein may, therefore, be useful for treating prostate cancer, breast cancer, bladder cancer, lung cancer and/or melanoma and the like.

One embodiment provides a compound having the structure of Formula (I),

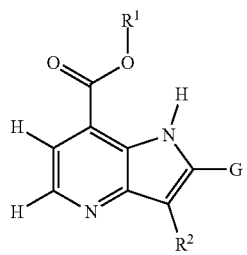

Formula (I)

or a pharmaceutically acceptable salt thereof,
wherein,
$R^1$ is hydrogen or alkyl;
$R^2$ is hydrogen, halogen or alkyl;
G is

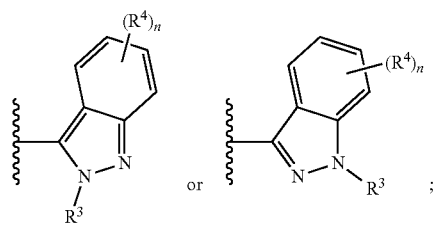

n is 0, 1, or 2;
$R^3$ is alkyl, carbocyclyl, carbocyclylalkyl, heterocyclyl, or heterocyclylalkyl;
$R^4$ is halogen, alkyl, alkoxy, carbocyclyl, heterocyclyl, aryl, heteroaryl, or X—$R^5$;
wherein:
X is —($C_1$-$C_6$)alkylene-, —O—, —S—, or —$NR^1$—; and
$R^5$ is carbocyclyl, heterocyclyl, aryl, or heteroaryl.

Another embodiment provides the compound of Formula (I), or a pharmaceutically acceptable salt thereof, wherein $R^1$ is hydrogen. Another embodiment provides the compound of Formula (I), or a pharmaceutically acceptable salt thereof, wherein $R^1$ is alkyl. Another embodiment provides the compound of Formula (I), or a pharmaceutically acceptable salt thereof, wherein $R^1$ is methyl.

Another embodiment provides the compound of Formula (I), or a pharmaceutically acceptable salt thereof, wherein $R^2$ is hydrogen.

Another embodiment provides the compound of Formula (I), or a pharmaceutically acceptable salt thereof, wherein the compound of Formula (I) is of Formula (Ia):

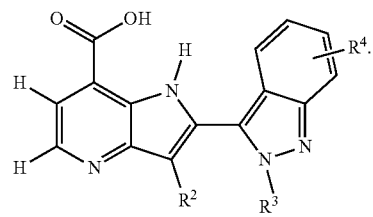

Formula (Ia)

Another embodiment provides the compound of Formula (I), or a pharmaceutically acceptable salt thereof, wherein the compound of Formula (I) is of Formula (Ib):

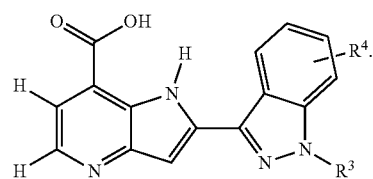

Formula (Ib)

Another embodiment provides the compound of Formula (I), or a pharmaceutically acceptable salt thereof, wherein $R^3$ is alkyl. Another embodiment provides the compound of Formula (I), or a pharmaceutically acceptable salt thereof, wherein $R^3$ is methyl. Another embodiment provides the compound of Formula (I), or a pharmaceutically acceptable salt thereof, wherein $R^3$ is alkyl substituted with at least one halogen.

Another embodiment provides the compound of Formula (I), or a pharmaceutically acceptable salt thereof, wherein $R^3$ is carbocyclylalkyl or heterocyclylalkyl. Another embodiment provides the compound of Formula (I), or a pharmaceutically acceptable salt thereof, wherein $R^3$ is elected from a group consisting of:

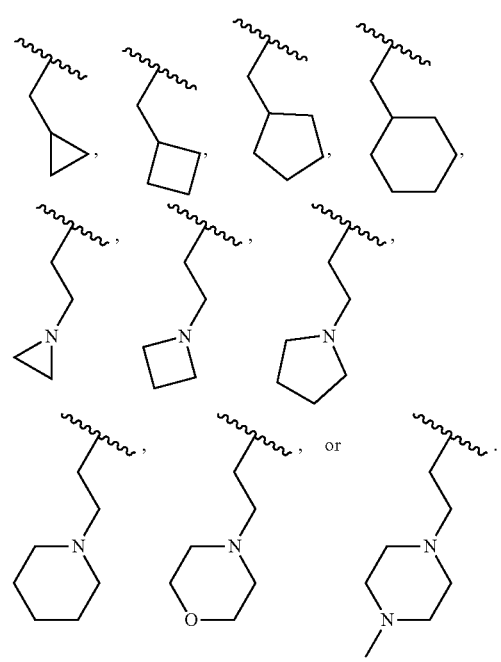

Another embodiment provides the compound of Formula (I), or a pharmaceutically acceptable salt thereof, wherein $R^4$ is halogen. Another embodiment provides the compound of Formula (I), or a pharmaceutically acceptable salt thereof, wherein $R^4$ is chloro or fluoro. Another embodiment provides the compound of Formula (I), or a pharmaceutically acceptable salt thereof, wherein $R^4$ is alkyl substituted with at least one halogen. Another embodiment provides the compound of Formula (I), or a pharmaceutically acceptable salt thereof, wherein $R^4$ is —$CF_3$.

Another embodiment provides the compound of Formula (I), or a pharmaceutically acceptable salt thereof, wherein $R^4$ is alkoxy. Another embodiment provides the compound of Formula (I), or a pharmaceutically acceptable salt thereof, wherein $R^4$ is methoxy. Another embodiment provides the compound of Formula (I), or a pharmaceutically acceptable salt thereof, wherein $R_4$ is alkoxy substituted with at least one halogen. Another embodiment provides the compound of Formula (I), or a pharmaceutically acceptable salt thereof, wherein $R^4$ is —$OCF_3$.

Another embodiment provides the compound of Formula (I), or a pharmaceutically acceptable salt thereof, wherein $R^4$ is carbocyclyl.

Another embodiment provides the compound of Formula (I), or a pharmaceutically acceptable salt thereof, wherein $R^4$ is heterocyclyl. Another embodiment provides the compound of Formula (I), or a pharmaceutically acceptable salt thereof, wherein the heterocyclyl is selected from a group consisting of:

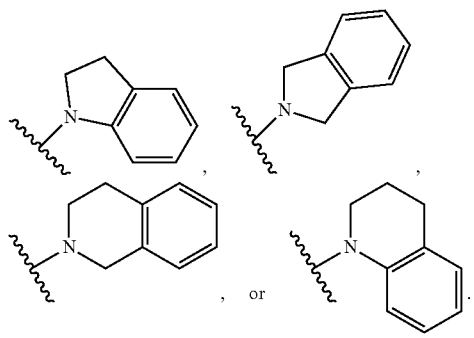

Another embodiment provides the compound of Formula (I), or a pharmaceutically acceptable salt thereof, wherein $R^4$ is X—$R^5$. Another embodiment provides the compound of Formula (I), or a pharmaceutically acceptable salt thereof, wherein X is —O—. Another embodiment provides the compound of Formula (I), or a pharmaceutically acceptable salt thereof, wherein X is —S—. Another embodiment provides the compound of Formula (I), or a pharmaceutically acceptable salt thereof, wherein X is —$NR^1$—; and $R^1$ is methyl.

Another embodiment provides the compound of Formula (I), or a pharmaceutically acceptable salt thereof, wherein $R^5$ is aryl. Another embodiment provides the compound of Formula (I), or a pharmaceutically acceptable salt thereof, wherein the aryl is phenyl optionally substituted with halogen, —CN, alkyl, alkynyl, alkoxy, or carbocycle. Another embodiment provides the compound of Formula (I), or a pharmaceutically acceptable salt thereof, wherein $R^5$ is heteroaryl. Another embodiment provides the compound of Formula (I), or a pharmaceutically acceptable salt thereof, wherein the heteroaryl is pyridinyl optionally substituted with halogen, —CN, alkyl, alkynyl, alkoxy, or carbocycle.

One embodiment provides a compound having the structure of Formula (II),

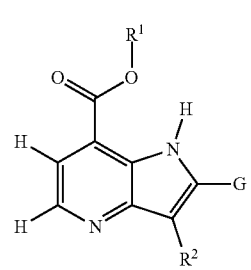

Formula (II)

or a pharmaceutically acceptable salt thereof, wherein, $R^1$ is hydrogen or alkyl;

$R^2$ is hydrogen, halogen or alkyl;

G is

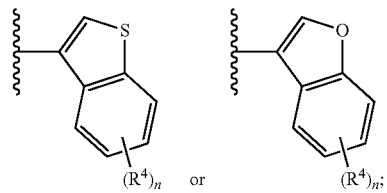

n is 0, 1, or 2;

$R^4$ is halogen, alkyl, alkoxy, carbocyclyl, heterocyclyl, aryl, heteroaryl, or X—$R^5$;

wherein: X is —($C_1$-$C_6$)alkylene-, —O—, —S—, or —$NR^1$—; and $R^5$ is carbocyclyl, heterocyclyl, aryl, or heteroaryl.

Another embodiment provides the compound of Formula (II), or a pharmaceutically acceptable salt thereof, wherein G is

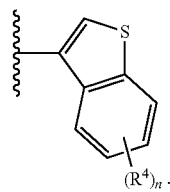

Another embodiment provides the compound of Formula (II), or a pharmaceutically acceptable salt thereof, wherein G is

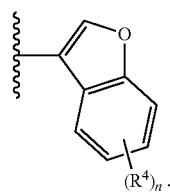

Another embodiment provides the compound of Formula (II), or a pharmaceutically acceptable salt thereof, wherein G is

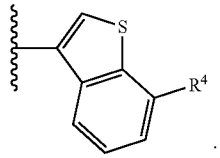

Another embodiment provides the compound of Formula (II), or a pharmaceutically acceptable salt thereof, wherein G is

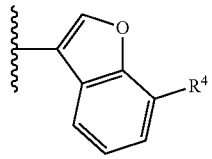

Another embodiment provides the compound of Formula (II), or a pharmaceutically acceptable salt thereof, wherein $R^4$ is aryl. Another embodiment provides the compound of Formula (II), or a pharmaceutically acceptable salt thereof, wherein $R^4$ is $X—R^5$. Another embodiment provides the compound of Formula (II), or a pharmaceutically acceptable salt thereof, wherein $R^4$ is $X—R^5$; X is $—NR^1—$; and $R^5$ is aryl.

In some embodiments, the compound of Formula (I) as disclosed herein has the structure provided in Table 1.

TABLE 1

| Chemical Synthesis Example | Structure | Name |
|---|---|---|
| 1 | 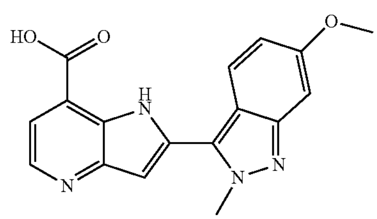 [SMILES: COc1ccc2c(-c3cc4nccc(C(=O)O)c4[nH]3)n(C)nc2c1] | 2-(6-methoxy-2-methyl-2H-indazol-3-yl)-1H-pyrrolo[3,2-b]pyridine-7-carboxylic acid |
| 2 | 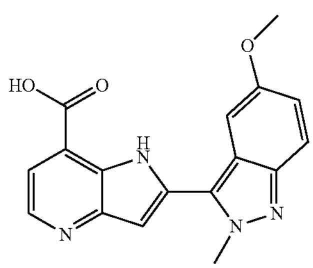 [SMILES: COc1ccc2nn(C)c(-c3cc4nccc(C(=O)O)c4[nH]3)c2c1] | 2-(5-methoxy-2-methyl-2H-indazol-3-yl)-1H-pyrrolo[3,2-b]pyridine-7-carboxylic acid |
| 3 | 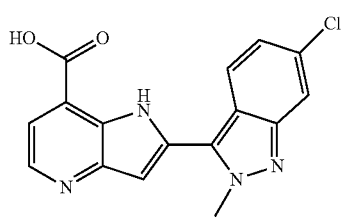 [SMILES: Cn1nc2cc(Cl)ccc2c1-c1cc2nccc(C(=O)O)c2[nH]1] | 2-(6-chloro-2-methyl-2H-indazol-3-yl)-1H-pyrrolo[3,2-b]pyridine-7-carboxylic acid |
| 4 | 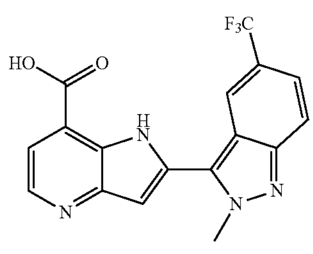 [SMILES: Cn1nc2ccc(C(F)(F)F)cc2c1-c1cc2nccc(C(=O)O)c2[nH]1] | 2-[2-methyl-5-(trifluoromethyl)-2H-indazol-3-yl]-1H-pyrrolo[3,2-b]pyridine-7-carboxylic acid |

TABLE 1-continued

| Chemical Synthesis Example | Structure | Name |
|---|---|---|
| 5 | 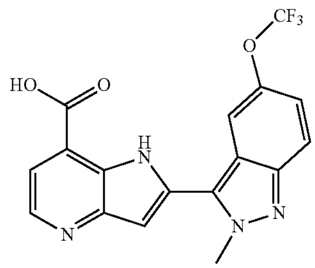 [SMILES: Cn1nc2ccc(OC(F)(F)F)cc2c1-c1cc2nccc(C(=O)O)c2[nH]1] | 2-[2-methyl-5-(trifluoromethoxy)-2H-indazol-3-yl]-H-pyrrolo[3,2-b]pyridine-7-carboxylic acid |
| 6 | 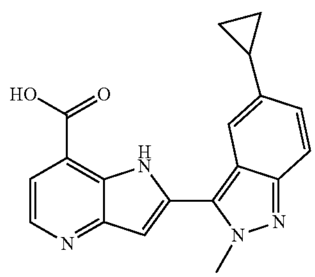 [SMILES: Cn1nc2ccc(C3CC3)cc2c1-c1cc2nccc(C(=O)O)c2[nH]1] | 2-(5-cyclopropyl-2-methyl-2H-indazol-3-yl)-1H-pyrrolo[3,2-b]pyridine-7-carboxylic acid |
| 7 | 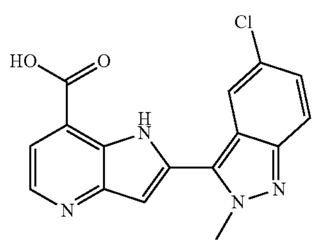 | 2-(5-chloro-2-methyl-2H-indazol-3-yl)-1H-pyrrolo[3,2-b]pyridine-7-carboxylic acid |
| 8 | 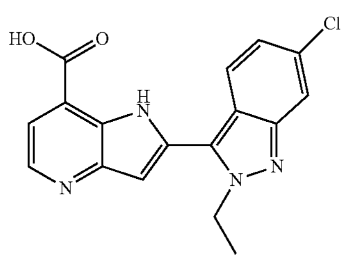 [SMILES: CCn1nc2cc(Cl)ccc2c1-c1cc2nccc(C(=O)O)c2[nH]1] | 2-(6-chloro-2-ethyl-2H-indazol-3-yl)-1H-pyrrolo[3,2-b]pyridine-7-carboxylic acid |
| 9 | 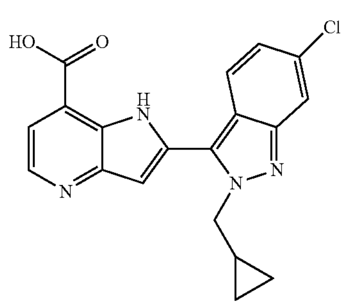 [SMILES: O=C(O)c1ccnc2cc(-c3c4ccc(Cl)cc4nn3CC3CC3)[nH]c12] | 2-[6-chloro-2-(cyclopropylmethyl)-2H-indazol-3-yl]-1H-pyrrolo[3,2-b]pyridine-7-carboxylic acid |

TABLE 1-continued

| Chemical Synthesis Example | Structure | Name |
|---|---|---|
| 10 | 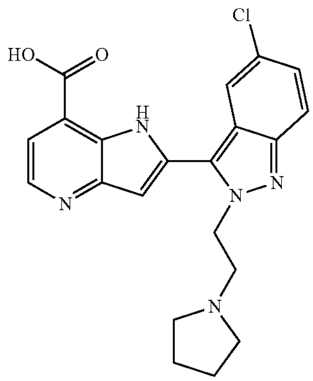 [SMILES: O=C(O)c1ccnc2cc(-c3c4cc(Cl)ccc4nn3CCN3CCCC3)[nH]c12] | 2-{5-chloro-2-[2-(pyrrolidin-1-yl)ethyl]-2H-indazol-3-yl}-1H-pyrrolo[3,2-b]pyridine-7-carboxylic acid |
| 11 | 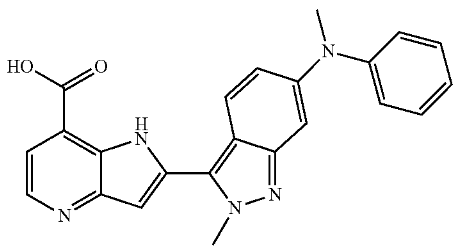 [SMILES: CN(c1ccccc1)c1ccc2c(-c3cc4nccc(C(=O)O)c4[nH]3)n(C)nc2c1] | 2-{2-methyl-6-[methyl(phenyl)amino]-2H-indazol-3-yl}-1H-pyrrolo[3,2-b]pyridine-7-carboxylic acid |
| 12 | 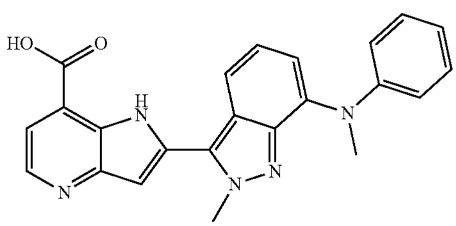 [SMILES: CN(c1ccccc1)c1cccc2c(-c3cc4nccc(C(=O)O)c4[nH]3)n(C)nc12] | 2-{2-methyl-7-[methyl(phenyl)amino]-2H-indazol-3-yl}-1H-pyrrolo[3,2-b]pyridine-7-carboxylic acid |
| 13 | 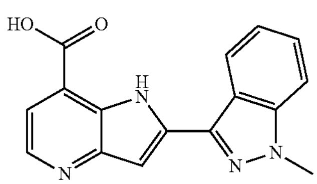 [SMILES: Cn1nc(-c2cc3nccc(C(=O)O)c3[nH]2)c2ccccc21] | 2-(1-methyl-1H-indazol-3-yl)-1H-pyrrolo[3,2-b]pyridine-7-carboxylic acid |
| 14 | 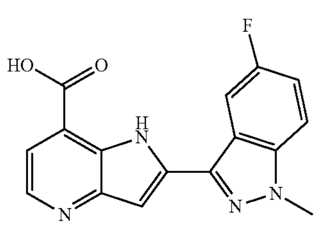 [SMILES: Cn1nc(-c2cc3nccc(C(=O)O)c3[nH]2)c2cc(F)ccc21] | 2-(5-fluoro-1-methyl-1H-indazol-3-yl)-1H-pyrrolo[3,2-b]pyridine-7-carboxylic acid |
| 15 | 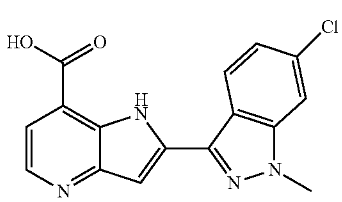 [SMILES: Cn1nc(-c2cc3nccc(C(=O)O)c3[nH]2)c2ccc(Cl)cc21] | 2-(6-chloro-1-methyl-1H-indazol-3-yl)-1H-pyrrolo[3,2-b]pyridine-7-carboxylic acid |

TABLE 1-continued

| Chemical Synthesis Example | Structure | Name |
|---|---|---|
| 16 | 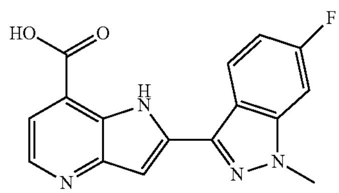 [SMILES: Cn1nc(-c2cc3nccc(C(=O)O)c3[nH]2)c2ccc(F)cc21] | 2-(6-fluoro-1-methyl-1H-indazol-3-yl)-1H-pyrrolo[3,2-b]pyridine-7-carboxylic acid |
| 17 | 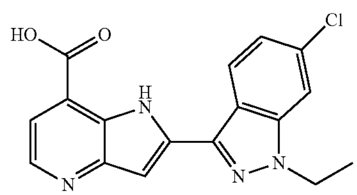 [SMILES: CCn1nc(-c2cc3nccc(C(=O)O)c3[nH]2)c2ccc(Cl)cc21] | 2-(6-chloro-1-ethyl-1H-indazol-3-yl)-1H-pyrrolo[3,2-b]pyridine-7-carboxylic acid |
| 18 | 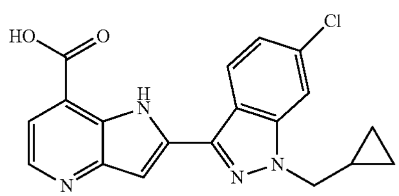 [SMILES: O=C(O)c1ccnc2cc(-c3nn(CC4CC4)c4cc(Cl)ccc34)[nH]c12] | 2-[6-chloro-1-(cyclopropylmethyl)-1H-indazol-3-yl]-1H-pyrrolo[3,2-b]pyridine-7-carboxylic acid |
| 19 | 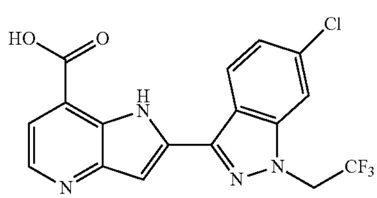 [SMILES: O=C(O)c1ccnc2cc(-c3nn(CC(F)(F)F)c4cc(Cl)ccc34)[nH]c12] | 2-[6-chloro-1-(2,2,2-trifluoroethyl)-1H-indazol-3-yl]-1H-pyrrolo[3,2-b]pyridine-7-carboxylic acid |
| 20 | 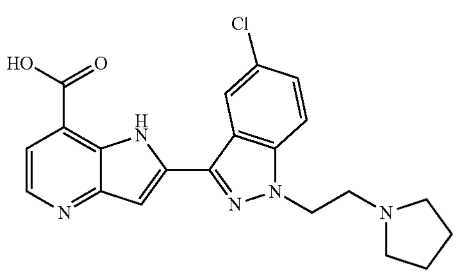 [SMILES: O=C(O)c1ccnc2cc(-c3nn(CCN4CCCC4)c4ccc(Cl)cc34)[nH]c12] | 2-{5-chloro-1-[2-(pyrrolidin-1-yl)ethyl]-1H-indazol-3-yl}-1H-pyrrolo[3,2-b]pyridine-7-carboxylic acid |
| 21 | 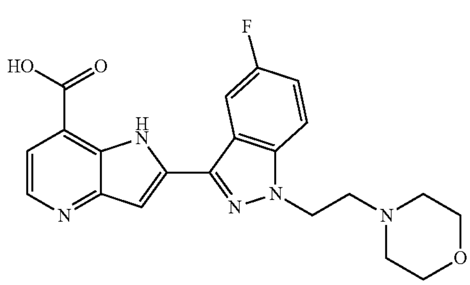 [SMILES: O=C(O)c1ccnc2cc(-c3nn(CCN4CCOCC4)c4ccc(F)cc34)[nH]c12] | 2-{5-fluoro-1-[2-(morpholin-4-yl)ethyl]-1H-indazol-3-yl}-1H-pyrrolo[3,2-b]pyridine-7-carboxylic acid |

In additional embodiments, the compound of Formula (I) is selected from a compound provided in Table 2.
TABLE 2
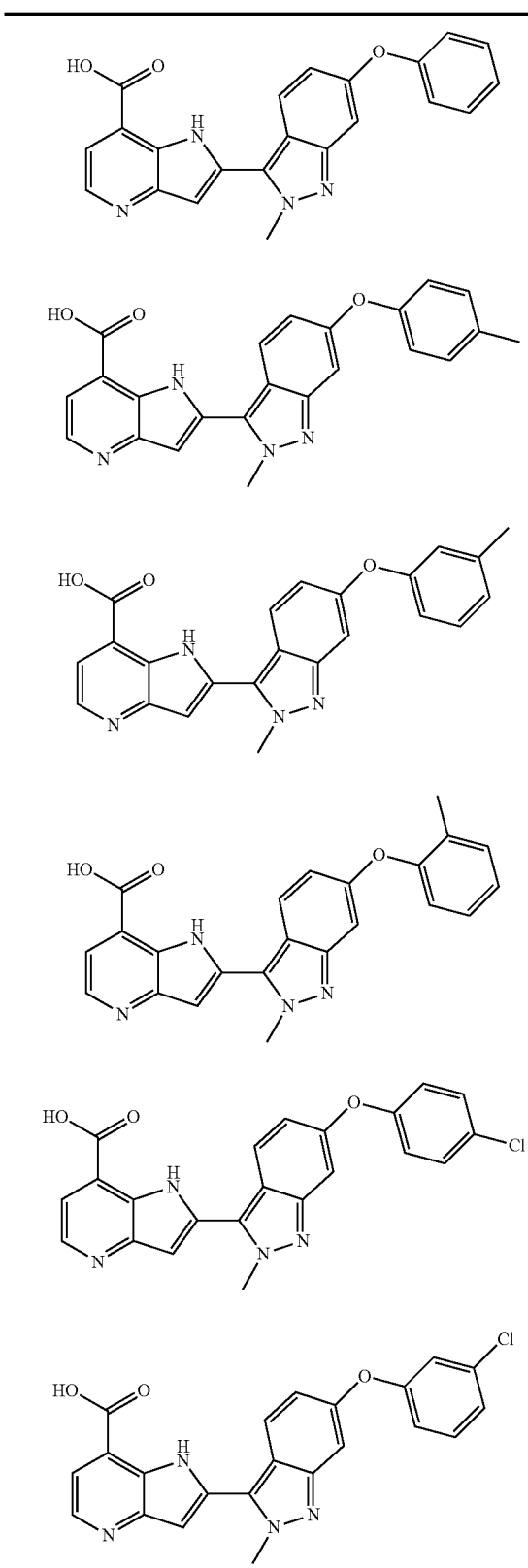
TABLE 2-continued
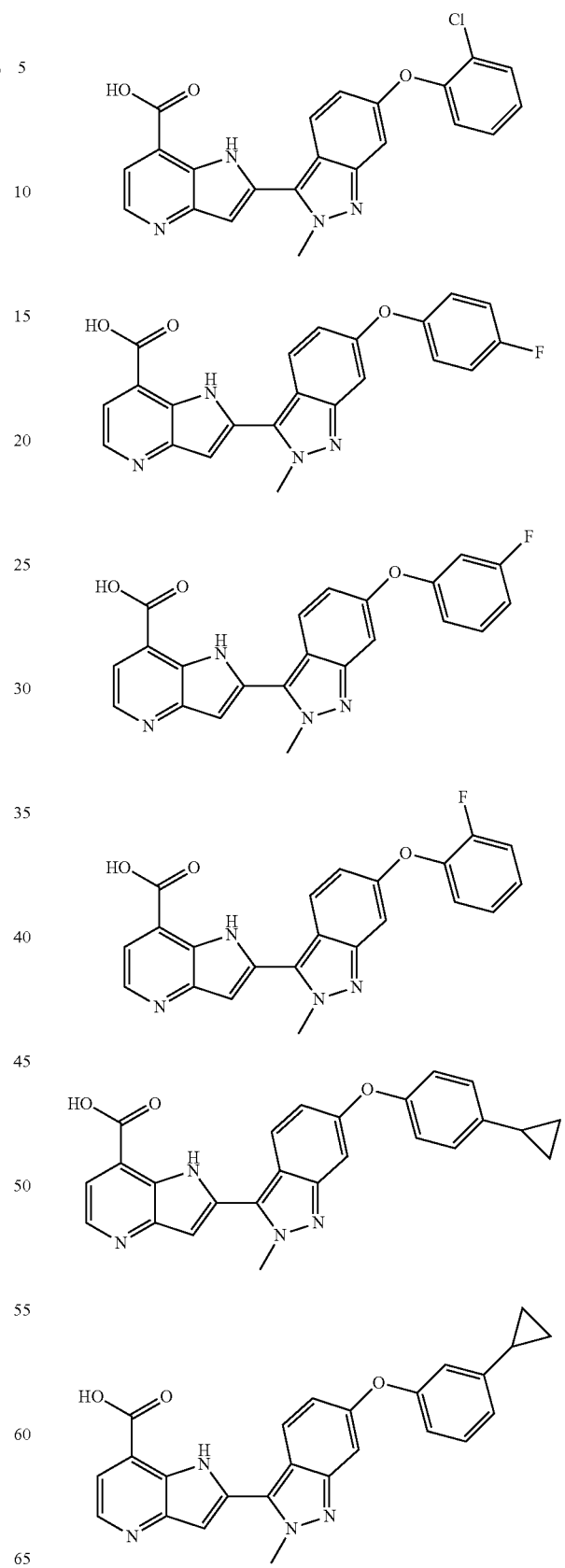

TABLE 2-continued
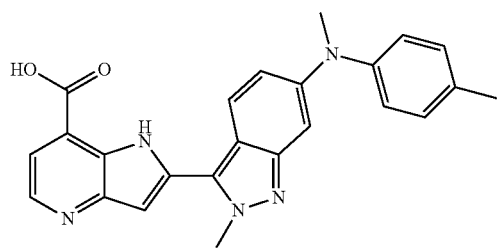 [SMILES: Cc1ccc(N(C)c2ccc3c(-c4cc5nccc(C(=O)O)c5[nH]4)n(C)nc3c2)cc1]
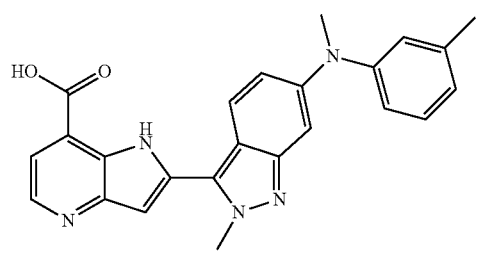 [SMILES: Cc1cccc(N(C)c2ccc3c(-c4cc5nccc(C(=O)O)c5[nH]4)n(C)nc3c2)c1]
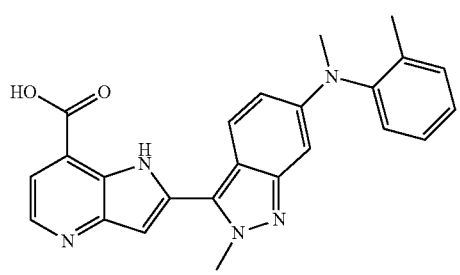 [SMILES: Cc1ccccc1N(C)c1ccc2c(-c3cc4nccc(C(=O)O)c4[nH]3)n(C)nc2c1]
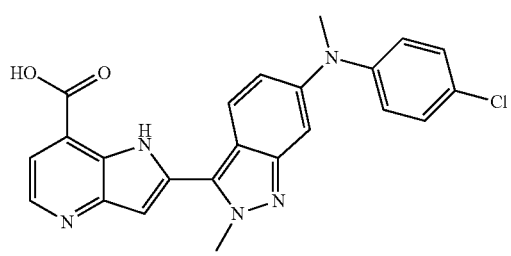 [SMILES: CN(c1ccc(Cl)cc1)c1ccc2c(-c3cc4nccc(C(=O)O)c4[nH]3)n(C)nc2c1]
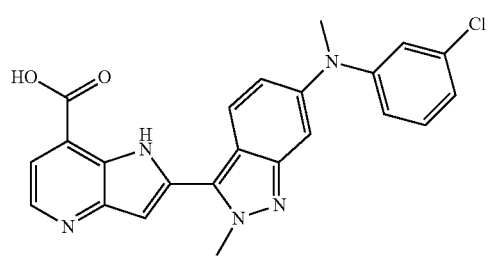 [SMILES: CN(c1cccc(Cl)c1)c1ccc2c(-c3cc4nccc(C(=O)O)c4[nH]3)n(C)nc2c1]
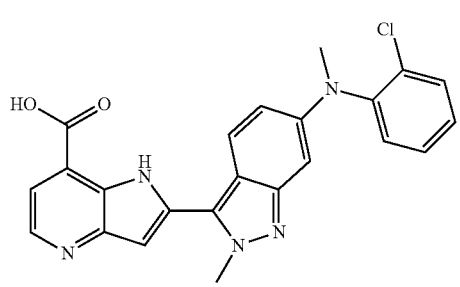 [SMILES: CN(c1ccc2c(-c3cc4nccc(C(=O)O)c4[nH]3)n(C)nc2c1)c1ccccc1Cl]
TABLE 2-continued
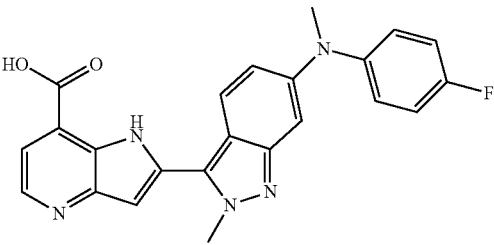 [SMILES: CN(c1ccc(F)cc1)c1ccc2c(-c3cc4nccc(C(=O)O)c4[nH]3)n(C)nc2c1]
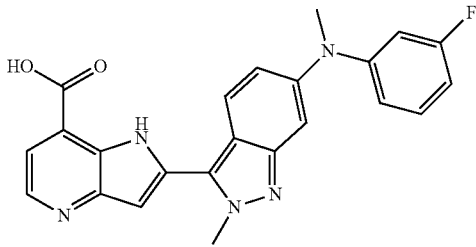 [SMILES: CN(c1cccc(F)c1)c1ccc2c(-c3cc4nccc(C(=O)O)c4[nH]3)n(C)nc2c1]
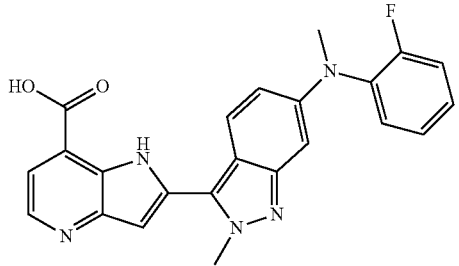 [SMILES: CN(c1ccc2c(-c3cc4nccc(C(=O)O)c4[nH]3)n(C)nc2c1)c1ccccc1F]
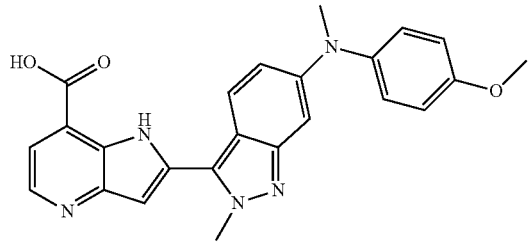 [SMILES: COc1ccc(N(C)c2ccc3c(-c4cc5nccc(C(=O)O)c5[nH]4)n(C)nc3c2)cc1]
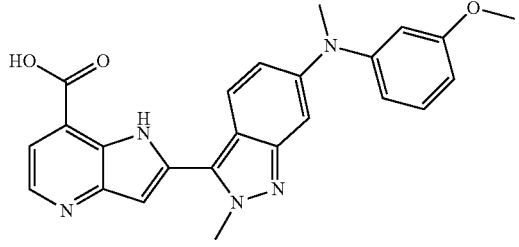 [SMILES: COc1cccc(N(C)c2ccc3c(-c4cc5nccc(C(=O)O)c5[nH]4)n(C)nc3c2)c1]
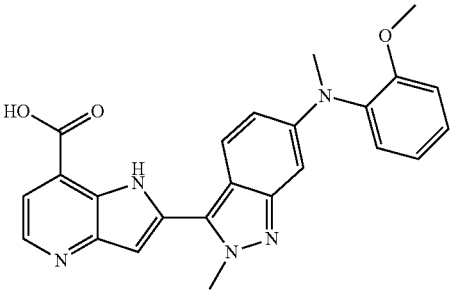 [SMILES: COc1ccccc1N(C)c1ccc2c(-c3cc4nccc(C(=O)O)c4[nH]3)n(C)nc2c1]

TABLE 2-continued
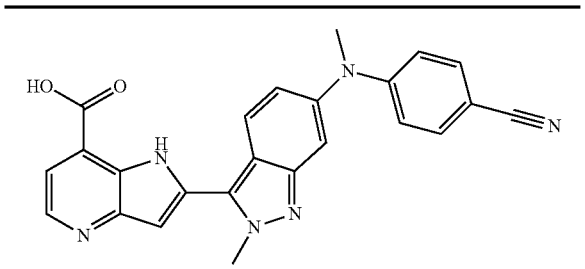
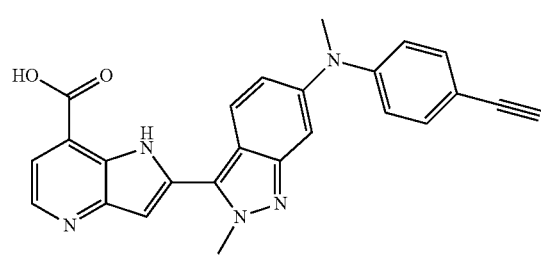 [SMILES: C#Cc1ccc(N(C)c2ccc3c(-c4cc5nccc(C(=O)O)c5[nH]4)n(C)nc3c2)cc1]
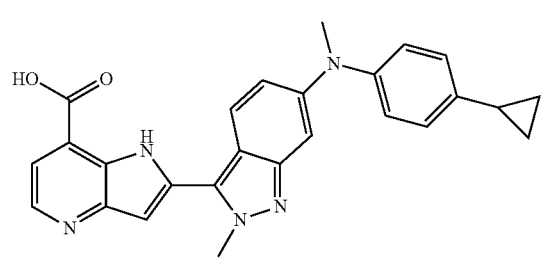 [SMILES: CN(c1ccc(C2CC2)cc1)c1ccc2c(-c3cc4nccc(C(=O)O)c4[nH]3)n(C)nc2c1]
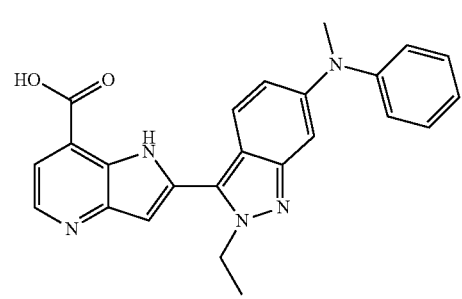 [SMILES: CCn1nc2cc(N(C)c3ccccc3)ccc2c1-c1cc2nccc(C(=O)O)c2[nH]1]
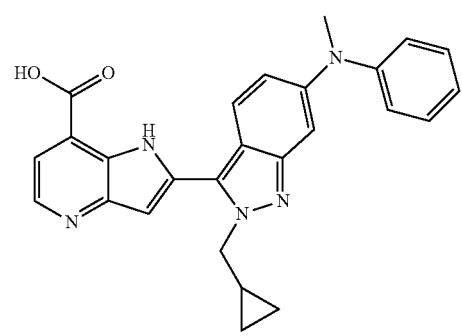 [SMILES: CN(c1ccccc1)c1ccc2c(-c3cc4nccc(C(=O)O)c4[nH]3)n(CC3CC3)nc2c1]
TABLE 2-continued
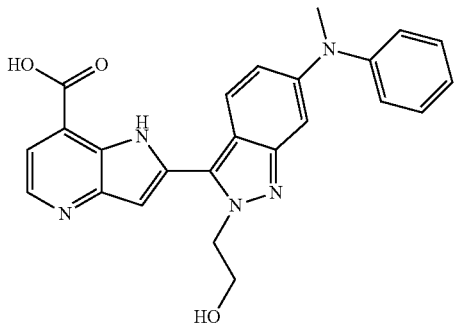 [SMILES: CN(c1ccccc1)c1ccc2c(-c3cc4nccc(C(=O)O)c4[nH]3)n(CCO)nc2c1]
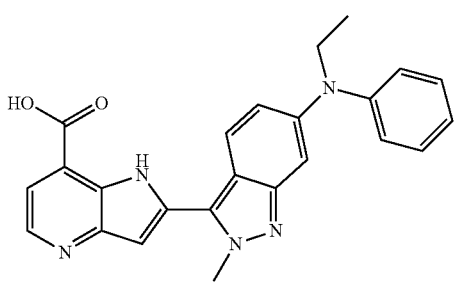 [SMILES: CCN(c1ccccc1)c1ccc2c(-c3cc4nccc(C(=O)O)c4[nH]3)n(C)nc2c1]
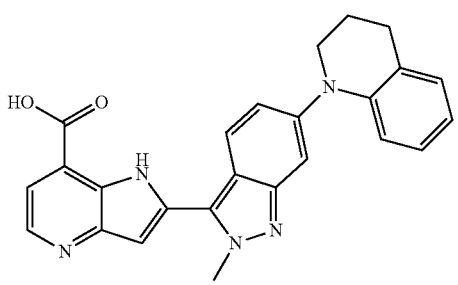 [SMILES: Cn1nc2cc(N3CCCc4ccccc43)ccc2c1-c1cc2nccc(C(=O)O)c2[nH]1]
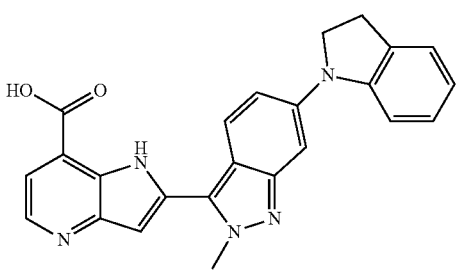 [SMILES: Cn1nc2cc(N3CCc4ccccc43)ccc2c1-c1cc2nccc(C(=O)O)c2[nH]1]
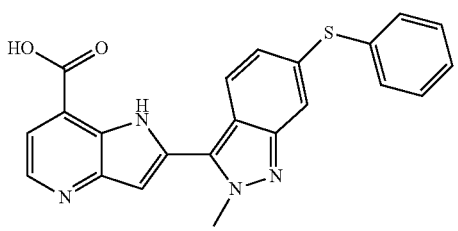 [SMILES: Cn1nc2cc(Sc3ccccc3)ccc2c1-c1cc2nccc(C(=O)O)c2[nH]1]
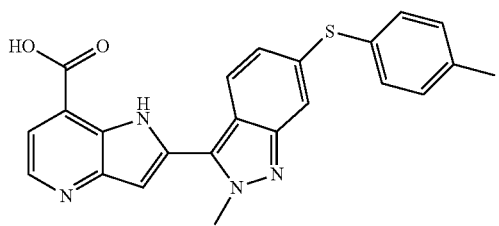

TABLE 2-continued
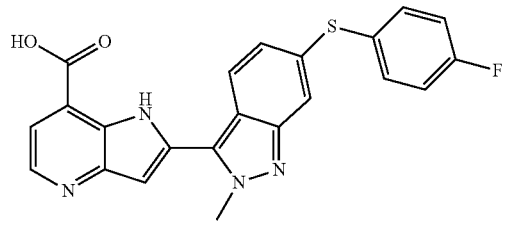 [SMILES: Cn1nc2cc(Sc3ccc(F)cc3)ccc2c1-c1cc2nccc(C(=O)O)c2[nH]1]
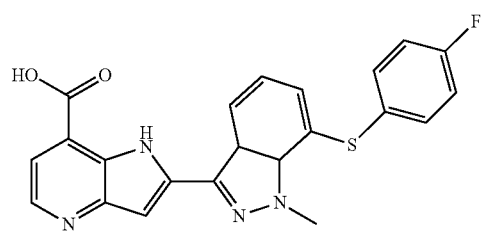 [SMILES: CN1N=C(c2cc3nccc(C(=O)O)c3[nH]2)C2C=CC=C(Sc3ccc(F)cc3)C21]
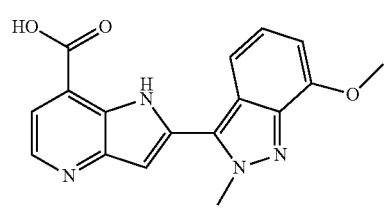 [SMILES: COc1cccc2c(-c3cc4nccc(C(=O)O)c4[nH]3)n(C)nc12]
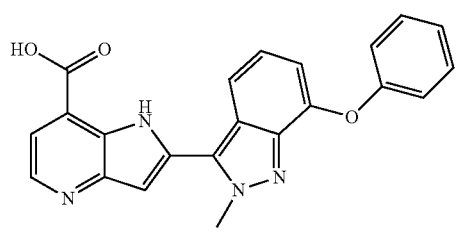 [SMILES: Cn1nc2c(Oc3ccccc3)cccc2c1-c1cc2nccc(C(=O)O)c2[nH]1]
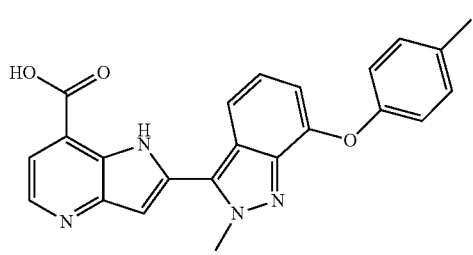 [SMILES: Cc1ccc(Oc2cccc3c(-c4cc5nccc(C(=O)O)c5[nH]4)n(C)nc23)cc1]
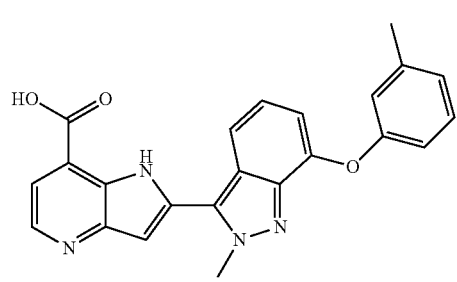 [SMILES: Cc1cccc(Oc2cccc3c(-c4cc5nccc(C(=O)O)c5[nH]4)n(C)nc23)c1]
TABLE 2-continued
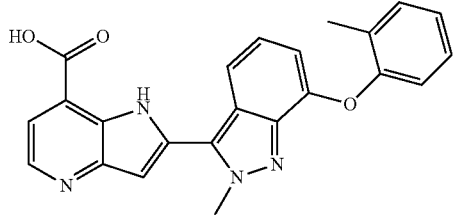 [SMILES: Cc1ccccc1Oc1cccc2c(-c3cc4nccc(C(=O)O)c4[nH]3)n(C)nc12]
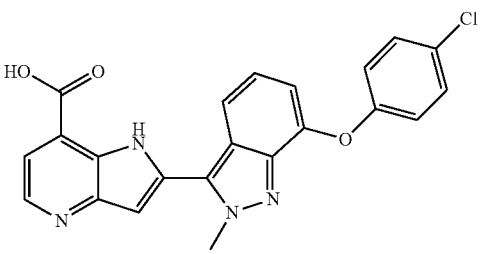 [SMILES: Cn1nc2c(Oc3ccc(Cl)cc3)cccc2c1-c1cc2nccc(C(=O)O)c2[nH]1]
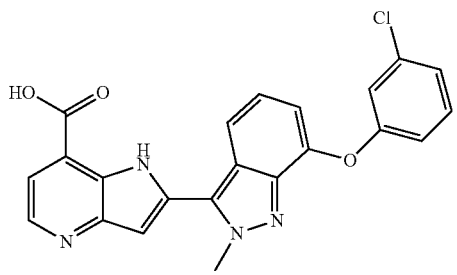 [SMILES: Cn1nc2c(Oc3cccc(Cl)c3)cccc2c1-c1cc2nccc(C(=O)O)c2[nH]1]
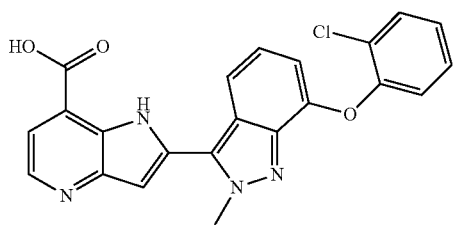 [SMILES: Cn1nc2c(Oc3ccccc3Cl)cccc2c1-c1cc2nccc(C(=O)O)c2[nH]1]
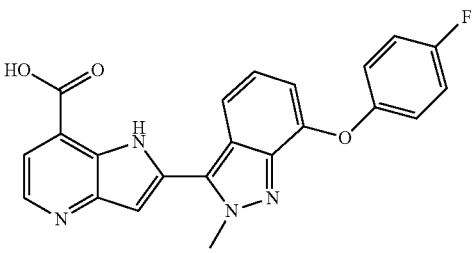 [SMILES: Cn1nc2c(Oc3ccc(F)cc3)cccc2c1-c1cc2nccc(C(=O)O)c2[nH]1]
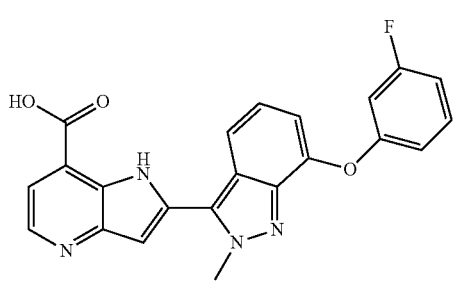 [SMILES: Cn1nc2c(Oc3cccc(F)c3)cccc2c1-c1cc2nccc(C(=O)O)c2[nH]1]

TABLE 2-continued
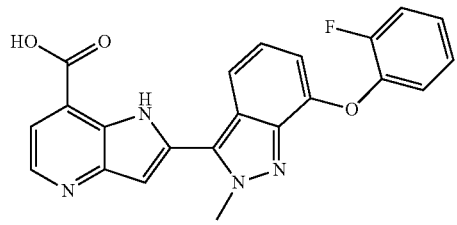 [SMILES: Cn1nc2c(Oc3ccccc3F)cccc2c1-c1cc2nccc(C(=O)O)c2[nH]1]
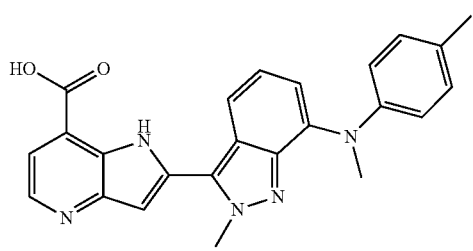 [SMILES: Cc1ccc(N(C)c2cccc3c(-c4cc5nccc(C(=O)O)c5[nH]4)n(C)nc23)cc1]
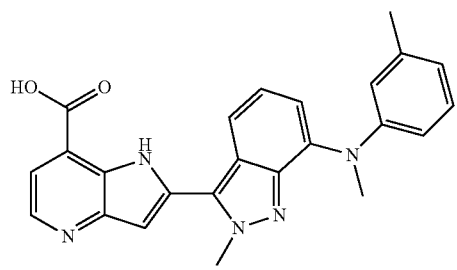 [SMILES: Cc1cccc(N(C)c2cccc3c(-c4cc5nccc(C(=O)O)c5[nH]4)n(C)nc23)c1]
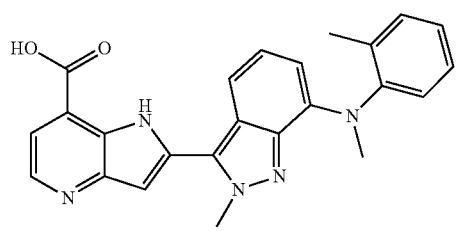 [SMILES: Cc1ccccc1N(C)c1cccc2c(-c3cc4nccc(C(=O)O)c4[nH]3)n(C)nc12]
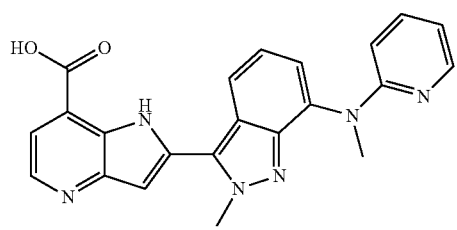 [SMILES: CN(c1ccccn1)c1cccc2c(-c3cc4nccc(C(=O)O)c4[nH]3)n(C)nc12]
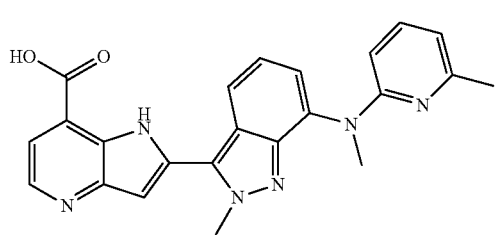 [SMILES: Cc1cccc(N(C)c2cccc3c(-c4cc5nccc(C(=O)O)c5[nH]4)n(C)nc23)n1]
TABLE 2-continued
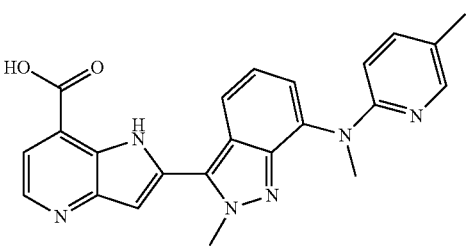 [SMILES: Cc1ccc(N(C)c2cccc3c(-c4cc5nccc(C(=O)O)c5[nH]4)n(C)nc23)nc1]
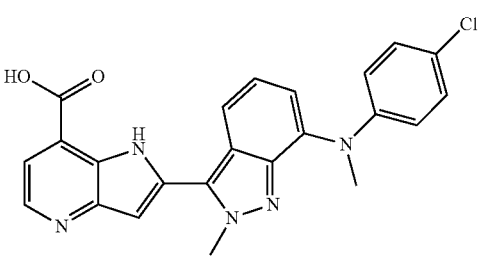 [SMILES: CN(c1ccc(Cl)cc1)c1cccc2c(-c3cc4nccc(C(=O)O)c4[nH]3)n(C)nc12]
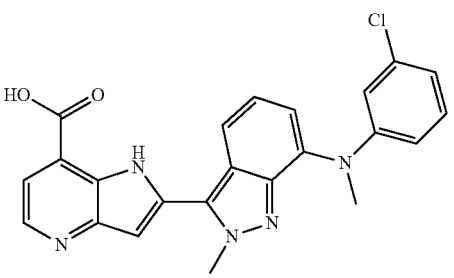 [SMILES: CN(c1cccc(Cl)c1)c1cccc2c(-c3cc4nccc(C(=O)O)c4[nH]3)n(C)nc12]
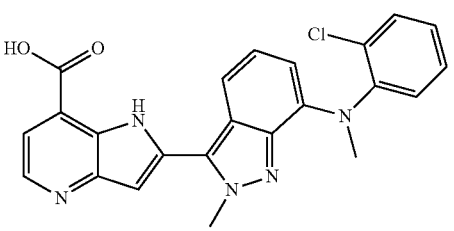 [SMILES: CN(c1ccccc1Cl)c1cccc2c(-c3cc4nccc(C(=O)O)c4[nH]3)n(C)nc12]
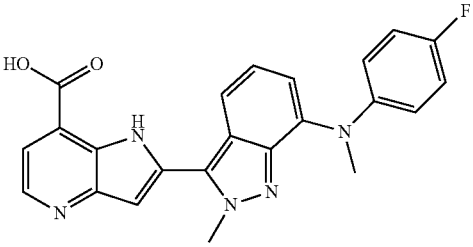 [SMILES: CN(c1ccc(F)cc1)c1cccc2c(-c3cc4nccc(C(=O)O)c4[nH]3)n(C)nc12]
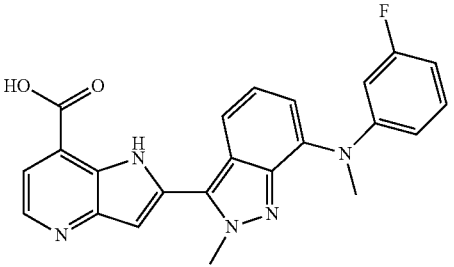 [SMILES: CN(c1cccc(F)c1)c1cccc2c(-c3cc4nccc(C(=O)O)c4[nH]3)n(C)nc12]

TABLE 2-continued
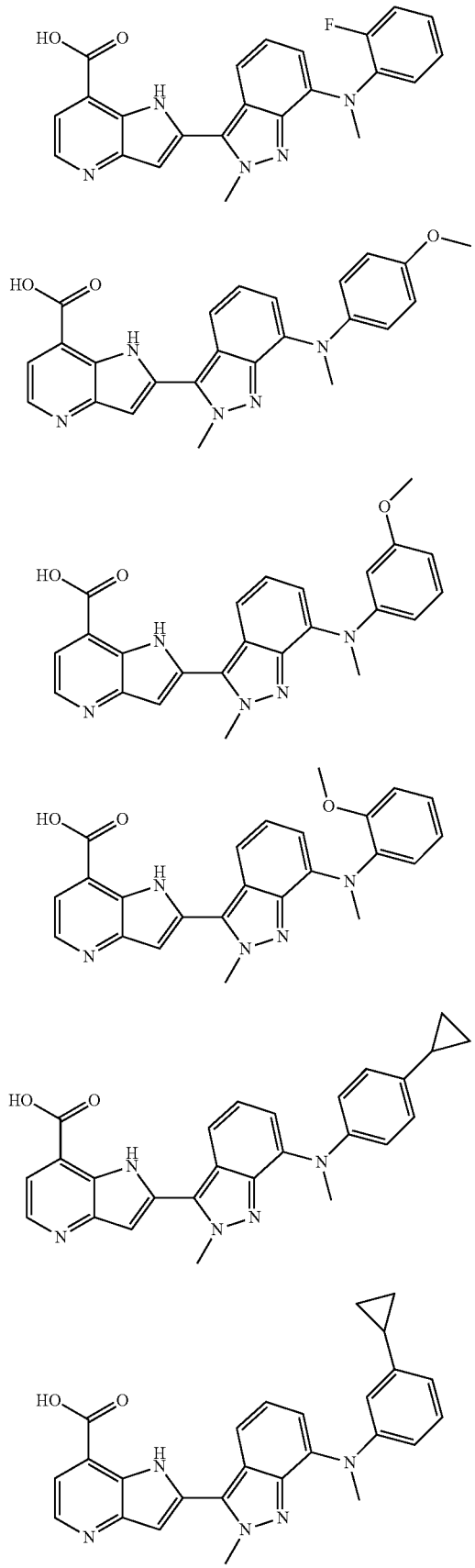
TABLE 2-continued
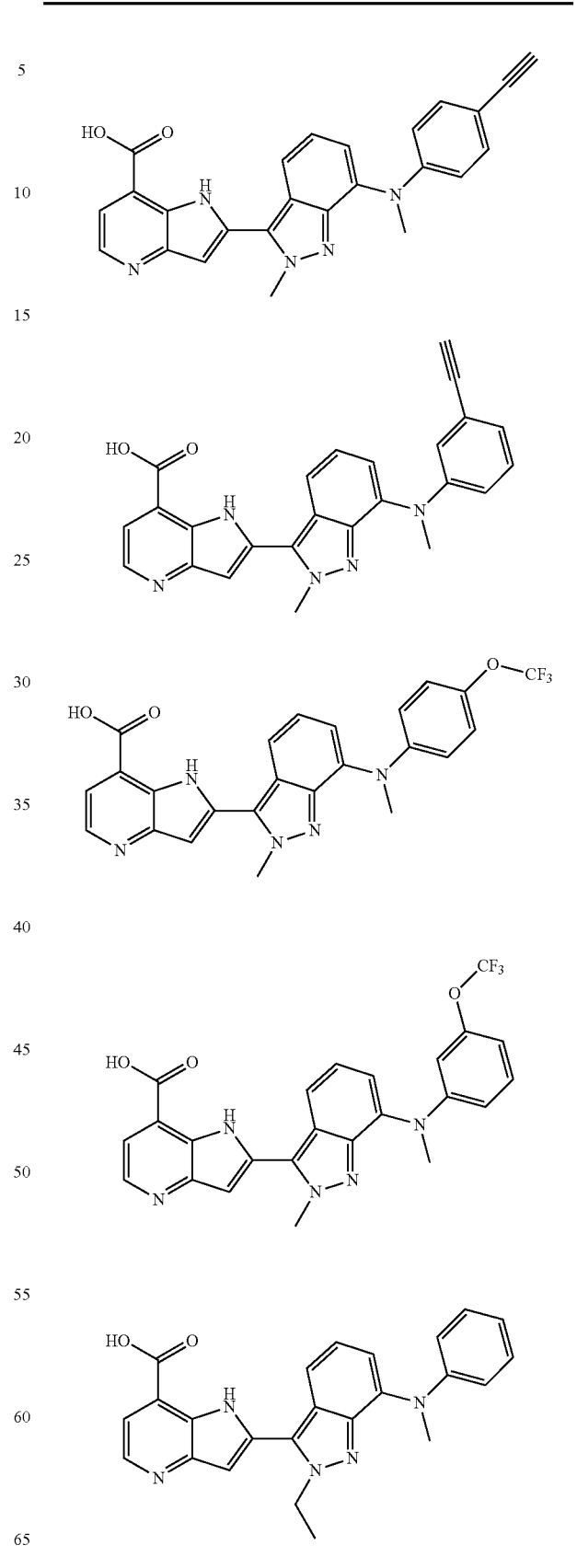

TABLE 2-continued
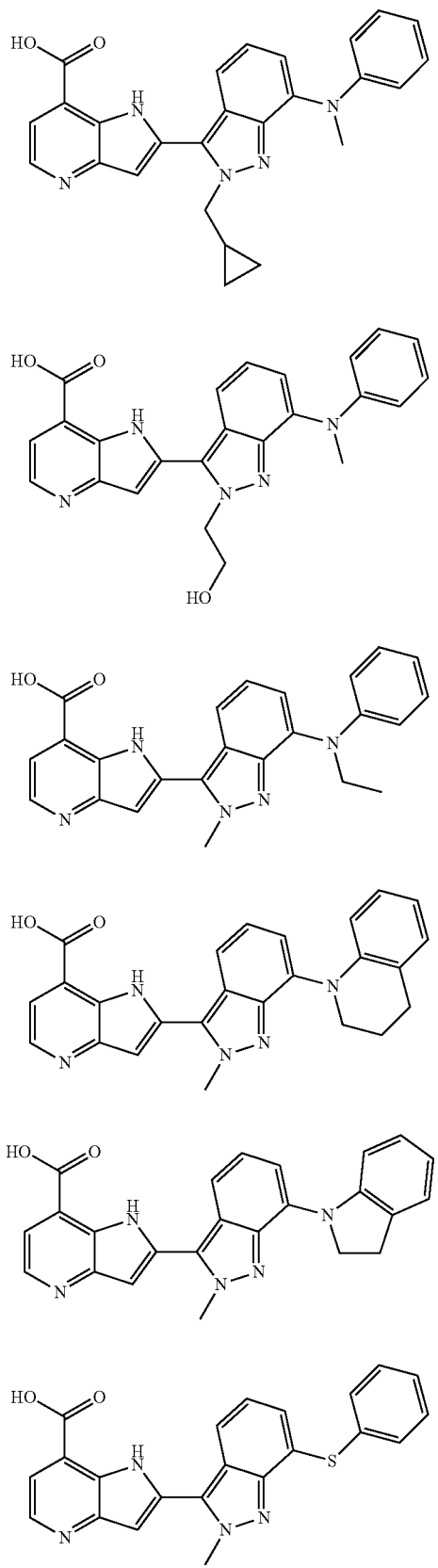
TABLE 2-continued
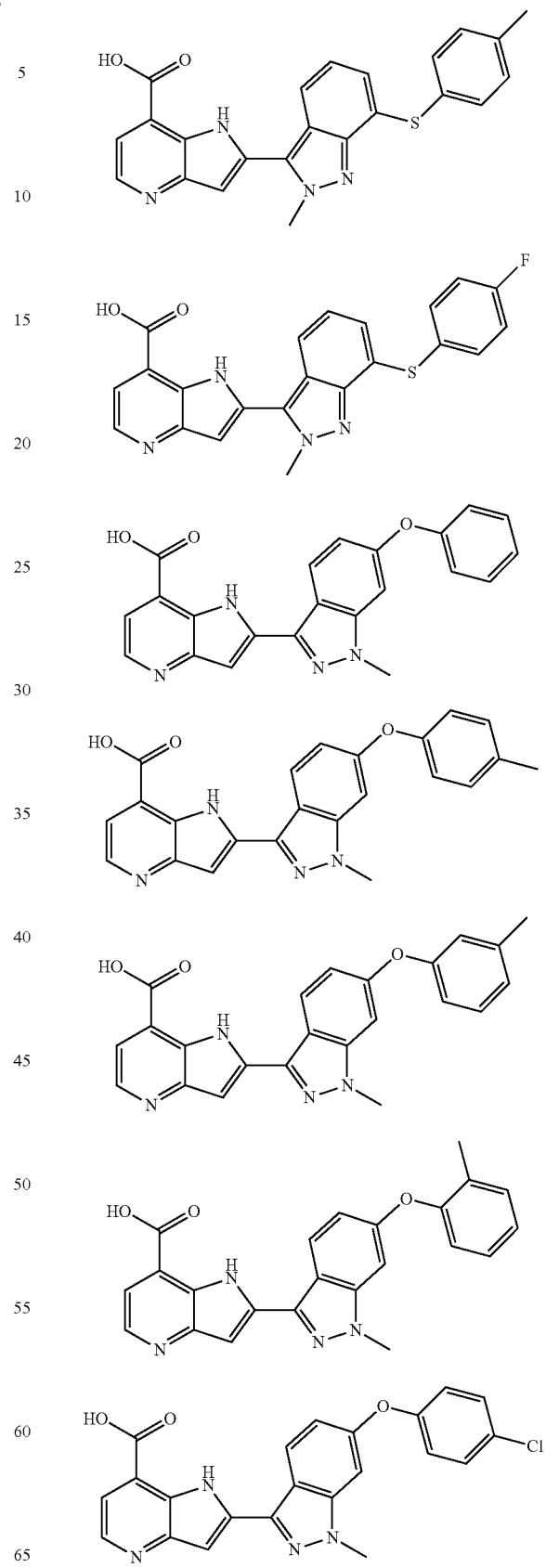

TABLE 2-continued
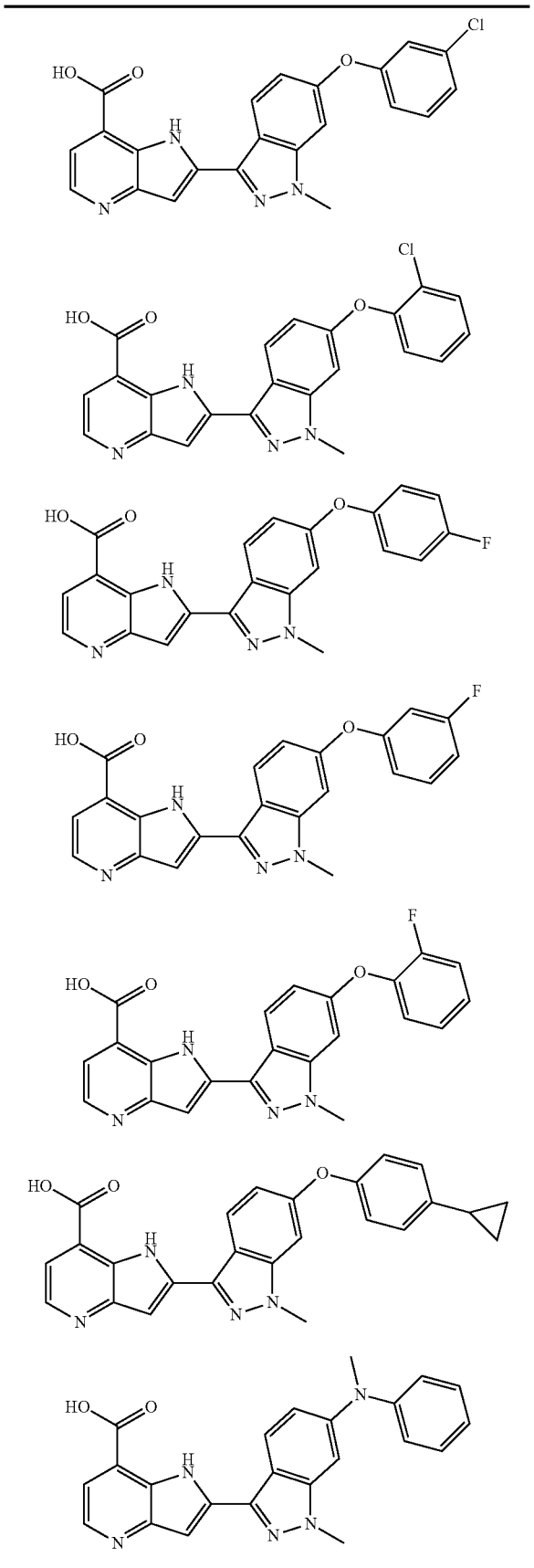
TABLE 2-continued
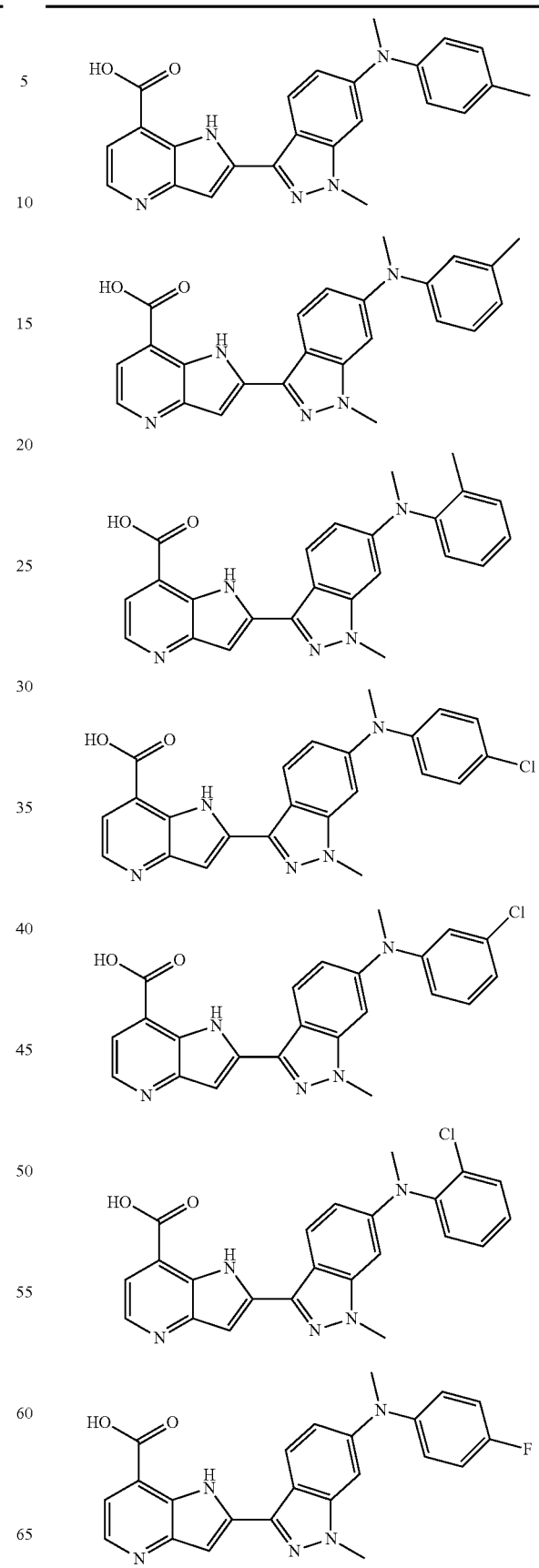

TABLE 2-continued
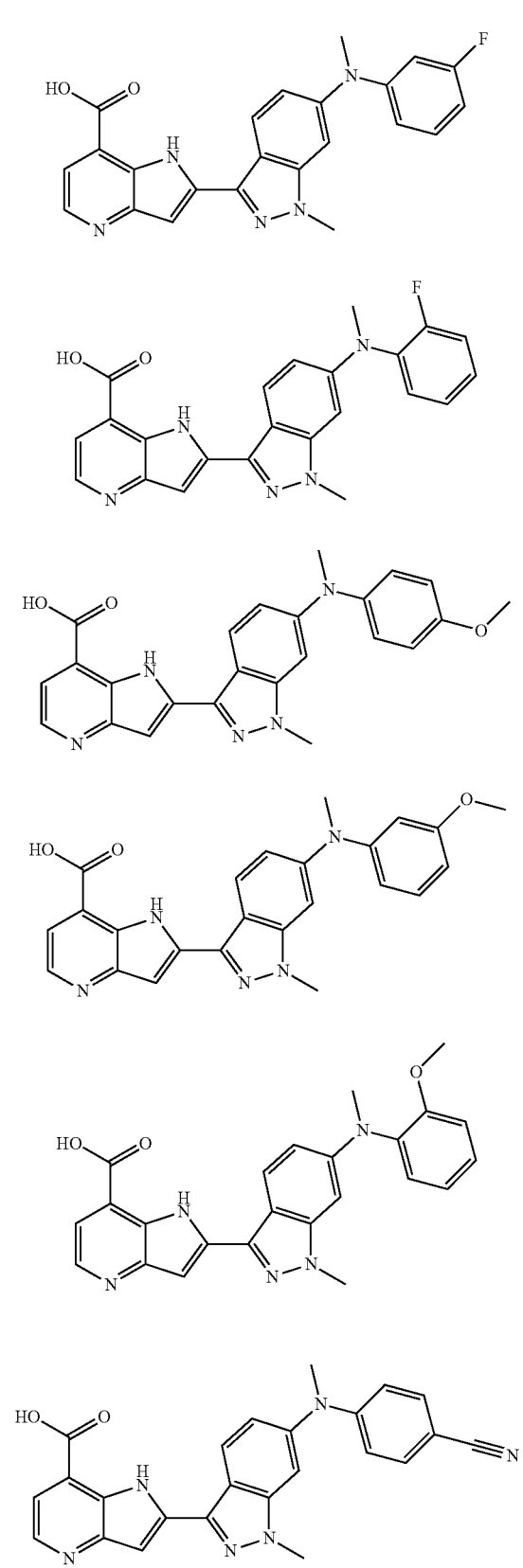
TABLE 2-continued
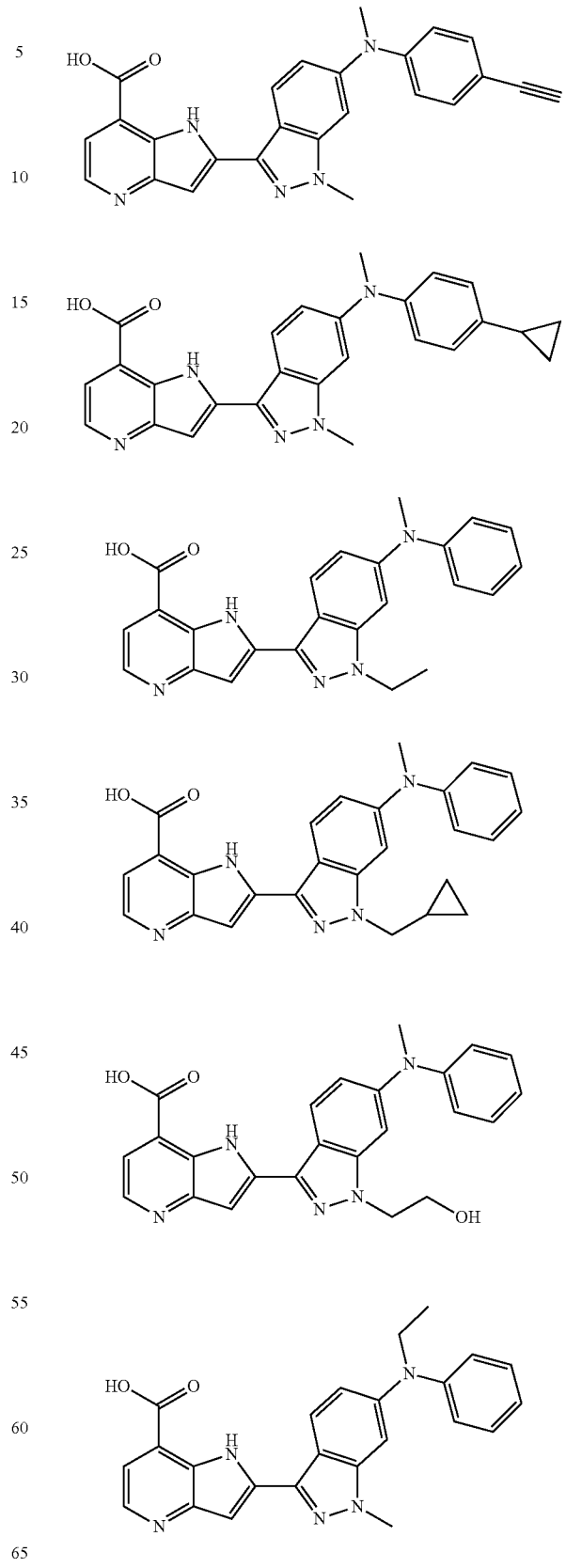

TABLE 2-continued
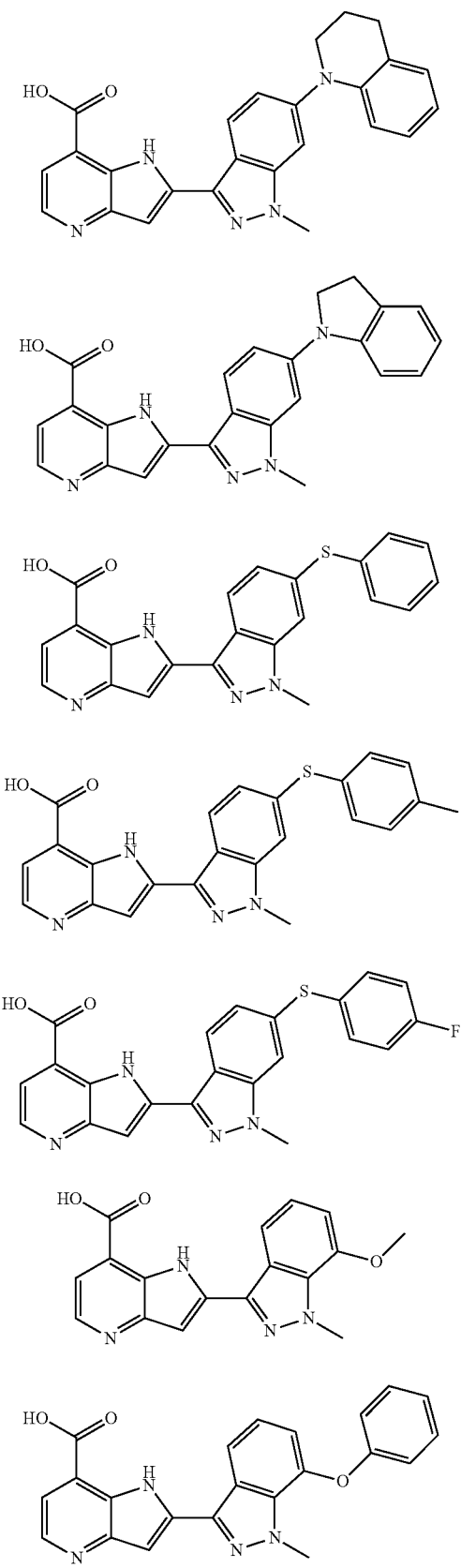
TABLE 2-continued
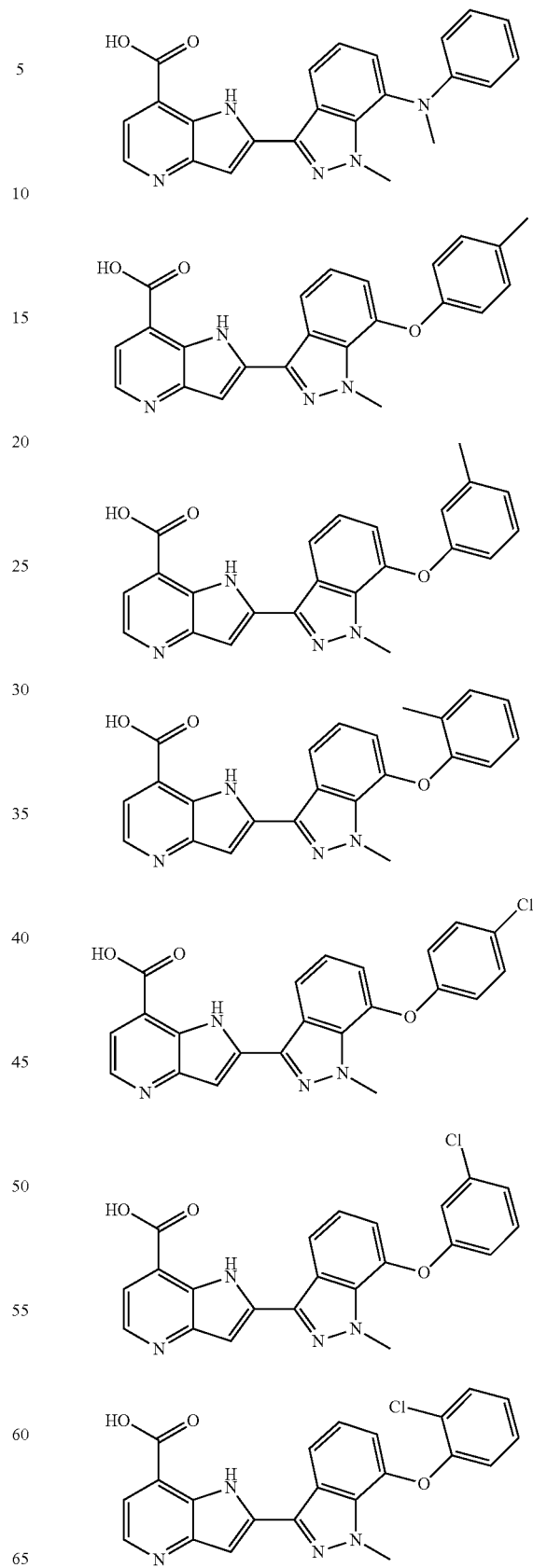

TABLE 2-continued
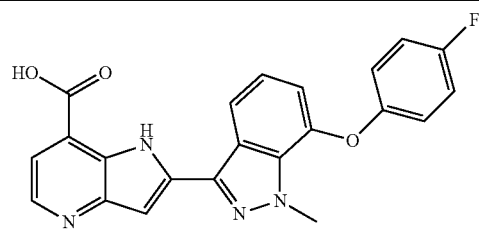
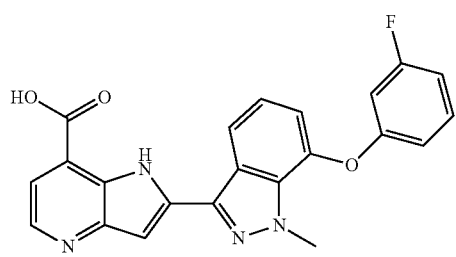 [SMILES: Cn1nc(-c2cc3nccc(C(=O)O)c3[nH]2)c2cccc(Oc3cccc(F)c3)c21]
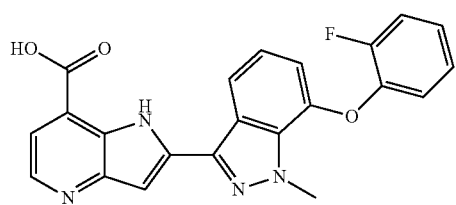 [SMILES: Cn1nc(-c2cc3nccc(C(=O)O)c3[nH]2)c2cccc(Oc3ccccc3F)c21]
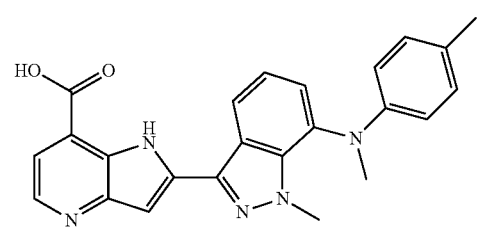
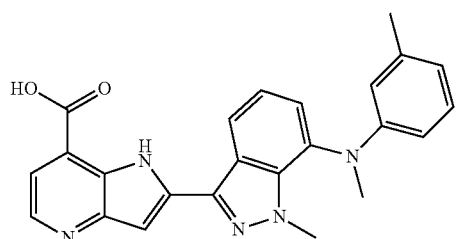
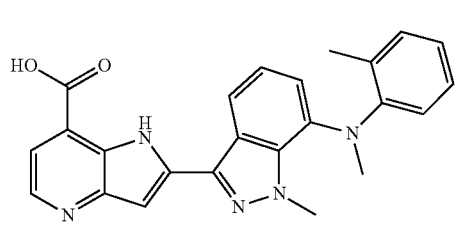 [SMILES: Cc1ccccc1N(C)c1cccc2c(-c3cc4nccc(C(=O)O)c4[nH]3)nn(C)c12]
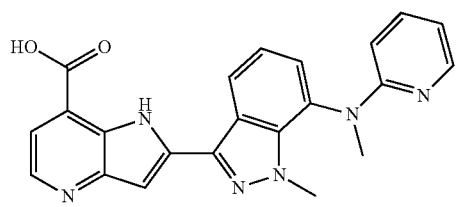 [SMILES: CN(c1ccccn1)c1cccc2c(-c3cc4nccc(C(=O)O)c4[nH]3)nn(C)c12]
TABLE 2-continued
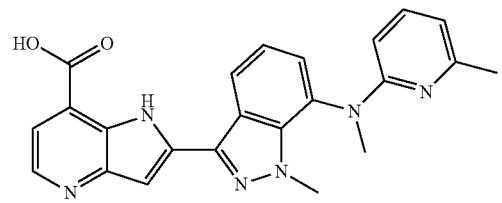 [SMILES: Cc1cccc(N(C)c2cccc3c(-c4cc5nccc(C(=O)O)c5[nH]4)nn(C)c23)n1]
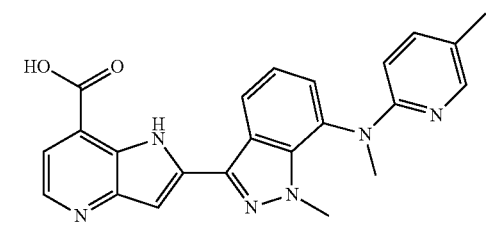 [SMILES: Cc1ccc(N(C)c2cccc3c(-c4cc5nccc(C(=O)O)c5[nH]4)nn(C)c23)nc1]
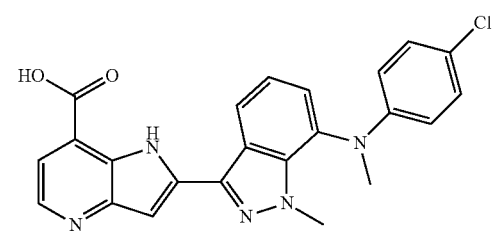 [SMILES: CN(c1ccc(Cl)cc1)c1cccc2c(-c3cc4nccc(C(=O)O)c4[nH]3)nn(C)c12]
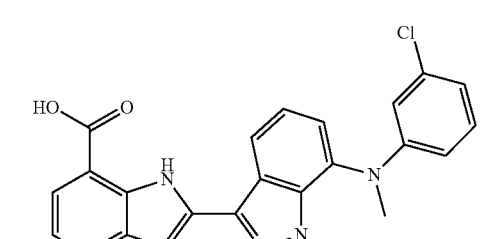
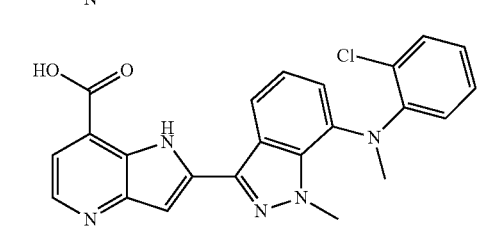
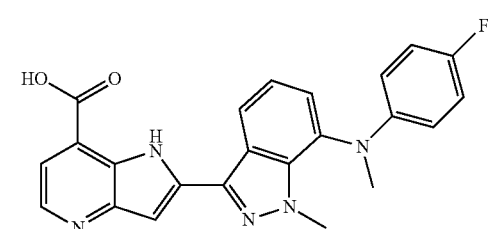
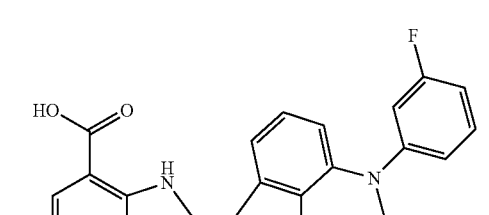

TABLE 2-continued
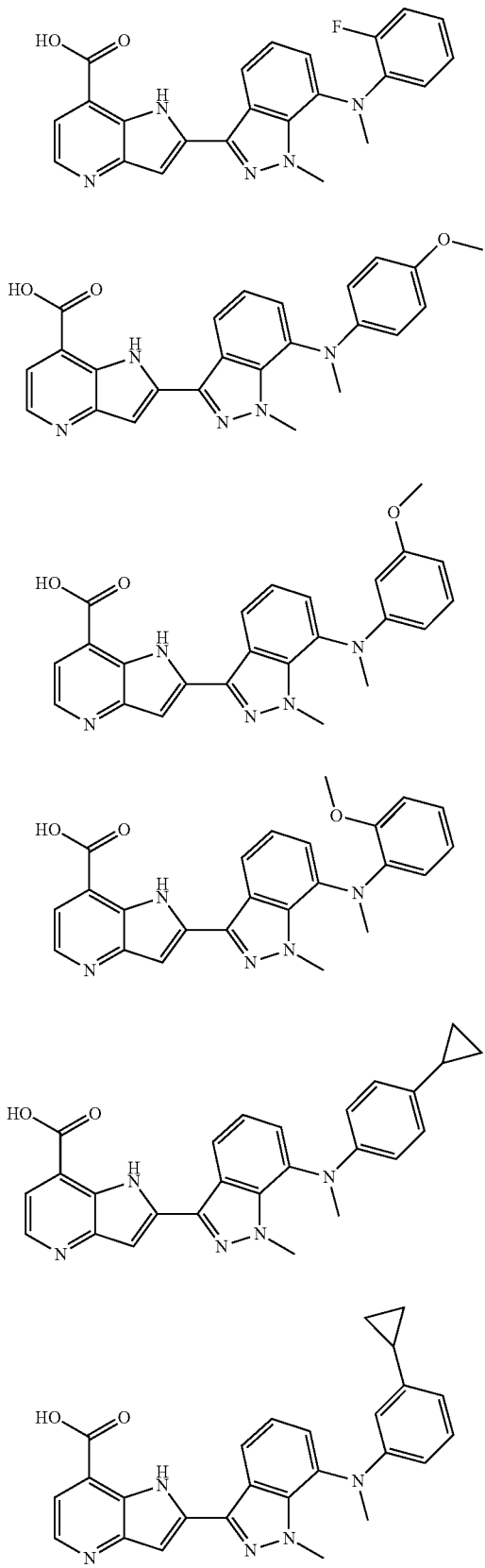
TABLE 2-continued
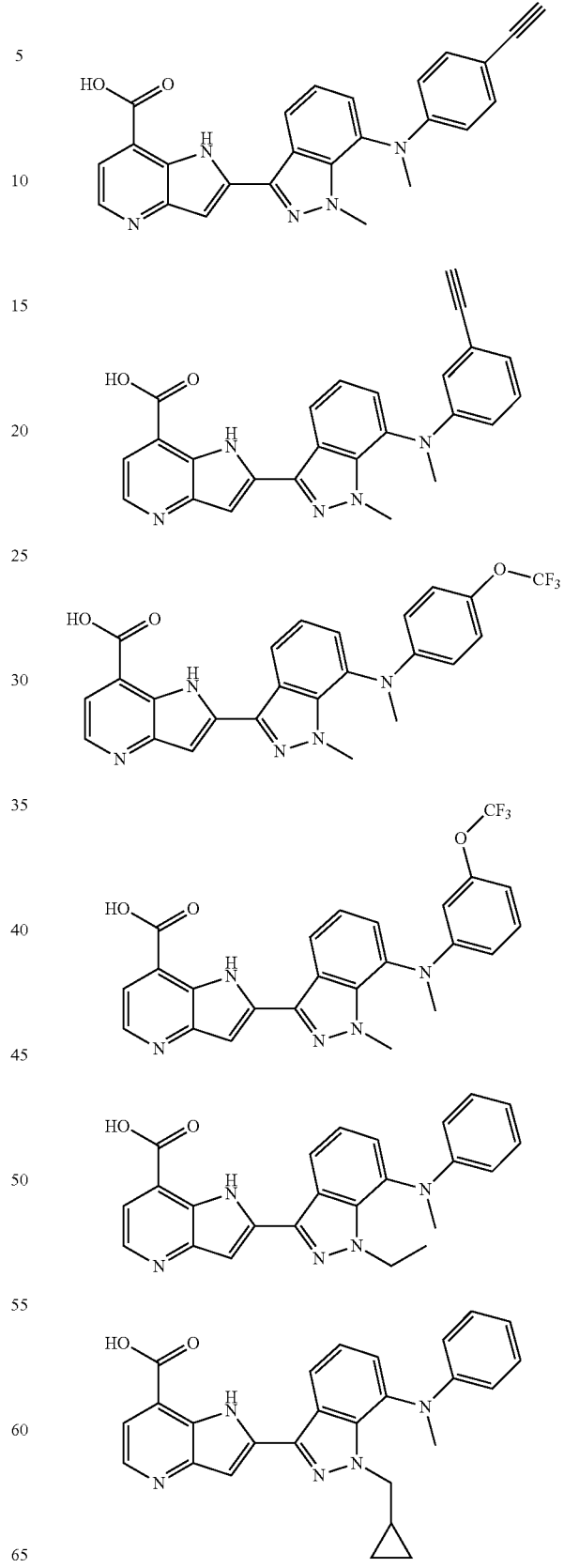

TABLE 2-continued

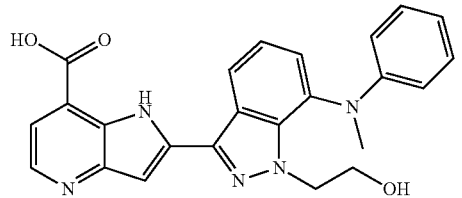 [SMILES: CN(c1ccccc1)c1cccc2c(-c3cc4nccc(C(=O)O)c4[nH]3)nn(CCO)c12]
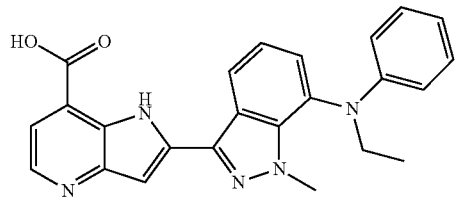 [SMILES: CCN(c1ccccc1)c1cccc2c(-c3cc4nccc(C(=O)O)c4[nH]3)nn(C)c12]
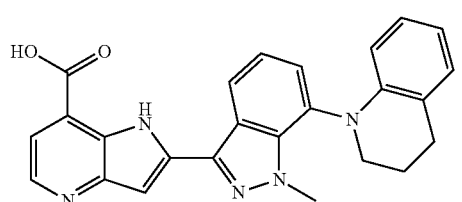
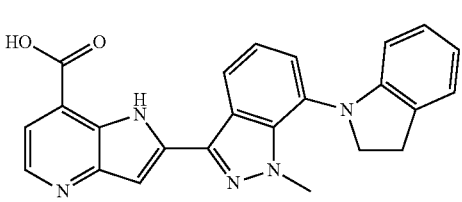 [SMILES: Cn1nc(-c2cc3nccc(C(=O)O)c3[nH]2)c2cccc(N3CCc4ccccc43)c21]
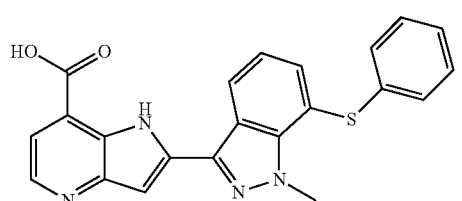
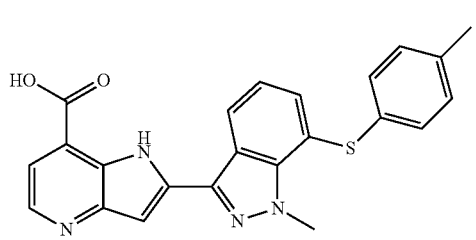 [SMILES: Cc1ccc(Sc2cccc3c(-c4cc5nccc(C(=O)O)c5[nH]4)nn(C)c23)cc1]
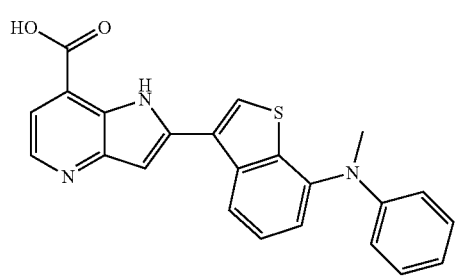 [SMILES: CN(c1ccccc1)c1cccc2c(-c3cc4nccc(C(=O)O)c4[nH]3)csc12]

TABLE 2-continued

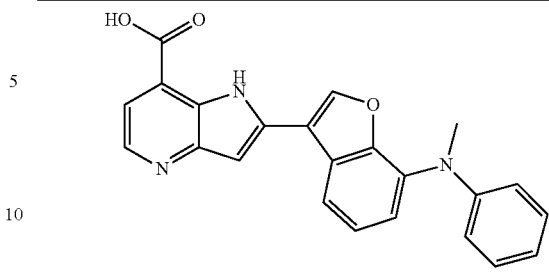
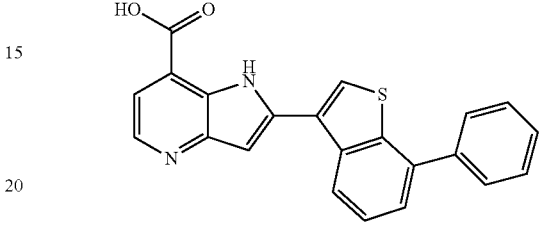
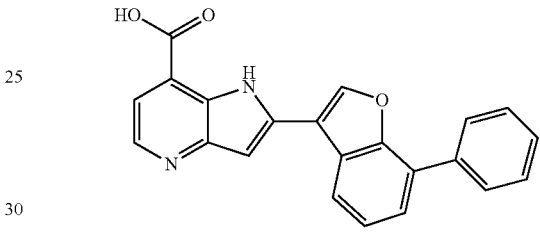

Preparation of the Substituted Pyrrolopyridine Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R.V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted pyrrolopyridine derivative compounds described herein is P. H. Stahl & C. G. Wermuth "Handbook of Pharmaceutical Salts", Verlag Helvetica Chimica Acta, Zurich, 2002.

The substituted pyrrolopyridine derivative compounds are prepared by the general synthetic routes described below in Schemes 1-3.

Scheme 1

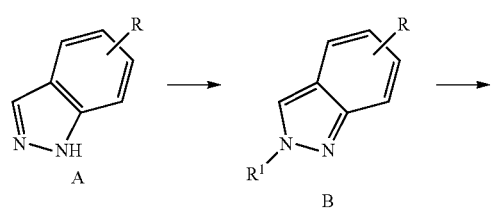

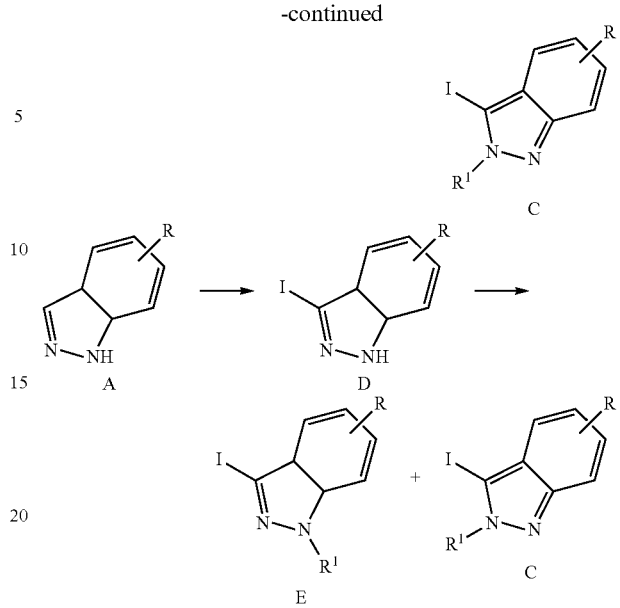

Referring to Scheme 1, the substituted indazole A is selectively alkylated with $R^1$—X to give compound B (see Cheung, J. Org. Chem. 2003, 4093). Compound B is iodinated in the presence of base to give compound C. Alternatively, compound A is iodinated in the presence of base to give compound D. Compound D is alkylated with $R^1$—X to give a mixture of compound E (major) and compound C (minor).

Scheme 2

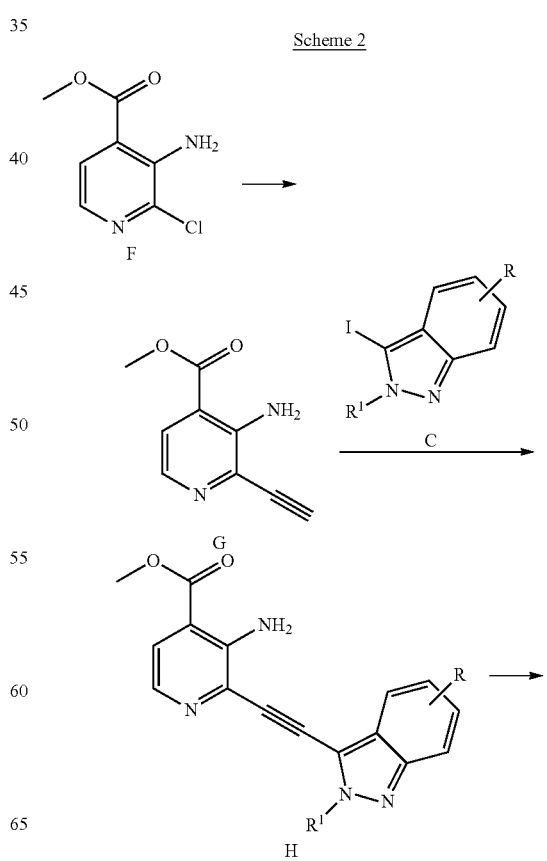

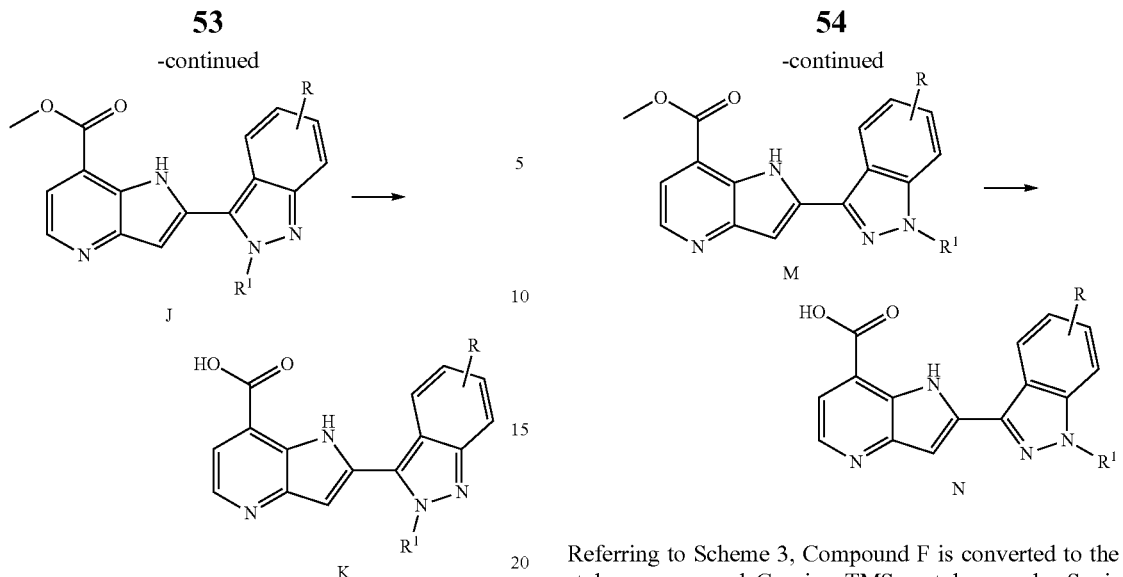

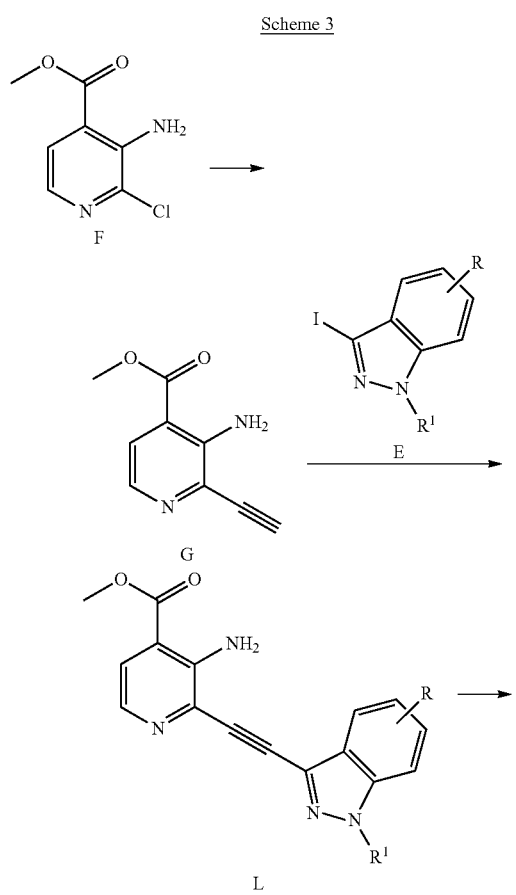

Referring to Scheme 2, Compound F is converted to the acetylene compound G using TMS-acetylene under Sonigashira conditions, followed by TMS deprotection with TBAF. Compound G and the halo-indazole C are converted to compound H under Sonigashira coupling conditions. Compound H is heated in the presence of base and copper in order to cyclize to the compound J. Compound J is hydrolyzed under basic conditions to give compound K.

Referring to Scheme 3, Compound F is converted to the acetylene compound G using TMS-acetylene under Sonigashira conditions, followed by TMS deprotection with TBAF. Compound G and the halo-indazole E are converted to compound L under Sonigashira coupling conditions. Compound L is heated in the presence of base and copper in order to cyclize to the compound M. Compound M is hydrolyzed under basic conditions to give compound N.

In each of the above reaction procedures or schemes, the various substituents may be selected from among the various substituents otherwise taught herein.

Pharmaceutical Compositions

In certain embodiments, a substituted pyrrolopyridine derivative compound as described herein is administered as a pure chemical. In other embodiments, the substituted pyrrolopyridine derivative compound as described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: Science & Practice of Pharmacy (Gennaro, 21st Ed. Mack Pub. Co., Easton, Pa. (2005)), the disclosure of which is hereby incorporated herein by reference, in its entirety.

Accordingly, provided herein is a pharmaceutical composition comprising at least one substituted pyrrolopyridine derivative compound as described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

In certain embodiments, the substituted pyrrolopyridine derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. See, e.g., Remington: Science & Practice of Pharmacy (Gennaro, 21st Ed. Mack Pub. Co., Easton, Pa. (2005).

The dose of the composition comprising at least one substituted pyrrolopyridine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenosyl methionine (SAM) to histones. Histone methylation is known to participate in a diverse range of biological processes including heterochromatin formation, X-chromosome inactivation, and transcriptional regulation. Lachner et al., J. Cell Sci. 116:2117 (2003); Margueron et al., Curr. Opin. Genet. Dev. 15:163 (2005).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylated one or more of H3K4, H3K9, H3K27, H3K36 and/or H3K79. Alternately, an H4 demethylase may demethylated histone H4K20. Demethylases are known which can demethylated either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri- and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and α-ketoglutarate, wherein oxidative decarboxylation of α-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al., Nature Reviews/Genetics 7:715 (2006). The JARID1 family contains several conserved domains: JmjN, ARID, JmjC, PHD and a C5HC2 zing finger.

JARID1A, also called KDM5A or RBP2, was initially found as a binding partner of retinoblastoma ($R^b$) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastoma binding protein 2 (RBP2) histone demethylase suppresses tumorigenesis in mice lacking $R^b1$ or Men1 (Lin et al. Proc. Natl. Acad. Sci. USA, Aug. 16, 2011, 108(33),13379-86; doi: 10.1073/pnas. 1110104108) and lead to the conclusion that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-3σ, and knockdown of JARID1B was found to increase the levels of tri-methylated H3K4 at these genes.

In an additional embodiment is a method for inhibiting a histone-demethylase enzyme comprising contacting a histone demethylase enzyme with a compound of Formula (I), or a pharmaceutically acceptable salt thereof.

In an additional embodiment is the method for inhibiting a histone-demethylase enzyme, wherein the histone-demethylase enzyme comprises a JmjC domain. In an additional embodiment is the method for inhibiting a histone-demethylase enzyme, wherein the histone-demethylase enzyme is JMJD2C.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a JmjC domain (e.g., a histone demethylase such as a JMJD2C protein(s)).

In an additional embodiment is a method for treating cancer in subject in need thereof comprising administering to the subject a composition comprising a compound of Formula (I), or a pharmaceutically acceptable salt thereof.

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound of Formula (I), or a pharmaceutically acceptable salt thereof, wherein the tumor is characterized by a loss of retinoblastoma gene (RBl) function.

In an additional embodiment is a method for inhibiting the growth of a tumor comprising administering a composition comprising a compound of Formula (I), or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

1. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1a: Methyl 3-amino-2-ethynylpyridine-4-carboxylate

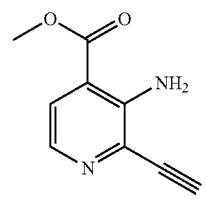

A mixture of methyl 3-amino-2-chloropyridine-4-carboxylate (1.86 g, 10 mmol), TMS-acetylene (1.18 g, 12 mmol), Pd(PPh$_3$)$_2$Cl$_2$ (350 mg, 0.50 mmol), CuI (48 mg, 0.25 mmol), TEA (5.05 g, 50 mmol) and acetonitrile (50 mL) was purged with nitrogen and stirred at 40° C. overnight. Solvent was removed and the residue was dissolved in dichloromethane and filtered. The filtrate was concentrated and re-dissolved in THF (10 mL). The mixture was cooled 0° C. and TBAF (1M, 0.35 mL) was added dropwise, and the reaction stirred 30 min. The mixture was concentrated and purified by silica gel chromatography (PE/EA=10/1 to 5/1) to afford 1.1 g, (62%) of the title compound as a yellow solid. [M+H] Calc'd for C$_9$H$_8$N$_2$O$_2$, 177; Found, 177.

Preparation 1b: 3-Iodo-6-methoxy-2-methyl-2H-indazole

To a mixture of 6-methoxy-2-methyl-2H-indazole (900 mg, 5.55 mmol) in DMF (30 mL) was added KOH (1.25 g, 22.2 mmol) followed by portion-wise addition of I$_2$ (3.0 g, 22 mmol). The reaction was allowed to stir at room temp for 16 hr. Upon completion, the reaction was quenched with NaHCO3 (sat'd, 20 mL) and the content was extracted with ethyl acetate (30 mL). The organics were washed with brine, dried over Na$_2$SO$_4$, and concentrated in vacuo. The residue was purified by flash chromatography on silica gel (PE/EA=2/1) to afford 1.19 g (74%) of the title compound as a yellow solid. [M+H] Calc'd for C$_9$H$_9$IN$_2$O, 289; Found, 289.

Preparation 1c: Methyl 3-amino-2-[2-(6-methoxy-2-methyl-2H-indazol-3-yl)-ethynyl]pyridine-4-carboxylat

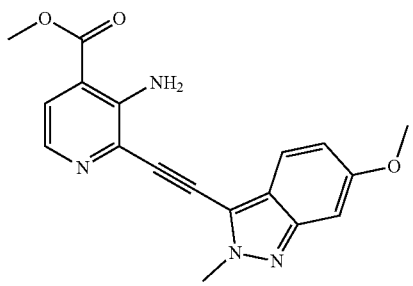

A round-bottom flask charged with 3-iodo-6-methoxy-2-methyl-2H-indazole (432 mg, 1.50 mmol) in acetonitrile (10 mL), methyl 3-amino-2-ethynylpyridine-4-carboxylate (264 mg, 1.50 mmol), Pd(PPh$_3$)$_2$Cl$_2$ (53 mg, 0.075 mmol), CuI (8 mg, 0.04 mmol), and TEA (2 ml) was purged with nitrogen for 2 min and allowed to stir at 40° C. for 16 hr. The reaction was filtered and the filtrate was concentrated in vacuo. The residue was purified by silica gel chromatography (PE/EA=1/2) to afford 154 mg (30%) of the title compound as a brown solid. [M+H] Calc'd for C$_{18}$H$_{16}$N$_4$O$_3$, 337; Found, 337.

Preparation 1d: Methyl 2-(6-methoxy-2-methyl-2H-indazol-3-yl)-1H-pyrrolo[3,2-b]pyridine-7-carboxylate

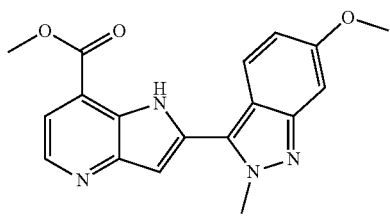

A round-bottom flask charged with methyl 3-amino-2-[2-(6-methoxy-2-methyl-2H-indazol-3-yl)ethynyl]pyridine-4-carboxylate (154 mg, 0.458 mmol) in DMF (10 mL), CaCO$_3$ (46 mg, 0.46 mmol), and CuI (22 mg, 0.11 mmol) was purged with nitrogen and stirred for 12 hr at 120° C. The reaction concentrated in vacuo, and the residue was taken up in dichloromethane and filtered. The filtrate was concentrated in vacuo and purified by prep-HPLC to afford 20 mg (13%) of the title compound as a yellow solid. [M+H] Calc'd for C$_{18}$H$_{16}$N$_4$O$_3$, 337; Found, 337.

Example 1: 2-(6-Methoxy-2-methyl-2H-indazol-3-yl)-1H-pyrrolo[3,2-b]pyridine-7-carboxylic Acid

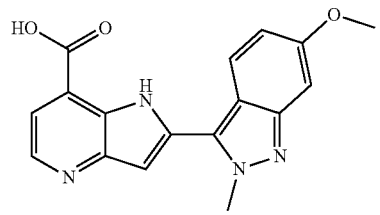 [SMILES: COc1ccc2c(-c3cc4nccc(C(=O)O)c4[nH]3)n(C)nc2c1]

A round-bottom flask charged with methyl 2-(6-methoxy-2-methyl-2H-indazol-3-yl)-1H-pyrrolo[3,2-b]pyridine-7-carboxylate (20 mg, 0.059 mmol) in THF (1 mL), LiOH.H$_2$O (5 mg, 0.12 mmol) and water (1 mL) was allowed to stir at rt for 3 h. The pH was adjusted to 6~7 with HCl (1N), and the precipitate filtered. The solid was washed with dichloromethane and dried to afford 13 mg (68%) of the title compound as an orange solid. 1H NMR (300 MHz, DMSO-d$_6$): δ 4.11 (3H, s), 4.25 (3H, s), 7.23 (1H, J=9.3 Hz, d), 7.50-7.53 (2H, m), 7.83 (1H, J=9.0 Hz, d), 8.45-8.49 (2H, m), 12.79 (1H, s). LCMS (mobile phase: 10%-95% Acetonitrile-Water-0.02% NH$_4$Ac): purity is >95%, Rt=2.804 min. [M+H] Calc'd for C$_{17}$H$_{14}$N$_4$O$_3$, 323; Found, 323.

Preparation 2a: 5-Methoxy-2-methyl-2H-indazole

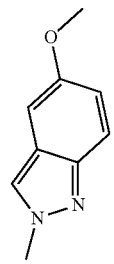

To a solution of 5-methoxy-indazole (1.0 g, 6.7 mmol) in ethyl acetate (10 ml) was added BF$_4$O(CH$_3$)$_3$(1.3 g, 8.9 mmol). The solution was stirred at rt for 3 h. Sat. NaHCO3 aq. (10 ml) was added and extracted with ethyl acetate (20 ml). Organics were dried over Na$_2$SO$_4$, concentrated, and purified by flash chromatography on silica gel (PE/EA=2/1) to afford 0.64 g (59%) of the title compound as a yellow solid. [M+H] Calc'd for C$_9$H$_{10}$N$_2$O, 163; Found, 163.

Preparation 2b: 3-Iodo-5-methoxy-2-methyl-2H-indazole

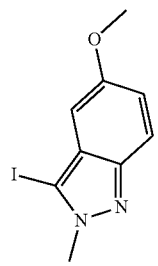

The title compound was prepared in 700/% yield from 5-methoxy-2-methyl-2H-indazole according to the procedure for Preparation 1b. [M+H] Calc'd for $C_9H_9IN_2O$, 289; Found, 289.

Example 2: 2-(5-Methoxy-2-methyl-2H-indazol-3-yl)-1H-pyrrolo[3,2-b]pyridine-7-carboxylic Acid

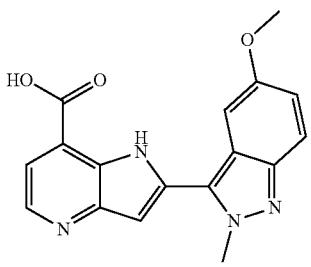 [SMILES: COc1ccc2nn(C)c(-c3cc4nccc(C(=O)O)c4[nH]3)c2c1]

The title compound was prepared in <10% overall yield starting from Preparation 2b according to the procedure sequence for the preparation of Example 1 (Preparation 1c, Preparation 1d, Example 1). $^1$H NMR (300 MHz, DMSO-$d_6$): δ 3.78 (3H, s), 4.22 (3H, s), 6.97-7.01 (2H, m), 7.12 (1H, s), 7.59-7.63 (2H, m), 8.55-8.57 (1H, m), 11.62 (1H, s). LCMS (mobile phase: 5%-95% Acetonitrile-Water-0.02% TFA): purity is >95%, Rt=2.853 min. [M+H] Calc'd for $C_{17}H_{14}N_4O_3$, 323; Found, 323.

Preparation 3a: Methyl 3-amino-2-[2-(6-chloro-2-methyl-2H-indazol-3-yl)-ethynyl]pyridine-4-carboxylate

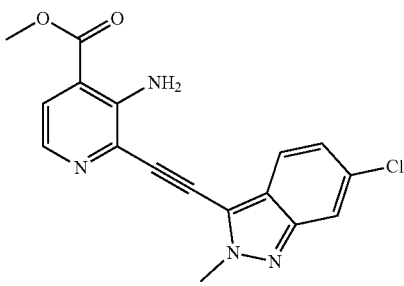 [SMILES: COC(=O)c1ccnc(C#Cc2c3ccc(Cl)cc3nn2C)c1N]

A mixture of methyl 3-amino-2-ethynylpyridine-4-carboxylate (176 mg, 1 mmol), 6-chloro-3-iodo-2-methyl-2H-indazole (1 mmol), Pd(ACN)$_2$Cl$_2$ (7 mg, 0.025 mmol), xphos (24 mg, 0.05 mmol), K$_2$CO$_3$ (552 mg, 4 mmol) and acetonitrile (10 mL) was purged with nitrogen and stirred at 80° C. overnight. The reaction was filtered, and the filtrate was concentrated and purified by silica gel chromatography (PE/EA=5/1~2/1) to afford 300 mg (88%) of the title compound as a yellow solid. [M+H] Calc'd for $C_{17}H_{13}ClN_4O_2$, 341; Found, 341.

Preparation 3b: Methyl 2-(6-chloro-2-methyl-2H-indazol-3-yl)-1H-pyrrolo [3,2-b]pyridine-7-carboxylate

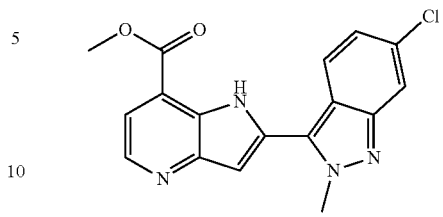

A mixture of Preparation 3a (170 mg, 0.5 mmol), CaCO$_3$ (100 mg, 1 mmol), CuI (24 mg, 0.125 mmol) and DMF (10 mL) was purged with nitrogen and stirred for 1 hr at 120° C. The solvent was removed, and the residue was dissolved in dichloromethane and filtered. The filtrate was concentrated and purified by prep-HPLC to give 65 mg (38%) of the title compound. $^1$H NMR (400 MHz, DMSO-$d_6$): δ 3.99 (3H, s), 4.27 (3H, s), 7.15-7.21 (2H, m), 7.70-7.82 (3H, m), 8.62 (1H, d, J=4.8 Hz), 11.86 (1H, br s). LCMS (mobile phase: 5%-95% Acetonitrile-Water-0.02% NH$_4$Ac): purity is >95%, RT=3.930 min. [M+H] Calc'd for $C_{17}H_{13}ClN_4O_2$, 341; Found, 341.

Example 3: 2-(6-Chloro-2-methyl-2H-indazol-3-yl)-1H-pyrrolo[3,2-b]-pyridine-7-carboxylic Acid

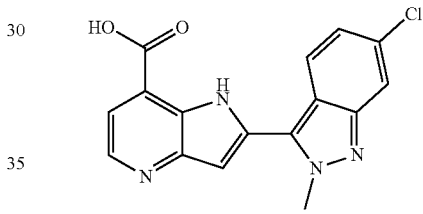

A mixture of Preparation 3b (0.16 mmol) and NaOH (14 mg, 0.35 mmol) in methanol (1 mL) and water (1 mL) was heated at 60° C. for 15 min. The solution was cooled to room temp, and the pH was adjusted to 3~4 with aq. 1N HCl. The resulting precipitate was collected by filtration, washing with DCM, and dried under vacuum to give 20 mg (60%) of the title compound. $^1$H NMR (400 MHz, DMSO-$d_6$): δ 4.27 (3H, s), 7.15-7.19 (2H, m), 7.68-7.80 (3H, m), 8.60 (1H, s), 11.82 (1H, br). LCMS (mobile phase: 5%-95% Acetonitrile-Water-0.02% NH$_4$Ac): purity is >95%, RT=2.482 min. [M+H] Calc'd for $C_{16}H_{11}ClN_4O_2$, 327; Found, 327.

Preparation 4a: Methyl 3-amino-2-{2-[2-methyl-5-(trifluoromethyl)-2H-indazol-3-yl]ethynyl}pyridine-4-carboxylate

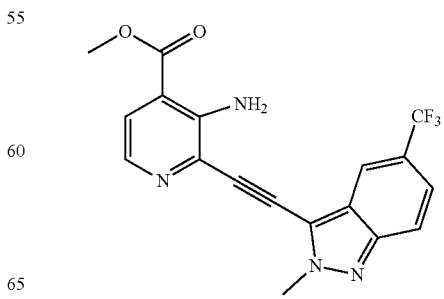

The title compound was prepared in 85% yield from 3-iodo-2-methyl-5-(trifluoromethyl)-2H-indazole according to the procedure for Preparation 3a. [M+H] Calc'd for $C_{18}H_{13}F_3N_4O_2$, 375; Found, 375.

Preparation 4b: Methyl 2-[2-methyl-5-(trifluoromethyl)-2H-indazol-3-yl]-1H-pyrrolo [3,2-b]pyridine-7-carboxylate

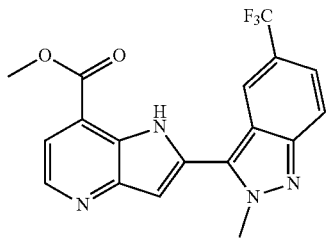 [SMILES: COC(=O)c1ccnc2cc(-c3c4cc(C(F)(F)F)ccc4nn3C)[nH]c12]

The title compound was prepared in 43% yield from Preparation 4a according to the procedure for Preparation 3b. $^1$H NMR (300 MHz, DMSO-d$_6$): δ 4.01 (3H, s), 4.32 (3H, s), 7.30 (1H, s), 7.55-7.59 (1, m), 7.71-7.73 (1H, m), 7.93 (1H, d, J=9.3 Hz), 8.10 (1H, s), 8.62-8.64 (1H, m), 11.97 (1H, s). LCMS (mobile phase: 10%-95% Acetonitrile-Water-0.02% NH$_4$Ac): purity is >95%, RT=3.766 min. [M+H] Calc'd for $C_{18}H_{13}F_3N_4O_2$, 375; Found, 375.

Example 4: 2-[2-Methyl-5-(trifluoromethyl)-2H-indazol-3-yl]-1H-pyrrolo[3,2-b]pyridine-7-carboxylic Acid

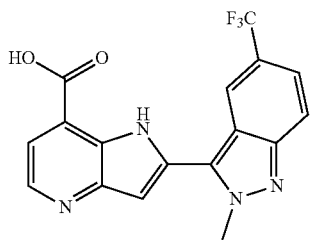 [SMILES: Cn1nc2ccc(C(F)(F)F)cc2c1-c1cc2nccc(C(=O)O)c2[nH]1]

The title compound was prepared in 70% yield from Preparation 4b according to the procedure for Example 3. $^1$H NMR (400 MHz, DMSO-d$_6$): δ 4.31 (3H, s), 7.26 (1H, s), 7.56 (1H, d, J=9.2 Hz), 7.68 (1H, d, J=4.8 Hz), 7.91 (1H, d, J=9.2 Hz), 8.09 (1H, s), 8.59-8.63 (1H, m), 11.91 (1H, s), 13.81 (1H, br). LCMS (mobile phase: 10%-95% Acetonitrile-Water-0.02% NH$_4$Ac): purity is >95%, RT=2.371 min. [M+H] Calc'd for $C_{17}H_{11}F_3N_4O_2$, 361; Found, 361.

Preparation 5a: Methyl 3-amino-2-{2-[2-methyl-5-(trifluoromethoxy)-2H-indazol-3-yl]ethynyl}pyridine-4-carboxylate

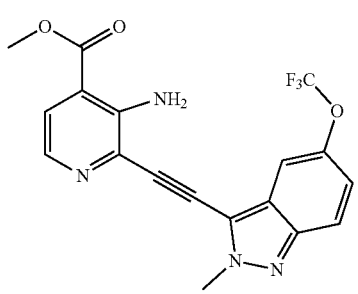 [SMILES: COC(=O)c1ccnc(C#Cc2c3cc(OC(F)(F)F)ccc3nn2C)c1N]

The title compound was prepared in 79% yield from 3-iodo-2-methyl-5-(trifluoro-methoxy)-2H-indazole according to the procedure for Preparation 3a. [M+H] Calc'd for $C_{18}H_{13}F_3N_4O_3$, 391; Found, 391.

Preparation 5b: Methyl 2-[2-methyl-5-(trifluoromethoxy)-2H-indazol-3-yl]-1H-pyrrolo [3,2-b]pyridine-7-carboxylate

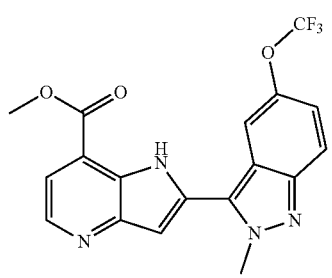 [SMILES: COC(=O)c1ccnc2cc(-c3c4cc(OC(F)(F)F)ccc4nn3C)[nH]c12]

The title compound was prepared in 66% yield from Preparation 5a according to the procedure for Preparation 3b. $^1$H NMR (400 MHz, DMSO-d$_6$): δ 3.99 (3H, s), 4.29 (3H, s), 7.22 (1H, s), 7.32-7.34 (1H, m), 7.63 (1H, s), 7.71 (1H, d, J=4.4 Hz), 7.86 (1H, d, J=9.2 Hz), 8.62 (1H, d, J=4.8 Hz), 11.86 (1H, s). LCMS (mobile phase: 10%-95% Acetonitrile-Water-0.02% NH$_4$Ac): purity is >95%, Rt=3.857 min. [M+H] Calc'd for $C_{18}H_{13}F_3N_4O_3$, 391; Found, 391.

Example 5: 2-[2-Methyl-5-(trifluoromethoxy)-2H-indazol-3-yl]-1H-pyrrolo[3,2-b]pyridine-7-carboxylic Acid

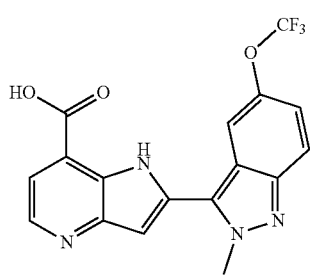 [SMILES: Cn1nc2ccc(OC(F)(F)F)cc2c1-c1cc2nccc(C(=O)O)c2[nH]1]

The title compound was prepared in 88% yield from Preparation 5b according to the procedure for Example 3. $^1$H NMR (400 MHz, DMSO-d$_6$): δ 4.29 (3H, s), 7.19 (1H, s), 7.31-7.33 (1H, m), 7.63-7.68 (2H, m), 7.84 (1H, d, J=9.2 Hz), 8.60 (1H, d, J=4.8 Hz), 11.82 (1H, s), 13.83 (1H, br s). LCMS (mobile phase: 5%-95% Acetonitrile-Water-0.02% NH$_4$Ac): purity is >95%, RT=2.610 min. [M+H] Calc'd for $C_{18}H_{11}F_3N_4O_3$, 377; Found, 377.

Preparation 6a: Methyl 3-amino-2-[2-(5-cyclopropyl-2-methyl-2H-indazol-3-yl)ethynyl]pyridine-4-carboxylate

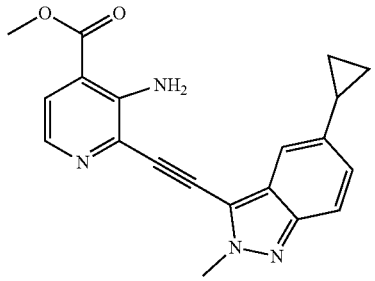 [SMILES: COC(=O)c1ccnc(C#Cc2c3cc(C4CC4)ccc3nn2C)c1N]

The title compound was prepared in 81% yield from 5-cyclopropyl-3-iodo-2-methyl-2H-indazole according to the procedure for Preparation 3a. [M+H] Calc'd for C$_{20}$H$_{18}$N$_4$O$_2$, 347; Found, 347.

Preparation 6b: Methyl 2-(5-cyclopropyl-2-methyl-2H-indazol-3-yl)-1H-pyrrolo[3,2-b]pyridine-7-carboxylate

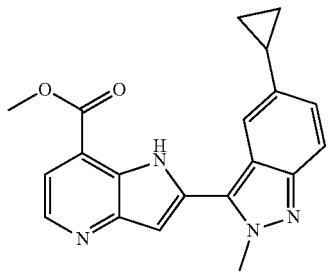 [SMILES: COC(=O)c1ccnc2cc(-c3c4cc(C5CC5)ccc4nn3C)[nH]c12]

The title compound was prepared in 40% yield from Preparation 6a according to the procedure for Preparation 3b. $^1$H NMR (400 MHz, CDCl$_3$): δ 0.76-0.78 (2H, m), 0.98-1.02 (2H, m), 2.02-2.04 (1H, m), 4.08 (3H, s), 4.37 (3H, s), 7.06-7.13 (2H, m), 7.12 (1H, s), 7.52 (1H, s), 7.66-7.71 (1H, m), 8.66 (1H, d, J=4.8 Hz), 9.94 (1H, s). LCMS (mobile phase: 5%-95% Acetonitrile-Water-0.02% NH$_4$Ac): purity is >95%, RT=3.972 min. [M+H] Calc'd for C$_{20}$H$_{18}$N$_4$O$_2$, 347; Found, 347.

Example 6: 2-(5-Cyclopropyl-2-methyl-2H-indazol-3-yl)-1H-pyrrolo[3,2-b]pyridine-7-carboxylic Acid

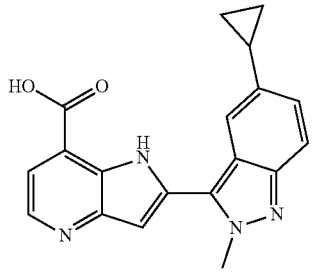 [SMILES: Cn1nc2ccc(C3CC3)cc2c1-c1cc2nccc(C(=O)O)c2[nH]1]

The title compound was prepared in 85% yield from Preparation 6b according to the procedure for Example 3. $^1$H NMR (400 MHz, DMSO-d$_6$): δ 0.69-0.71 (2H, m), 0.91-0.94 (2H, m), 2.01-2.04 (1H, m), 4.24 (3H, s), 7.04-7.12 (2H, m), 7.41 (1H, s), 7.57-7.65 (2H, m), 8.57 (1H, d, J=5.2 Hz), 11.64 (1H, s), 13.76 (1H, br s). LCMS (mobile phase: 5%-95% Acetonitrile-Water-0.02% NH$_4$Ac): purity is >95%, Rt=2.612 min. [M+H] Calc'd for C$_{19}$H$_{16}$N$_4$O$_2$, 333; Found, 333.

Example 7: 2-(5-Chloro-2-methyl-2H-indazol-3-yl)-1H-pyrrolo[3,2-b]pyridine-7-carboxylic Acid

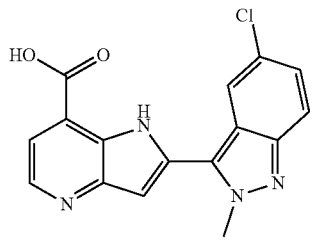 [SMILES: Cn1nc2ccc(Cl)cc2c1-c1cc2nccc(C(=O)O)c2[nH]1]

The title compound was prepared in <10% overall yield starting from 6-chloro-3-iodo-2-methyl-2H-indazole according to the procedure sequence for the preparation of Example 1 (Preparation 1c, Preparation 1d, Example 1). $^1$H NMR (400 MHz, DMSO-d$_4$): δ 4.36 (3H, s), 6.66 (1H, s), 7.06 (1H, d, J=4.6 Hz), 7.18 (1H, dd, J=8.9, 2.1 Hz), 7.57 (1H, d, J=8.9 Hz), 7.89 (1H, s), 7.92 (1H, d, J=4.6 Hz). [M+H] Calc'd for C$_{16}$H$_{11}$ClN$_4$O$_2$, 327; Found, 327.

Preparation 8a: 6-Chloro-3-iodo-1H-indazole

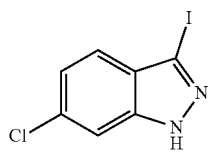 [SMILES: Clc1ccc2c(I)n[nH]c2c1]

To a solution of 6-chloro-indazole (3.0 g, 20 mmol) and KOH (4.2 g, 74 mmol) in DMF (80 mL) was added I$_2$ (10 g, 40 mmol) at 0° C. The mixture was stirred at room temp for 3 hr. The reaction was quenched with sat. Na$_2$S$_2$O$_3$ (30 mL) and extracted with EA (50 mL). Organics were dried over Na$_2$SO$_4$, filtered, and the filtrate was concentrated and purified by silica gel chromatography (PE/EA=5/1) to afford 3.9 g (71%/) of the title compound as a red solid. [M+H] Calc'd for C$_7$H$_4$ClIN$_2$, 279; Found, 279.

Preparation 8b:
6-Chloro-1-ethyl-3-iodo-1H-indazole

Preparation 8c:
6-Chloro-2-ethyl-3-iodo-2H-indazole

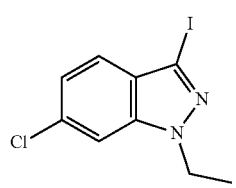

8b

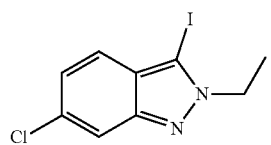

8c

A mixture of 6-chloro-3-iodo-1H-indazole (1.11 g, 4 mmol), $K_2CO_3$ (1.11 g, 8 mmol), and iodoethane (1.6 mL, 20 mmol) in acetonitrile (15 mL) was stirred at 80° C. overnight. The reaction was filtered and the filtrate was concentrated and purified by silica gel chromatography (PE/EA=1/1) to afford the two products as yellow solids. 6-chloro-1-ethyl-3-iodo-1H-indazole (866 mg, 60%/): [M+H] Calc'd for $C_9H_8ClIN_2$, 307; Found, 307. 6-chloro-2-ethyl-3-iodo-2H-indazole (260 mg, 18%): [M+H] Calc'd for $C_9H_8ClIN_2$, 307; Found, 307.

Preparation 8d: Methyl 3-amino-2-[2-(6-chloro-2-ethyl-2H-indazol-3-yl)ethynyl]pyridine-4-carboxylate

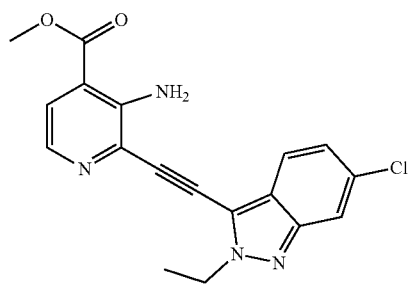 [SMILES: CCn1nc2cc(Cl)ccc2c1C#Cc1nccc(C(=O)OC)c1N]

The title compound was prepared in 80% yield from Preparation 8c according to the general procedure outline for Preparation 1c. [M+H] Calc'd for $C_{18}H_{15}ClN_4O_2$, 355; Found, 355.

Preparation 8e: Methyl 2-(6-chloro-2-ethyl-2H-indazol-3-yl)-1H-pyrrolo[3,2-b]pyridine-7-carboxylate

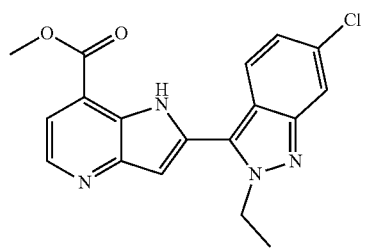 [SMILES: CCn1nc2cc(Cl)ccc2c1-c1cc2nccc(C(=O)OC)c2[nH]1]

The title compound was prepared in 11% yield from Preparation 8d according to the general procedure outline for Preparation 1d. $^1$H NMR (400 MHz, DMSO-$d_6$): δ 1.57 (3H, J=7.2 Hz, t), 4.08 (3H, s), 4.64-4.70 (2H, m), 7.10 (1H, s), 7.17-7.19 (1H, m), 7.72-7.74 (2H, m), 7.84 (1H, d, J=5.2 Hz), 8.60 (1H, d, J=4.8 Hz). LCMS (mobile phase: 5%-95% Acetonitrile-Water-0.02% $NH_4Ac$): purity is >95%, RT=4.144 min. [M+H] Calc'd for $C_{18}H_{15}ClN_4O_2$, 355; Found, 355.

Example 8: 2-(6-Chloro-2-ethyl-2H-indazol-3-yl)-1H-pyrrolo[3,2-b]pyridine-7-carboxylic Acid

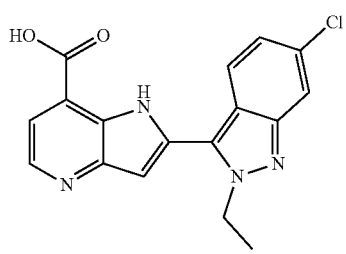 [SMILES: CCn1nc2cc(Cl)ccc2c1-c1cc2nccc(C(=O)O)c2[nH]1]

The title compound was prepared in 64% yield from Preparation 8e according to the general procedure outline for Example 1. $^1$H NMR (400 MHz, DMSO-$d_6$): δ 1.45 (3H, J=7.2 Hz, t), 4.56-4.58 (2H, m), 7.13-7.15 (2H, m), 7.68-7.72 (2H, m), 7.82 (1H, s), 8.62 (1H, J=4.8 Hz, d), 11.93 (1H, br s). LCMS (mobile phase: 5%-95% Acetonitrile-Water-0.02% $NH_4Ac$): purity >95%, RT=2.872 min. [M+H] Calc'd for $C_{17}H_{13}ClN_4O_2$, 341; Found, 341.

Preparation 9a:
6-Chloro-1-(cyclopropylmethyl)-3-iodo-1H-indazole

Preparation 9b:
6-Chloro-2-(cyclopropylmethyl)-3-iodo-2H-indazole

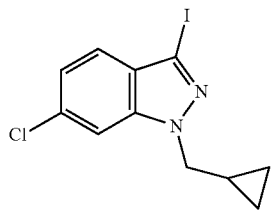

9a

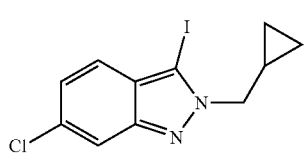

9b

The title compounds were prepared from (iodomethyl)cyclopropane and 6-chloro-3-iodo-1H-indazole according to the procedure for Preparation 8b and 8c. 6-chloro-1-(cyclopropylmethyl)-3-iodo-1H-indazole: (61%). [M+H] Calc'd for $C_{11}H_{10}ClIN_2$, 333; Found, 333. 6-chloro-2-(cyclopropylmethyl)-3-iodo-2H-indazole: (19%). [M+H] Calc'd for $C_{11}H_{10}ClIN_2$, 333; Found, 333.

Preparation 9c: Methyl 3-amino-2-(2-[6-chloro-2-(cyclopropylmethyl)-2H-indazol-3-yl]ethynyl) pyridine-4-carboxylate

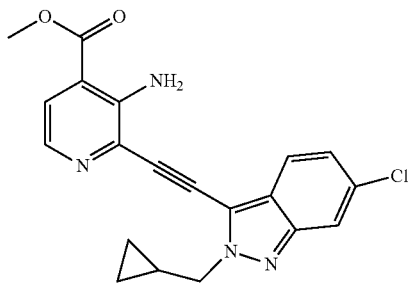 [SMILES: COC(=O)c1ccnc(C#Cc2c3ccc(Cl)cc3nn2CC2CC2)c1N]

The title compound was prepared in 82% yield from Preparation 9b according to the general procedure outline for Preparation 1c. [M+H] Calc'd for $C_{20}H_{17}ClN_4O_2$, 381; Found, 381.

Preparation 9d: Methyl 2-[6-chloro-2-(cyclopropylmethyl)-2H-indazol-3-yl]-1H-pyrrolo [3,2-b]pyridine-7-carboxylate

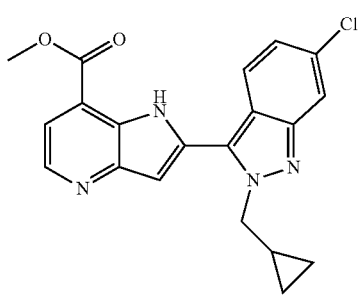 [SMILES: COC(=O)c1ccnc2cc(-c3c4ccc(Cl)cc4nn3CC3CC3)[nH]c12]

The title compound was prepared in 31% yield from Preparation 9c according to the general procedure outline for Preparation 1d. $^1$H NMR (400 MHz, DMSO-d$_6$): δ 0.30-0.32 (2H, m), 0.54-0.56 (2H, m), 1.34-1.37 (1H, m), 4.08 (3H, s), 4.51 (2H, J=7.2 Hz, d), 7.11 (1H, s), 7.17 (1H, J=8.0 Hz, d), 7.71-7.73 (2H, m), 7.84-7.85 (1H, m), 8.60 (1H, s). LCMS (mobile phase: 5%-95% Acetonitrile-Water-0.02% NH$_4$Ac): purity is >95%, RT=4.238 min. [M+H] Calc'd for $C_{20}H_{17}ClN_4O_2$, 381; Found, 381.

Example 9: 2-[6-Chloro-2-(cyclopropylmethyl)-2H-indazol-3-yl]-1H-pyrrolo[3,2-b]pyridine-7-carboxylic Acid

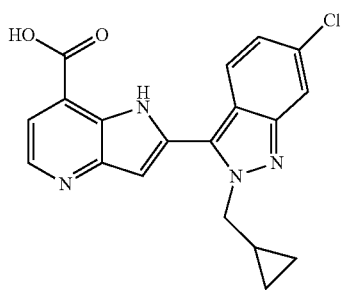 [SMILES: O=C(O)c1ccnc2cc(-c3c4ccc(Cl)cc4nn3CC3CC3)[nH]c12]

The title compound was prepared in 73% yield from Preparation 9d according to the general procedure outline for Example 1. $^1$H NMR (300 MHz, DMSO-d$_6$): δ 0.24-0.28 (2H, m), 0.43-0.47 (2H, m), 1.24-1.29 (1H, m), 4.45 (2H, J=7.2 Hz, d), 7.15-7.19 (2H, m), 7.69-7.74 (2H, m), 7.86 (1H, s), 8.64 (1H, J=5.2 Hz), 12.03 (1H, br). LCMS (mobile phase: 10%-95% Acetonitrile-Water-0.02% NH$_4$Ac): purity >95%, RT=2.741 min. [M+H] Calc'd for $C_{19}H_{15}ClN_4O_2$, 367; Found, 367.

Preparation 10a: 5-Chloro-3-iodo-1-[2-(pyrrolidin-1-yl)ethyl]-1H-indazole

Preparation 10b: 5-Chloro-3-iodo-2-[2-(pyrrolidin-1-yl)ethyl]-2H-indazole

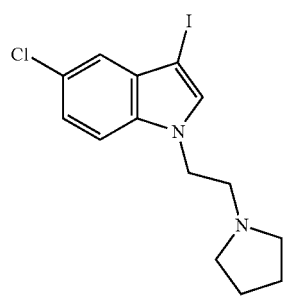

10a

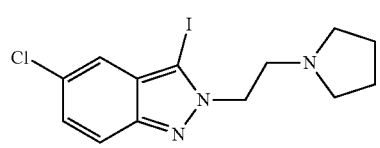

10b

The title compounds were prepared from 1-(2-chloroethyl)pyrrolidine hydrochloride and 5-chloro-3-iodo-1H-indazole according to the procedure for Preparation 8b and 8c. 5-chloro-3-iodo-1-[2-pyrrolidin-1-yl)ethyl]-1H-indazole (39%). [M+H] Calc'd for $C_{13}H_{15}ClIN_3$, 376; Found, 376. 5-chloro-3-iodo-2-[2-(pyrrolidin-1-yl)ethyl]-2H-indazole (21%). [M+H] Calc'd for $C_{13}H_{15}ClIN_3$, 376; Found, 376.

Preparation 10c: Methyl 3-amino-2-(2-{5-chloro-2-[2-(pyrrolidin-1-yl)ethyl]-2H-indazol-3-yl}ethynyl) pyridine-4-carboxylate

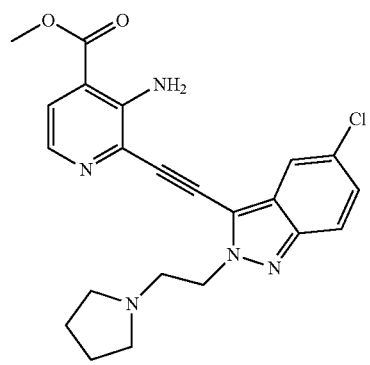 [SMILES: COC(=O)c1ccnc(C#Cc2c3cc(Cl)ccc3nn2CCN2CCCC2)c1N]

The title compound was prepared in 69% yield from Preparation 10b according to the general procedure outline for Preparation 1c. [M+H] Calc'd for $C_{22}H_{22}ClN_5O_2$, 424; Found, 424.

Preparation 10d: Methyl 2-{5-chloro-2-[2-(pyrrolidin-1-yl)ethyl]-2H-indazol-3-yl}-1H-pyrrolo[3,2-b]pyridine-7-carboxylate

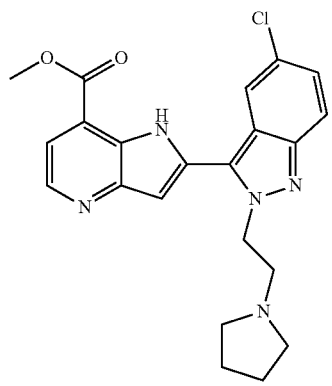 [SMILES: COC(=O)c1ccnc2cc(-c3c4cc(Cl)ccc4nn3CCN3CCCC3)[nH]c12]

The title compound was prepared in 35% yield from Preparation 10c according to the general procedure outline for Preparation 1d. Calc'd for $C_{22}H_{22}ClN_5O_2$, 424; Found, 424.

Example 10: 2-{5-Chloro-2-[2-(pyrrolidin-1-yl)ethyl]-2H-indazol-3-yl}-1H-pyrrolo[3,2-b]pyridine-7-carboxylic Acid

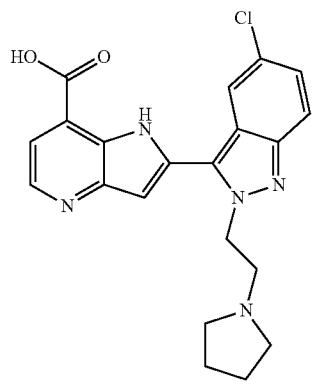 [SMILES: O=C(O)c1ccnc2cc(-c3c4cc(Cl)ccc4nn3CCN3CCCC3)[nH]c12]

The title compound was prepared in 69% yield from Preparation 10d according to the general procedure outline for Example 1. $^1$H NMR (400 MHz, D$_2$O): δ 1.75 (4H, br s), 2.71 (4H, br s), 3.56 (2H, t, J=6.4 Hz), 4.82 (2H, t, J=6.4 Hz), 7.24 (1H, s), 7.37 (1H, dd, J=9.0, 2.0 Hz), 7.67 (1H, d, J=5.1 Hz), 7.75-7.81 (2H, m), 8.60 (1H, d, J=4.8 Hz). [M+H] Calc'd for $C_{21}H_{20}ClN_5O2$, 410; Found, 410.

Preparation 11a: 6-Bromo-3-chloro-2-methyl-2H-indazole

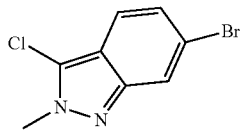

To a solution of 6-bromo-2-methyl-2H-indazole (1.0 g, 4.7 mmol) in AcOH (10 mL) was added SO$_2$Cl$_2$ (0.58 mL, 7.1 mmol). The solution was stirred at rt for 4 h. 2M aq. NaOH (60 mL) was added, and the reaction was extracted with EA (100 mL). Organics were dried over Na$_2$SO$_4$, concentrated, and purified by flash chromatography on silica gel (PE/EA=5/1) to afford 1.1 g (96%) of the title compound as a yellow solid. [M+H] Calc'd for $C_8H_6BrClN_2$, 245; Found, 245.

Preparation 11b: 3-Chloro-N,2-dimethyl-N-phenyl-2H-indazo-6-amine

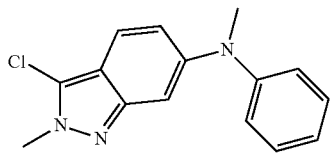 [SMILES: CN(c1ccccc1)c1ccc2c(Cl)n(C)nc2c1]

A mixture of 6-bromo-3-chloro-2-methyl-2H-indazole (1.0 g, 4.10 mmol), N-methyl-aniline (627 mg, 4.10 mmol), Pd$_2$dba$_3$ (73 mg, 0.08 mmol), xantphos (138 mg, 0.24 mmol), and t-BuOK (642 mg, 5.74 mmol) in toluene (50 mL) was purged with nitrogen and stirred at 120° C. overnight. The reaction was filtered and concentrated. Purification by silica gel chromatography (PE/EA=10/1) gave 222 mg (20%) of the title compound as a yellow solid. [M+H] Calc'd for $C_{15}H_{14}ClN_3$, 272; Found, 272.

Preparation 11c: Methyl 3-amino-2-(2-{2-methyl-6-[methyl(phenyl)amino]-2H-indazol-3-yl}ethynyl)pyridine 4-carboxylate

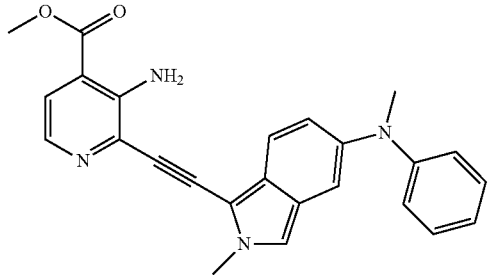 [SMILES: COC(=O)c1ccnc(C#Cc2c3ccc(N(C)c4ccccc4)cc3cn2C)c1N]

A mixture of Preparation 11b (408 mg, 1.50 mmol), methyl 3-amino-2-ethynyl-pyridine-4-carboxylate (264 mg, 1.50 mmol), Pd(ACN)$_2$Cl$_2$ (12 mg, 0.037 mmol), xphos (36 mg, 0.075 mmol), and K$_2$CO$_3$ (828 mg, 6.00 mmol) in acetonitrile (10 mL) was purged with nitrogen and stirred at 110° C. overnight. The reaction was filtered, and the filtrate was concentrated and purified by silica gel chromatography (PE/EA=1/2) to afford 308 mg (50%) of the title compound as a yellow solid. [M+H] Calc'd for $C_{24}H_{21}N_5O_2$, 412; Found, 412.

Preparation 11d: Methyl 2-{2-methyl-6-[methyl(phenyl)amino]-2H-indazol-3-yl}-1H-pyrrolo[3,2-b]pyridine-7-carboxylate

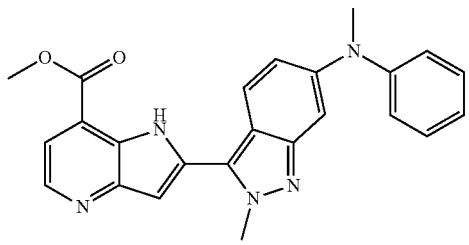 [SMILES: COC(=O)c1ccnc2cc(-c3c4ccc(N(C)c5ccccc5)cc4nn3C)[nH]c12]

The title compound was prepared in 15% yield from Preparation 11c according to the procedure for Preparation 3b. [M+H] Calc'd for $C_{24}H_{21}N_5O_2$, 412; Found, 412.

Example 11: 2-{2-Methyl-6-[methyl(phenyl)amino]-2H-indazol-3-yl}-1-H-pyrrolo[3,2-b]pyridine-7-carboxylic Acid

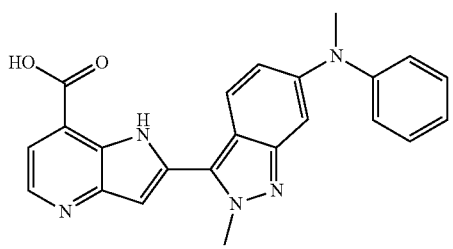 [SMILES: CN(c1ccccc1)c1ccc2c(-c3cc4nccc(C(=O)O)c4[nH]3)n(C)nc2c1]

The title compound was prepared in 87% yield from Preparation 11d according to the general procedure outline for Example 1. $^1$H NMR (300 MHz, DMSO-d$_6$): δ 3.34 (3H, s), 4.21 (3H, s), 6.80-6.84 (1H, m), 6.90-6.95 (1H, m), 6.99-7.02 (2H, m), 7.07 (1H, s), 7.15 (1H, s), 7.24-7.29 (2H, m), 7.56-7.59 (2H, m), 8.50 (1H, J=4.8 Hz, d), 11.52 (1H, s). LCMS (mobile phase: 5%-95% Acetonitrile-Water-0.02% TFA): purity is >95%, Rt=3.449 min. [M+H] Calc'd for $C_{23}H_{19}N_5O_2$, 398; Found, 398.

Preparation 12a: 7-Bromo-3-chloro-2-methyl-2H-indazole

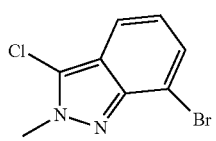

The title compound was prepared in 87% yield from 7-bromo-2-methyl-2H-indazole according to the general procedure for Preparation 11a. [M+H] Calc'd for $C_8H_6BrClN_2$, 245; Found, 245.

Preparation 12b: 3-Chloro-N,2vdimethyl-N-phenyl-2H-indazol-7-amine

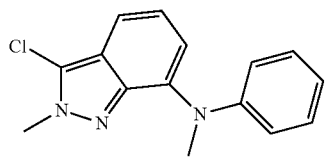 [SMILES: CN(c1ccccc1)c1cccc2c(Cl)n(C)nc12]

The title compound was prepared in 29%0 yield from Preparation 12a according to the general procedure for Preparation 11b. [M+H] Calc'd for $C_{15}H_4ClN_3$, 272; Found, 272.

Preparation 12c: Methyl 3-amino-2-(2-{2-methyl-7-[methyl(phenyl)amino]-2H-indazol-3-yl}ethynyl)pyridine-4-carboxylate

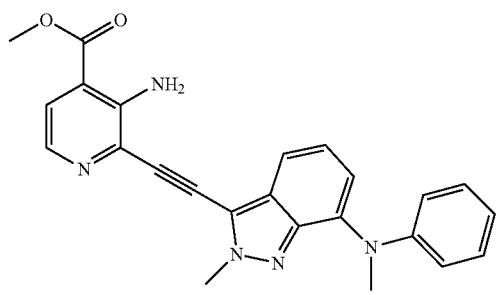 [SMILES: COC(=O)c1ccnc(C#Cc2c3cccc(N(C)c4ccccc4)c3nn2C)c1N]

The title compound was prepared in 37% yield from Preparation 12b according to the general procedure for Preparation 11c. [M+H] Calc'd for $C_{24}H_{21}N_5O_2$, 412; Found, 412.

Preparation 12d: Methyl 2-{2-methyl-7-[methyl(phenyl)amino]-2H-indazol-3-yl}-1H-pyrrolo[3,2-b]pyridine-7-carboxylate

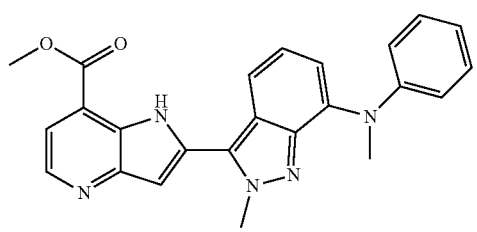 [SMILES: COC(=O)c1ccnc2cc(-c3c4cccc(N(C)c5ccccc5)c4nn3C)[nH]c12]

The title compound was prepared in 20% yield from Preparation 12c according to the procedure for Preparation 3b. [M+H] Calc'd for $C_{24}H_{21}N_5O_2$, 412; Found, 412.

Example 12: 2-{2-Methyl-7-[methyl(phenyl)amino]-2H-indazol-3-yl}-1H-pyrrolo[3,2-b]pyridine-7-carboxylic Acid

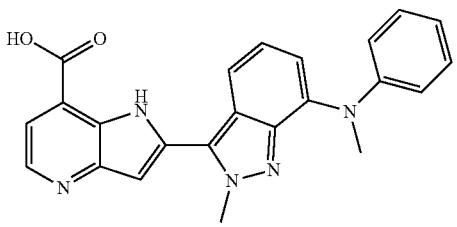 [SMILES: CN(c1ccccc1)c1cccc2c(-c3cc4nccc(C(=O)O)c4[nH]3)n(C)nc12]

The title compound was prepared in 87% yield from Preparation 12d according to the general procedure outline for Example 1. $^1$H NMR (300 MHz, DMSO-$d_6$): δ 3.46 (3H, s), 4.24 (3H, s), 6.77-6.84 (3H, m), 7.04-7.21 (5H, m), 7.54-7.59 (2H, m), 8.51 (1H, J=4.5 Hz, d), 11.56 (1H, s). LCMS (mobile phase: 5%-95% Acetonitrile-Water-0.02% NH$_4$Ac): purity is >95%, RT=3.531 min. [M+H] Calc'd for C$_{23}$H$_{19}$N$_5$O$_2$, 398; Found, 398.

Preparation 13a: Methyl 2-(1-methyl-1H-indazol-3-yl)-1H-pyrrolo[3,2-b]pyridine-7-carboxylate

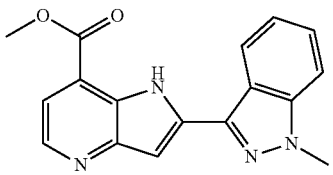

Methyl 3-amino-2-chloropyridine-4-carboxylate (186 mg, 1.0 mmol), 1-(1-methyl-1H-indazol-3-yl)ethanone (348 mg, 2.0 mmol), MgSO$_4$ (120 mg), and acetic acid (85 μL, 1.5 mmol) were combined in DMA (3 mL), and the reaction mixture was purged with nitrogen for 10 min. Pd(PtBu$_3$)$_2$ (50 mg, 0.1 mmol) and K$_3$PO$_4$ (276 mg, 1.3 mmol) were added. The reaction vessel was sealed and heated at 120° C. for 16 hr. The reaction was concentrated and purified by prep-HPLC (20-65% ACN/water with 0.1% formic acid) to give 36 mg (12%) of the title compound. [M+H]Calc'd for C$_{17}$H$_{14}$N$_4$O$_2$, 307; Found, 307.

Example 13: 2-(1-methyl-1H-indazol-3-yl)-1H-pyrrolo[3,2-b]pyridine-7-carboxylic Acid

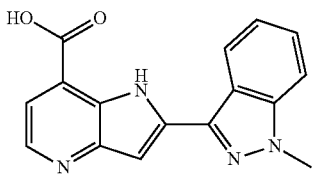

The title compound was prepared in 72% yield from Preparation 13a according to the procedure for Example 1. [M+H] Calc'd for C$_{16}$H$_{12}$N$_4$O$_2$, 293; Found, 293.

Example 14: 2-(5-fluoro-1-methyl-1H-indazol-3-yl)-1H-pyrrolo[3,2-b]pyridine-7-carboxylic Acid

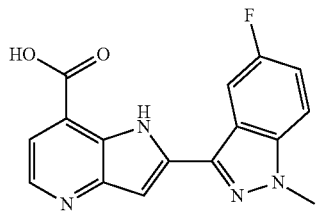 [SMILES: Cn1nc(-c2cc3nccc(C(=O)O)c3[nH]2)c2cc(F)ccc21]

The title compound was prepared in <10% overall yield starting from 5-fluoro-3-iodo-1-methyl-1H-indazole according to the procedure sequence for the preparation of Example 1 (Preparation 1c, Preparation 1d, Example 1). $^1$H NMR (400 MHz, DMSO-$d_6$): δ 4.19 (3H, s), 7.35-7.45 (3H, m), 7.80 (1H, dd, J=9.1, 4.2 Hz), 8.04 (1H, d, J=9.2 Hz), 8.25-8.32 (2H, m), 11.05 (1H, s). LCMS (mobile phase: 5%-95% Acetonitrile-Water-0.02% TFA): purity >95%, RT=2.853 min. [M+H] Calc'd for Cl$_6$H$_{11}$FN$_4$O$_2$, 311; Found, 311.

Preparation 15a:
6-Chloro-3-iodo-1-methyl-1H-indazole

Preparation 15b:
6-Chloro-3-iodo-2-methyl-2H-indazole

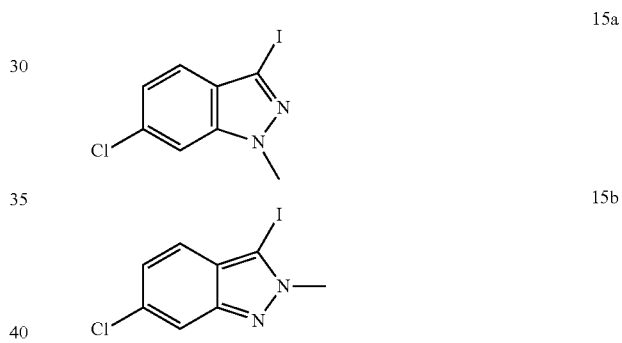

The title compounds were prepared from iodomethane and 6-chloro-3-iodo-1H-indazole according to the procedure for Preparation 8b and 8c. 6-chloro-3-iodo-1-methyl-1H-indazole: (610%). [M+H] Calc'd for C$_8$H$_6$ClIN$_2$, 293; Found, 293. 6-chloro-3-iodo-2-methyl-2H-indazole: (22%). [M+H] Calc'd for C$_8$H$_6$ClIN$_2$, 293; Found, 293.

Preparation 15c: Methyl 3-amino-2-[2-(6-chloro-1-methyl-1H-indazol-3-yl) ethynyl]pyridine-4-carboxylate

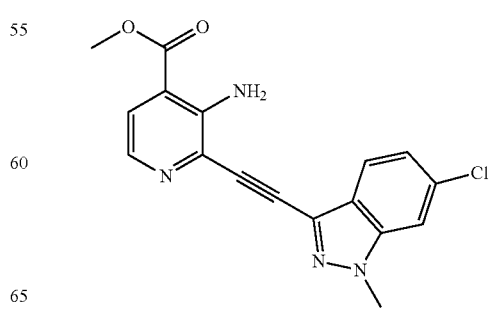

The title compound was prepared in 96% yield from Preparation 15a according to the general procedure outline for Preparation 1c. [M+H] Calc'd for $C_{17}H_{13}ClN_4O_2$, 341; Found, 341.

Preparation 15d: Methyl 2-(6-chloro-1-methyl-1H-indazol-3-yl)-1H-pyrrolo[3,2-b]pyridine-7-carboxylate

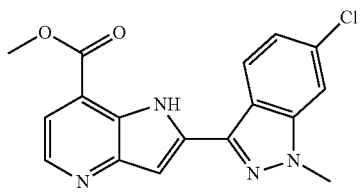 [SMILES: COC(=O)c1ccnc2cc(-c3nn(C)c4cc(Cl)ccc34)[nH]c12]

The title compound was prepared in 6% yield from Preparation 15c according to the general procedure outline for Preparation 1d. $^1$H NMR (400 MHz, MeOD-d$_4$): δ 4.20 (3H, s), 4.24 (3H, s), 7.40-7.46 (2H, m), 7.85 (1H, s), 8.03 (1H, J=5.6 Hz, d), 8.16 (1H, J=8.8 Hz, d), 8.64 (1H, J=5.6 Hz, d). LCMS (mobile phase: 5%-95% Acetonitrile-Water-0.02% NH$_4$Ac): purity >95%, RT=4.388 min. [M+H] Calc'd for $C_{17}H_{13}ClN_4O_2$, 341; Found, 341.

Example 15: 2-(6-Chloro-1-methyl-1H-indazol-3-yl)-1H-pyrrolo[3,2-b]pyridine-7-carboxylic Acid

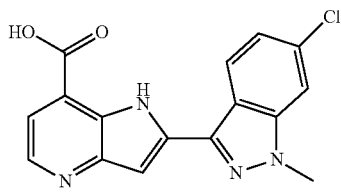 [SMILES: Cn1nc(-c2cc3nccc(C(=O)O)c3[nH]2)c2ccc(Cl)cc21]

The title compound was prepared in 67% yield from Preparation 16d according to the general procedure outline for Example 1. 1H NMR (400 MHz, DMSO-d$_6$): δ 4.18 (3H, s), 7.31-7.34 (1H, m), 7.48-7.50 (1H, m), 7.61-7.63 (1H, m), 7.98-8.00 (1H, m), 8.31-8.33 (1H, m), 8.53-8.55 (1H, m), 10.49 (1H, br s). LCMS (mobile phase: 10%-95% Acetonitrile-Water-0.02% NH$_4$Ac): purity is >95%, Rt=2.952 min. [M+H] Calc'd for $C_{16}H_{11}ClN_4O_2$, 327; Found, 327.

Preparation 16a:
6-Fluoro-3-iodo-1-methyl-1H-indazole

Preparation 16b:
6-Fluoro-3-iodo-2-methyl-2H-indazole

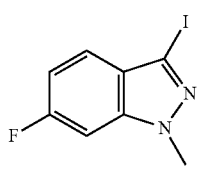
16a

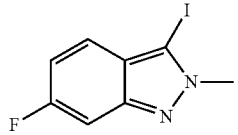
16b

The title compounds were prepared from iodomethane and 6-fluoro-3-iodo-1H-indazole according to the procedure for Preparation 8b and 8c. 6-fluoro-3-iodo-1-methyl-1H-indazole: (61%). [M+H] Calc'd for $C_8H_6FIN_2$, 277; Found, 277. 6-fluoro-3-iodo-2-methyl-2H-indazole: (20%). [M+H] Calc'd for $C_8H_6FIN_2$, 277; Found, 277.

Preparation 16c: Methyl 3-amino-2-[2-(6-fluoro-1-methyl-1H-indazol-3-yl)ethynyl]pyridine-4-carboxylate

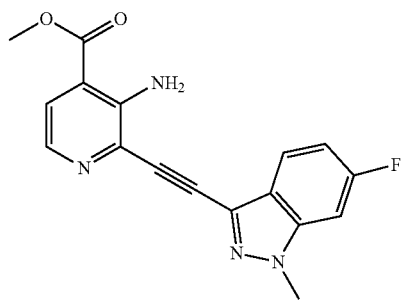 [SMILES: COC(=O)c1ccnc(C#Cc2nn(C)c3cc(F)ccc23)c1N]

The title compound was prepared in 900/% yield from Preparation 16a according to the general procedure outline for Preparation 1c. [M+H] Calc'd for $C_{17}H_{13}FN_4O_2$, 325; Found, 325.

Preparation 16d: Methyl 2-(6-fluoro-1-methyl-1H-indazol-3-yl)-1H-pyrrolo[3,2-b]pyridine-7-carboxylate

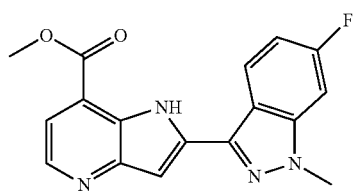 [SMILES: COC(=O)c1ccnc2cc(-c3nn(C)c4cc(F)ccc34)[nH]c12]

The title compound was prepared in 8% yield from Preparation 16c according to the general procedure outline for Preparation 1d. $^1$H NMR (400 MHz, DMSO-d$_6$): δ 4.03 (3H, s), 4.16 (3H, s), 7.18-7.21 (1H, m), 7.61-7.70 (2H, m), 8.29-8.33 (1H, m), 8.55-8.58 (1H, m), 10.75 (1H, s). LCMS (mobile phase: 5%-95% Acetonitrile-Water-0.02% NH$_4$Ac): purity >95%, RT=4.150 min. [M+H] Calc'd for $C_{17}H_{13}FN_4O_2$, 325; Found, 325.

Example 16: 2-(6-Fluoro-1-methyl-1H-indazol-3-yl)-1H-pyrrolo[3,2-b]pyridine-7-carboxylic Acid

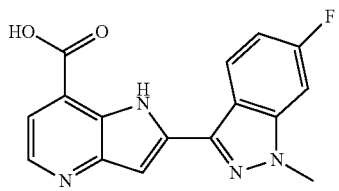 [SMILES: Cn1nc(-c2cc3nccc(C(=O)O)c3[nH]2)c2ccc(F)cc21]

The title compound was prepared in 67% yield from Preparation 16d according to the general procedure outline for Example 1. $^1$H NMR (400 MHz, DMSO-d$_6$): δ 4.15 (3H, s), 7.19-7.21 (1H, m), 7.50 (1H, s), 7.59 (1H, J=4.0 Hz, d), 7.68 (1H, J=10.4 Hz, d), 8.33-8.36 (1H, m), 8.53 (1H, J=4.8 Hz, d), 10.42 (1H, br s). LCMS (mobile phase: 10%-95% Acetonitrile-Water-0.02% NH$_4$Ac): purity >95%, RT=2.809 min. [M+H] Calc'd for C$_{16}$H$_{11}$FN$_4$O$_2$, 311; Found, 311.

Preparation 17a: Methyl 3-amino-2-[2-(6-chloro-1-ethyl-1H-indazol-3-yl)ethynyl]pyridine-4-carboxylate

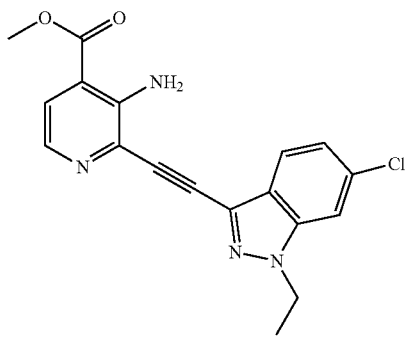 [SMILES: CCn1nc(C#Cc2nccc(C(=O)OC)c2N)c2ccc(Cl)cc21]

The title compound was prepared in 45% yield from Preparation 8b according to the general procedure outline for Preparation 1c. [M+H] Calc'd for C$_{18}$H$_{15}$ClN$_4$O$_2$, 355; Found, 355.

Preparation 17b: Methyl 2-(6-chloro-1-ethyl-1H-indazol-3-yl)-1H-pyrrolo[3,2-b]pyridine-7-carboxylate

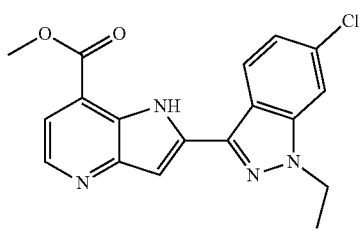 [SMILES: CCn1nc(-c2cc3nccc(C(=O)OC)c3[nH]2)c2ccc(Cl)cc21]

The title compound was prepared in 13% yield from Preparation 17a according to the general procedure outline for Preparation 1d. $^1$H NMR (400 MHz, MeOD-d$_4$): δ 1.62 (3H, J=7.2 Hz, t), 4.18 (3H, s), 4.61-4.63 (2H, m), 7.39-7.41 (2H, m), 7.85 (1H, s), 7.98 (H, J=5.6 Hz, d), 8.12 (1H, J=4.8 Hz, d), 8.61 (1H, J=5.6 Hz, d). LCMS (mobile phase: 5%-95% Acetonitrile-Water-0.02% NH$_4$Ac): purity is >95%, Rt=4.628 min. [M+H] Calc'd for C$_{18}$H$_{15}$ClN$_4$O$_2$, 355; Found, 355.

Example 17: 2-(6-Chloro-1-ethyl-1H-indazol-3-yl)-1H-pyrrolo[3,2-b]pyridine-7-carboxylic acid

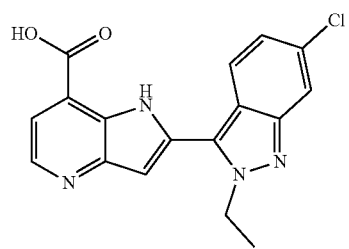 [SMILES: CCn1nc2cc(Cl)ccc2c1-c1cc2nccc(C(=O)O)c2[nH]1]

The title compound was prepared in 71% yield from Preparation 17b according to the general procedure outline for Example 1. $^1$H NMR (400 MHz, DMSO-d$_6$): δ 1.48 (3H, J=6.8 Hz, t), 4.59-4.60 (2H, m), 7.34 (1H, J=8.4 Hz, d), 7.50 (1H, s), 7.66 (1H, J=4.4 Hz, d), 8.05 (1H, s), 8.31 (1H, J=8.8 Hz, d), 8.57 (1H, J=4.4 Hz, d), 10.66 (1H, br s). LCMS (mobile phase: 5%-95% Acetonitrile-Water-0.02% NH$_4$Ac): purity >95%, RT=3.115 min. [M+H] Calc'd for C$_{17}$H$_{13}$ClN$_4$O$_2$, 341; Found, 341.

Preparation 18a: Methyl 3-amino-2-{2-[6-chloro-1-(cyclopropylmethyl)-1H-indazol-3-yl]ethynyl}pyridine-4-carboxylate

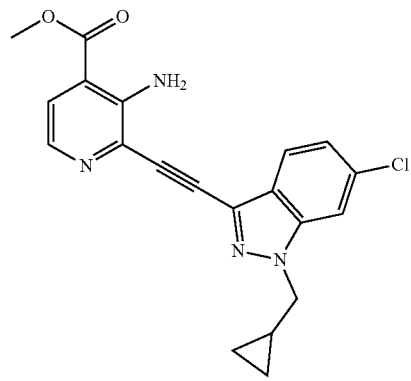 [SMILES: COC(=O)c1ccnc(C#Cc2nn(CC3CC3)c3cc(Cl)ccc23)c1N]

The title compound was prepared in 90% yield from Preparation 9a according to the general procedure outline for Preparation 1c. [M+H] Calc'd for C$_{20}$H$_{17}$ClN$_4$O$_2$, 381; Found, 381.

Preparation 18b: Methyl 2-[6-chloro-1-(cyclopropylmethyl)-1H-indazol-3-yl]-1H-pyrrolo[3,2-b]pyridine-7-carboxylate

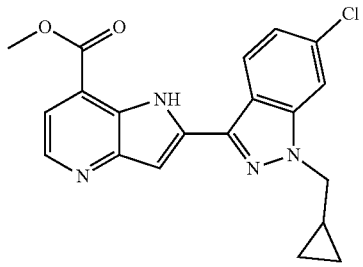 [SMILES: COC(=O)c1ccnc2cc(-c3nn(CC4CC4)c4cc(Cl)ccc34)[nH]c12]

The title compound was prepared in 16% yield from Preparation 18a according to the general procedure outline for Preparation 1d. $^1$H NMR (400 MHz, MeOD-d$_4$): δ 0.52-0.56 (2H, m), 0.64-0.68 (2H, m), 1.46-1.48 (1H, m), 4.11 (3H, s), 4.40 (2H, J=7.2 Hz, d), 7.28 (1H, s), 7.31-7.33 (1H, m), 7.71-7.77 (2H, m), 8.12 (1H, J=8.4 Hz, d), 8.48 (1H, J=5.2 Hz, d). LCMS (mobile phase: 5%-95% Acetonitrile-Water-0.02% NH$_4$Ac): purity >95%, RT=4.848 min. [M+H] Calc'd for C$_{20}$H$_{17}$ClN$_4$O$_2$, 381; Found, 381.

Example 18: 2-[6-Chloro-1-(cyclopropylmethyl)-1H-indazol-3-yl]-1H-pyrrolo[3,2-b]pyridine-7-carboxylic Acid

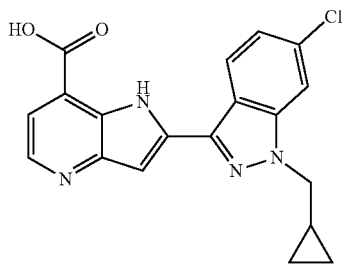 [SMILES: O=C(O)c1ccnc2cc(-c3nn(CC4CC4)c4cc(Cl)ccc34)[nH]c12]

The title compound was prepared in 60% yield from Preparation 18b according to the general procedure outline for Example 1. $^1$H NMR (300 MHz, DMSO-d$_6$): δ 0.47-0.54 (4H, m), 1.38-1.42 (1H, m), 4.46 (2H, J=6.8 Hz, d), 7.31-7.34 (1H, m), 7.50 (1H, s), 7.60 (1H, J=4.8 Hz, d), 8.08 (1H, s), 8.33 (1H, J=8.8 Hz, d), 8.54 (1H, J=4.8 Hz, d), 10.45 (1H, br s). LCMS (mobile phase: 10%-95% Acetonitrile-Water-0.02%/NH$_4$Ac): purity >95%, RT=3.209 min. [M+H] Calc'd for C$_{19}$H$_{15}$ClN$_4$O$_2$, 367; Found, 367.

Preparation 19a: 6-Chloro-3-iodo-1-(2,2,2-trifluoroethyl)-1H-indazole

Preparation 19b: 6-Chloro-3-iodo-2-(2,2,2-trifluoroethyl)-2H-indazole

19a

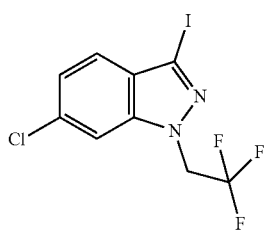

19b

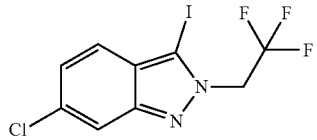

The title compounds were prepared from 1,1,1-trifluoro-2-iodoethane and 6-chloro-3-iodo-1H-indazole according to the procedure for Preparation 8b and 8c. 6-chloro-3-iodo-1-(2,2,2-trifluoroethyl)-1H-indazole: (60%). [M+H] Calc'd for C$_9$H$_5$ClF$_3$IN$_2$, 361; Found, 361. 6-chloro-3-iodo-2-(2,2,2-trifluoroethyl)-2H-indazole: (20%). [M+H] Calc'd for C$_9$H$_5$ClF$_3$IN$_2$, 361; Found, 361.

Preparation 19c: Methyl 3-amino-2-{2-[6-chloro-1-(2,2,2-trifluoroethyl)-1H-indazol-3-yl]ethynyl}pyridine-4-carboxylat

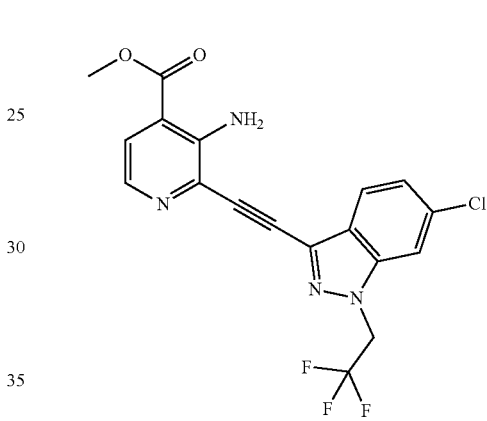

The title compound was prepared in 78% yield from Preparation 19a according to the general procedure outline for Preparation 1c. [M+H] Calc'd for C$_{18}$H$_2$ClF$_3$N$_4$O$_2$, 409; Found, 409.

Preparation 19d: Methyl 2-[6-chloro-1-(2,2,2-trifluoroethyl)-1H-indazol-3-yl]-1H-pyrrolo[3,2-b]pyridine-7-carboxylate

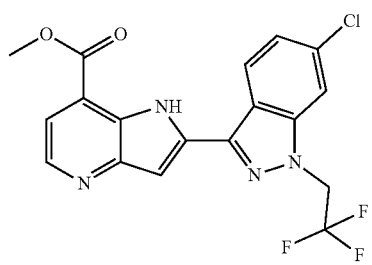 [SMILES: COC(=O)c1ccnc2cc(-c3nn(CC(F)(F)F)c4cc(Cl)ccc34)[nH]c12]

The title compound was prepared in 13% yield from Preparation 19c according to the general procedure outline for Preparation 1d. $^1$H NMR (400 MHz, MeOD-d$_4$): δ 4.11 (3H, s), 5.34-5.41 (2H, m), 7.35 (s, 1H), 7.39-7.41 (1H, m), 7.74 (1H, J=5.2 Hz, d), 7.85 (1H, s), 8.17 (1H, J=8.8 Hz, d), 8.51 (1H, J=5.2 Hz, d). LCMS (mobile phase: 5%-95% Acetonitrile-Water-0.02% NH$_4$Ac): purity >95%, RT=4.583 min. [M+H] Calc'd for C$_{18}$H$_{12}$ClF$_3$N$_4$O$_2$, 409; Found, 409.

Example 19: 2-[6-Chloro-1-(2,2,2-trifluoroethyl)-1H-indazol-3-yl]-1H-pyrrolo[3,2-b]pyridine-7-carboxylic Acid

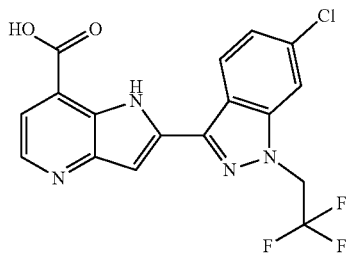 [SMILES: O=C(O)c1ccnc2cc(-c3nn(CC(F)(F)F)c4cc(Cl)ccc34)[nH]c12]

The title compound was prepared in 74% yield from Preparation 19d according to the general procedure outline for Example 1. $^1$H NMR (300 MHz, DMSO-$d_6$): δ 5.64-5.67 (2H, m), 7.41-7.43 (1H, m), 7.59-7.64 (2H, m), 8.17 (1H, s), 8.39 (1H, J=8.4 Hz, d), 8.57 (1H, J=4.8 Hz, d), 10.46 (1H, br s). LCMS (mobile phase: 10%-95% Acetonitrile-Water-0.02% NH$_4$Ac): purity >95%, RT=3.231 min. [M+H] Calc'd for $C_{17}H_{10}ClF_3N_4O_2$, 395; Found, 395.

Preparation 20a: Methyl 3-amino-2-2-{5-chloro-1-[2-(pyrrolidin-1-yl)ethyl]-1H-indazol-3-yl}ethynyl)pyridine-4-carboxylate

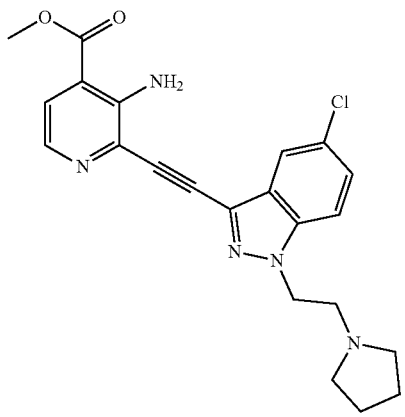 [SMILES: COC(=O)c1ccnc(C#Cc2nn(CCN3CCCC3)c3ccc(Cl)cc23)c1N]

The title compound was prepared in 65% yield from Preparation 10a according to the general procedure outline for Preparation 1c. [M+H] Calc'd for $C_{22}H_{22}ClNSO_2$, 424; Found, 424.

Preparation 20b: Methyl 2-{5-chloro-1-[2-(pyrrolidin-1-)ethyl]-1H-indazol-3-yl}-1H-pyrrolo[3,2-b]pyridine-7-carboxylate

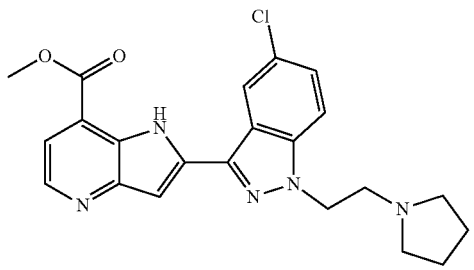 [SMILES: COC(=O)c1ccnc2cc(-c3nn(CCN4CCCC4)c4ccc(Cl)cc34)[nH]c12]

The title compound was prepared in 39% yield from Preparation 20a according to the general procedure outline for Preparation 1d. Calc'd for $C_{22}H_{22}ClN_5O_2$, 424; Found, 424.

Example 20: 2-{5-Chloro-1-[2-(pyrrolidin-1-yl)ethyl]-1H-indazol-3-yl}-1H-pyrrolo[3,2-b]pyridine-7-carboxylic Acid

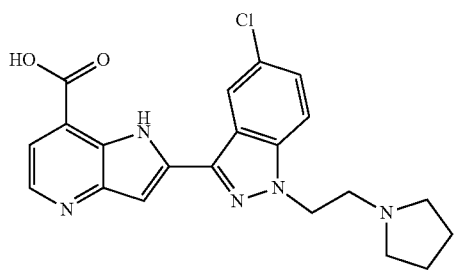 [SMILES: O=C(O)c1ccnc2cc(-c3nn(CCN4CCCC4)c4ccc(Cl)cc34)[nH]c12]

The title compound was prepared in 66% yield from Preparation 20b according to the general procedure outline for Example 1. $^1$H NMR (400 MHz, DMSO-$d_6$): δ 1.91 (4H, br s), 2.67 (4H, br s), 3.62-3.77 (2H, m), 4.91 (2H, t, J=6.4 Hz), 7.56-7.65 (3H, m), 7.94 (1H, d, J=8.8 Hz), 8.42 (1H, s), 8.53 (1H, d, J=4.8 Hz), 10.54 (1H, s). [M+H] Calc'd for $C_{21}H_{20}ClN_5O_2$, 410; Found, 410.

Preparation 21a: Methyl 3-amino-2-(2-{5-fluoro-1-[2-(morpholin-4-yl)ethyl]-1H-indazol-3-yl}ethynyl)pyridine-4-carboxylate

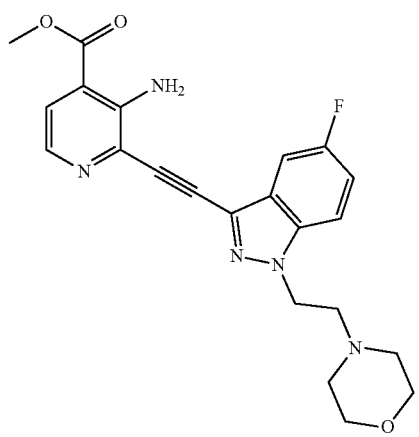 [SMILES: COC(=O)c1ccnc(C#Cc2nn(CCN3CCOCC3)c3ccc(F)cc23)c1N]

The title compound was prepared in 59% yield from 5-fluoro-3-iodo-1-[2-(morpholin-4-yl)ethyl]-1H-indazole (See US Patent Application Publication 2014/171432) according to the general procedure outline for Preparation 1c. [M+H] Calc'd for $C_{22}H_{22}FN_5O_3$, 424; Found, 424.

Preparation 21b: Methyl 2-{5-fluoro-1-[2-(morpholin-4-yl)ethyl]-1H-indazol-3-yl}-1H-pyrrolo[3,2-b]pyridine-7-carboxylate

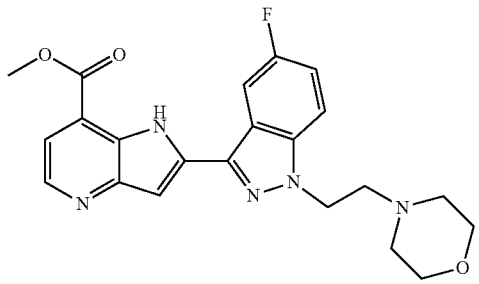 [SMILES: COC(=O)c1ccnc2cc(-c3nn(CCN4CCOCC4)c4ccc(F)cc34)[nH]c12]

The title compound was prepared in 30% yield from Preparation 21a according to the general procedure outline for Preparation 1d. Calc'd for $C_{22}H_{22}FN_5O_3$, 424; Found, 424.

Example 21: 2-{5-Fluoro-1-[2-(morpholin-4-yl)ethyl]-1H-indazol-3-yl}-1H-pyrrolo[3,2-b]pyridine-7-carboxylic Acid

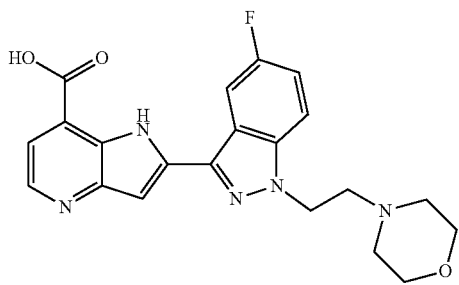 [SMILES: O=C(O)c1ccnc2cc(-c3nn(CCN4CCOCC4)c4ccc(F)cc34)[nH]c12]

The title compound was prepared in 68% yield from Preparation 21b according to the general procedure outline for Example 1. $^1$H NMR (400 MHz, DMSO-$d_6$): δ 2.67 (4H, br s), 3.02 (2H, br s), 3.59 (4H, br s), 4.76 (2H, br s), 7.46 (1H, t, J=8.9 Hz), 7.55 (1H, s), 7.61 (1H, s), 7.93 (1H, dd, J=9.2, 4.0 Hz), 8.12 (1H, d, J=8.9 Hz), 8.56 (1H, s). [M+H] Calc'd for $C_{21}H_{20}2FN_5O_3$, 410; Found, 410.

II. Biological Evaluation

Example 1: In Vitro Enzyme Inhibition Assay

JMJD2C Assay: This assay determines the ability of a test compound to inhibit JMJD2C demethylase activity. Baculovirus expressed JMIJD2C (GenBank Accession #BC143571, AA 2-372) was purchased from BPS Bioscience (Cat#50105).

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 µL of the mixture of 900 nM H3K9me3-biotin labeled peptide and 6 µM alpha-ketoglutaric acid with 2 µL of 11-point serial diluted inhibitor in 3% DMSO were added to each well of the plate, followed by the addition of 2 µl of 0.9 nM JMJD2C to initiate the reaction. The reaction mixture was incubated at room temperature for 30 min, and terminated by the addition of 6 µL of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hr incubation at room temp. A ratio was calculated (665/615) for each well and fitted to determine inhibition constant ($IC_{50}$).

The ability of the pyridine compounds disclosed herein to inhibit demethylase activity was quantified and the respective $IC_{50}$ value was determined. Table 3 provides the $IC_{50}$ values of various compounds disclosed herein.

The ability of the compounds disclosed herein to inhibit demethylase activity was quantified and the respective $IC_{50}$ value was determined. Table 3 provides the $IC_{50}$ values of various compounds disclosed herein.

TABLE 3

| Chemical Synthesis Example | Name | JMJD2C $IC_{50}$ (µM) |
|---|---|---|
| 1 | 2-(6-methoxy-2-methyl-2H-indazol-3-yl)-1H-pyrrolo[3,2-b]pyridine-7-carboxylic acid | B |
| 2 | 2-(5-methoxy-2-methyl-2H-indazol-3vyl)-1H-pyrrolo[3,2-b]pyridine-7-carboxylic acid | B |
| 3 | 2-(6-chloro-2-methyl-2H-indazol-3-yl)-1H-pyrrolo[3,2-b]pyridine-7-carboxylic acid | B |
| 4 | 2-[2-methyl-5-(trifluoromethyl)-2H-indazol-3-yl]-lH-pyrrolo[3,2-b]pyridine-7-carboxylic acid | C |
| 5 | 2-[2-methyl-5-(trifluoromethoxy)-2H-indazol-3-yl]-1H-pyrrolo[3,2-b]pyridine-7-carboxylic acid | C |
| 6 | 2-(5-cyclopropyl-2-methyl-2H-indazol-3-yl)-1H-pyrrolo[3,2-b]pyridine-7-carboxylic acid | B |
| 7 | 2-(5-chloro-2-methyl-2H-indazol-3-yl)-1H-pyrrolo[3,2-b]pyridine-7-carboxylic acid | C |
| 8 | 2-(6-chloro-2-ethyl-2H-indazol-3-yl)-1H-pyrrolo[3,2-b]pyridine-7-carboxylic acid | C |

TABLE 3-continued

| Chemical Synthesis Example | Name | JMJD2C IC$_{50}$ (µM) |
|---|---|---|
| 9 | 2-[6-chloro-2-(cyclopropylmethyl)-2H-indazol-3-yl]-1H-pyrrolo[3,2-b]pyridine-7-carboxylic acid | C |
| 10 | 2-{5-chloro-2-[2-(pyrrolidin-1-yl)ethyl]-2H-indazol-3-yl}-1H-pyrrolo[3,2-b]pyridine-7-carboxylic acid | B |
| 11 | 2-{2-methyl-6-[methyl(phenyl)amino]-2H-indazol-3-yl}-1H-pyrrolo[3,2-b]pyridine-7-carboxylic acid | B |
| 12 | 2-{2-methyl-7-[methyl(phenyl)amino]-2H-indazol-3-yl}-1H-pyrrolo[3,2-b]pyridine-7-carboxylic acid | C |
| 13 | 2-(1-methyl-1H-indazol-3-yl)-1H-pyrrolo[3,2-b]pyridine-7-carboxylic acid | B |
| 14 | 2-(5-fluoro-1-methyl-1H-indazol-3-yl)-1H-pyrrolo[3,2-b]pyridine-7-carboxylic acid | B |
| 15 | 2-(6-chloro-1-methyl-1H-indazol-3-yl)-1H-pyrrolo[3,2-b]pyridine-7-carboxylic acid | B |
| 16 | 2-(6-fluoro-1-methyl-1H-indazol-3-yl)-1H-pyrrolo[3,2-b]pyridine-7-carboxylic acid | B |
| 17 | 2-(6-chloro-1-ethyl-1H-indazol-3-yl)-1H-pyrrolo[3,2-b]pyridine-7-carboxylic acid | C |
| 18 | 2-[6-chloro-1-(cyclopropylmethyl)-1H-indazol-3-yl]-1H-pyrrolo[3,2-b]pyridine-7-carboxylic acid | C |
| 19 | 2-[6-chloro-1-(2,2,2-trifluoroethyl)-1H-indazol-3-yl]-1H-pyrrolo[3,2-b]pyridine-7-carboxylic acid | C |
| 20 | 2-{5-chloro-1-[2-(pyrrolidin-1-yl)ethyl]-1H-indazol-3-yl}-1H-pyrrolo[3,2-b]pyridine-7-carboxylic acid | B |
| 21 | 2-{5-fluoro-1-[2-(morpholin-4-yl)ethyl]-1H-indazol-3-yl}-1H-pyrrolo[3,2-b]pyridine-7-carboxylic acid | C |

Note:
Biochemical assay IC$_{50}$ data are designated within the following ranges:
A: ≤0.10 µM;
B: >0.10 µM to ≤1.0 µM;
C: >1.0 uM to ≤10 µM;
D: >10 µM Example 2: In Vitro Cell-Based Assay The primary cellular assay for JMJD2C inhibition is an assay which measures cellular proliferation via Bromodeoxyuridine (BrdU) incorporation after 168 hr of compound incubation. Cell lines tested include the JMJD2C gene amplified cell line KYSE-150. This is a quantitative ELISA assay measuring DNA incorporation of BrdU during S-phase as a direct readout of cellular proliferation.

Assay Principle: This is a colorimetric immunoassay for the quantification of cell proliferation. Cells treated for 168 hours with test compounds are assayed for their ability to go through S-phase as a measure of their proliferative potential.

Assay Method: The human KYSE-150 (SMAD4 mut, TP53 mut) esophageal carcinoma cell line was seeded at 2,000 cells/well on a 96-well tissue culture treated plate. After an overnight incubation, cells were treated with compound in an 1-point dilution series with final concentrations ranging from 100 µM to 2 nM. Cells were then incubated in the presence of compound for 168 hr. After compound incubation the cells were assayed using a BrdU Cell Proliferation ELISA (Roche). The cells were first incubated with BrdU labeling reagent for 2 hr. After 2 hr, the BrdU incorporated cells were fixed and denatured, probed with an anti-BrdU-Peroxidase antibody for 1.5 hr and washed. Finally, a tetramethylbenzidine peroxidase substrate was added to each well for 15 min followed by a $H_2SO_4$ stop solution. The plate was read at 450 nm, and the raw optical density data was transferred into XLFit (IDBS) for IC50 calculation using the formula:

$$\text{fit} = (D + ((V\max * (x^\wedge n))/((x^\wedge n) + (Km^\wedge n))))$$

Table 4 provides the cellular IC$_{50}$ values of various compounds disclosed herein.

TABLE 4

| Example | Cellular IC$_{50}$ (µM) |
|---|---|
| 10d | D |
| 11 | A |
| 16 | D |

Note:
Cellular assay IC$_{50}$ data are designated within the following ranges:
A: ≤0.10 µM;
B: >0.10 µM to ≤1.0 µM;
C: >1.0 µM to ≤10 µM;
D: >10 µM Example 3: In Vivo Xenograph Study Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 500/% RPMI (serum free) and 50% Matrigel at 1×107 cells/mL. MCF-7 cells are subcutaneously injected (100 µL/animal) on the right flank 2-3 days post pellet implantation and tumor volume (length×width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1: Oral Tablet

A tablet is prepared by mixing 48% by weight of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or a pharmaceutically acceptable salt thereof, chosen from:

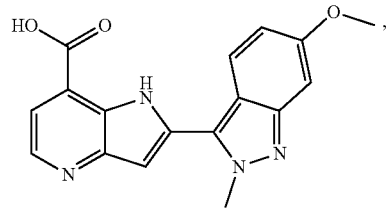,

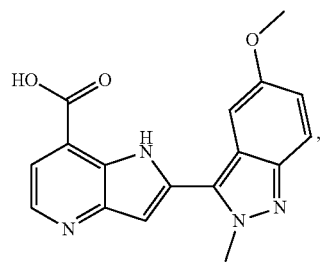,

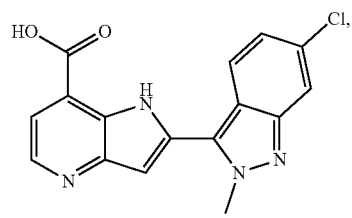,

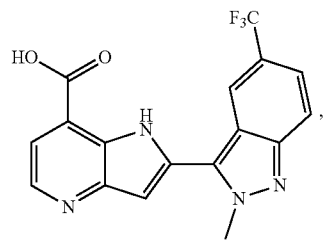,

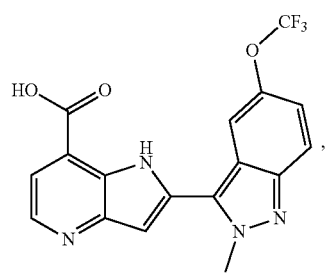,

-continued

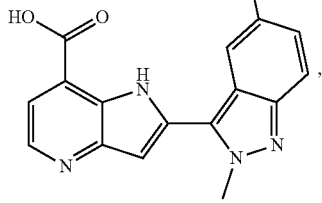,

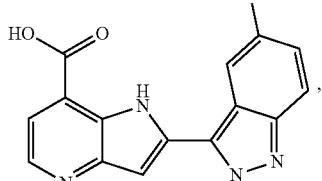,

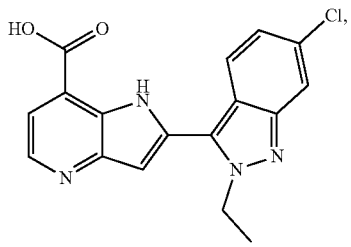,

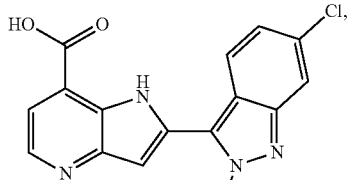,

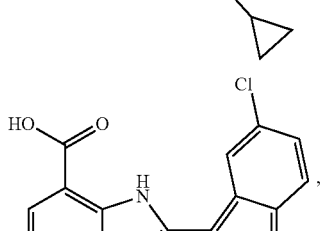,

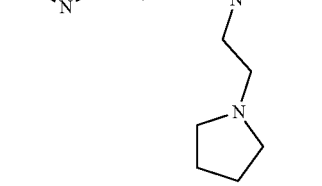,

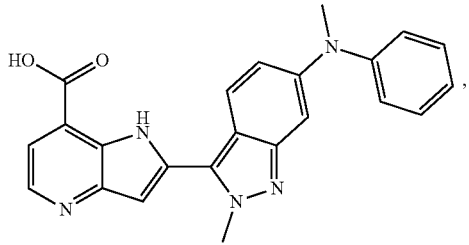,

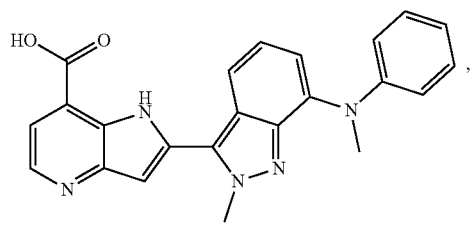
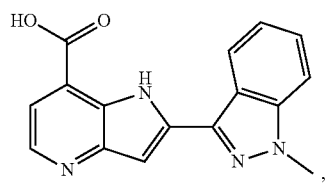
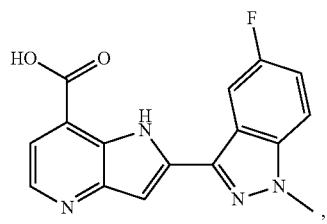
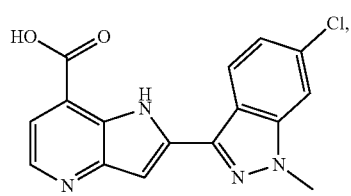
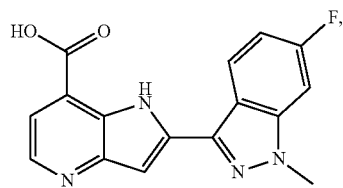
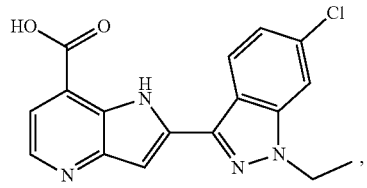
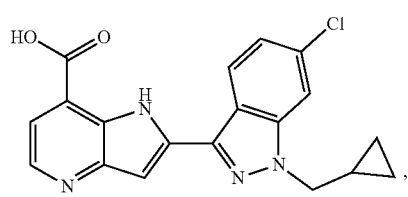
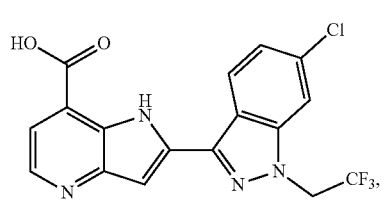
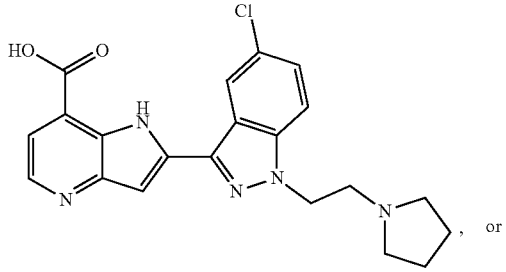
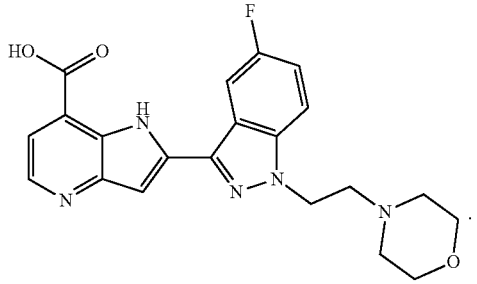
2. A pharmaceutical composition comprising the compound of claim 1 and at least one pharmaceutically acceptable excipient.
3. A compound, or a pharmaceutically acceptable salt thereof, chosen from:
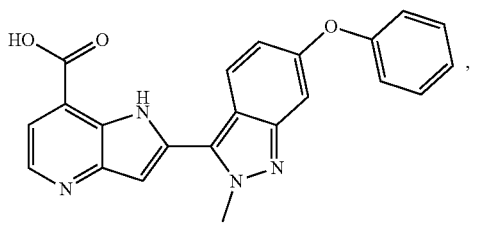
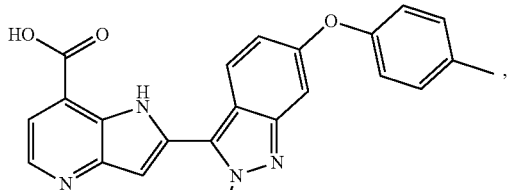
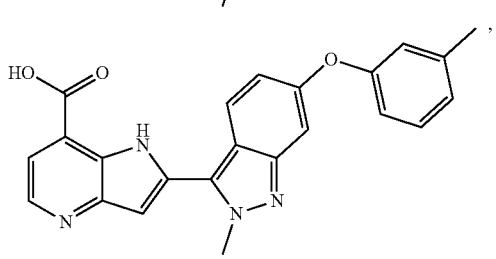
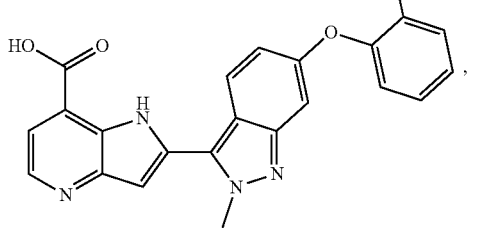

93
-continued
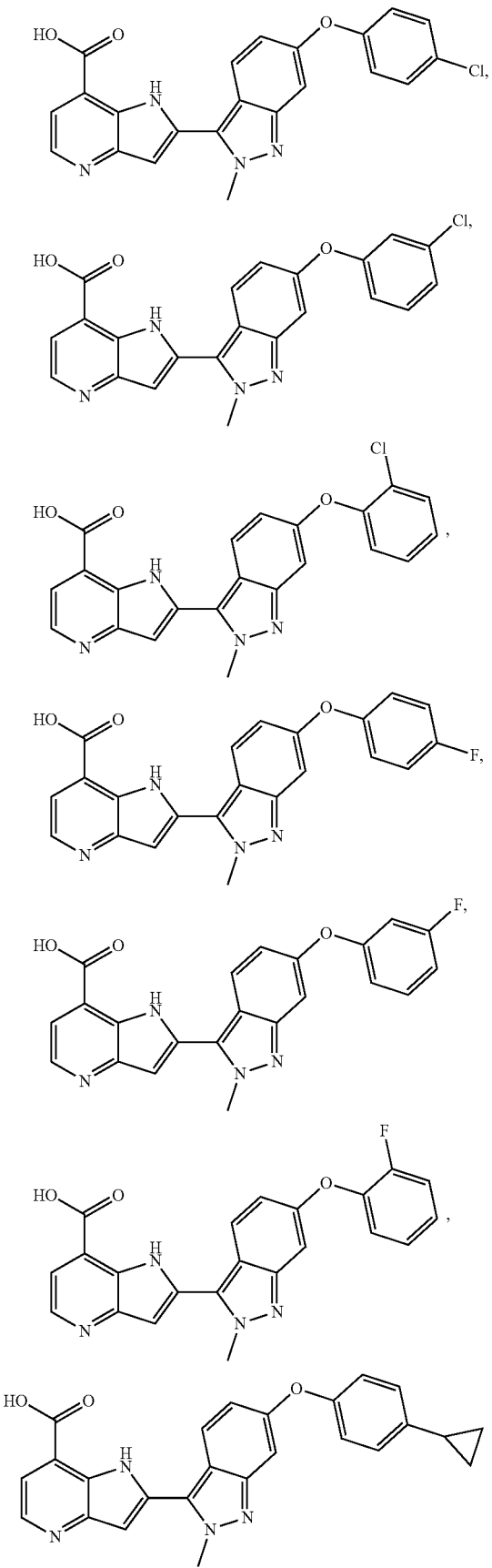
94
-continued
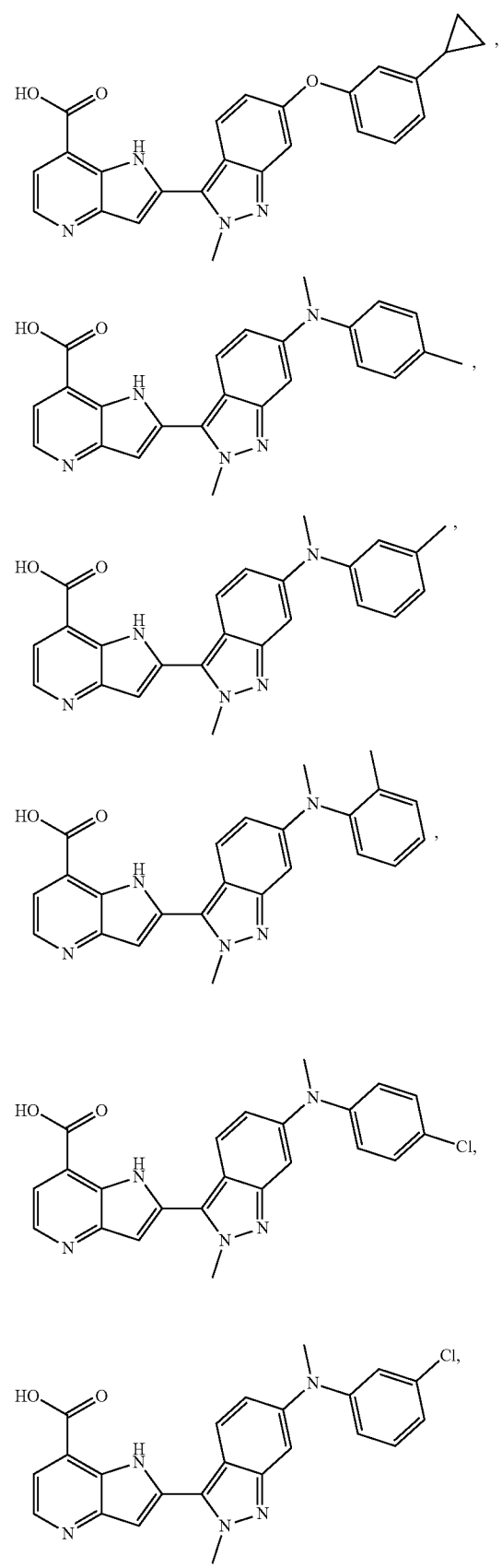

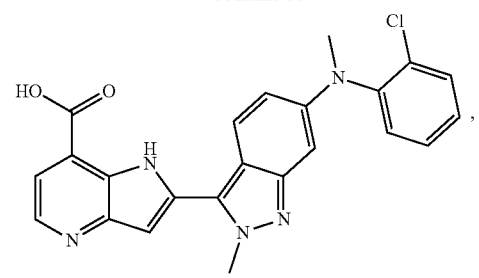
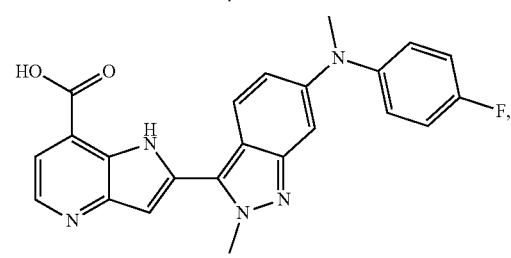
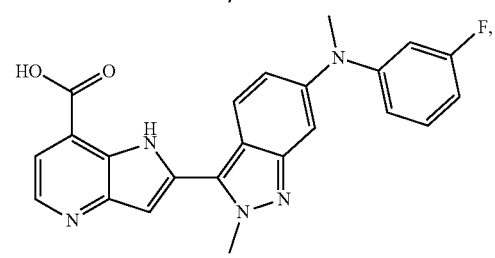
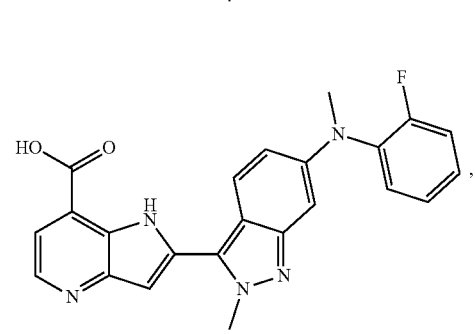
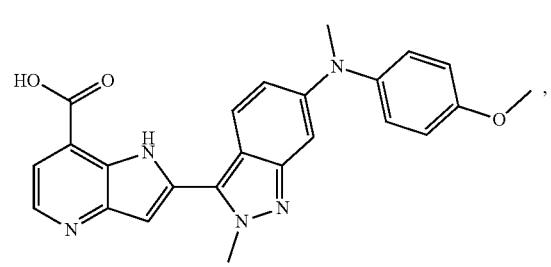
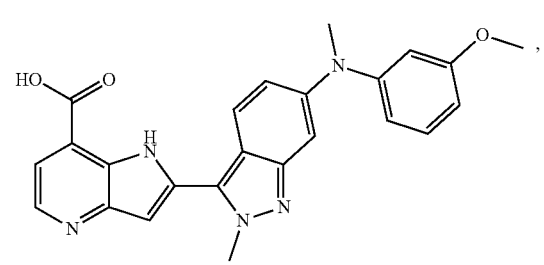
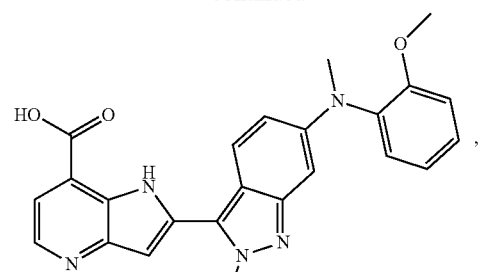
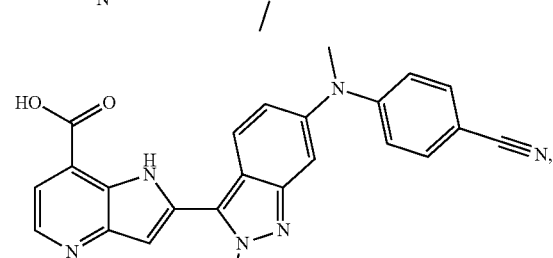
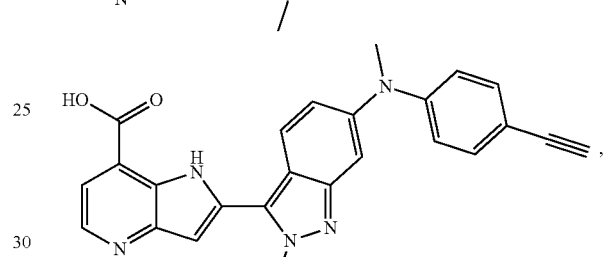
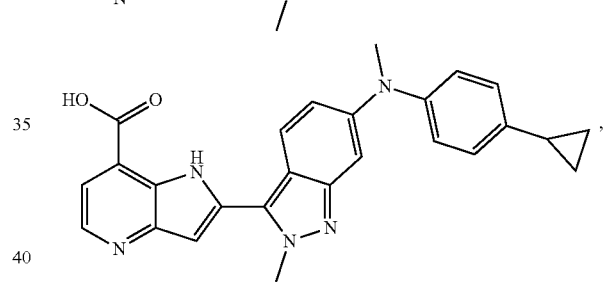
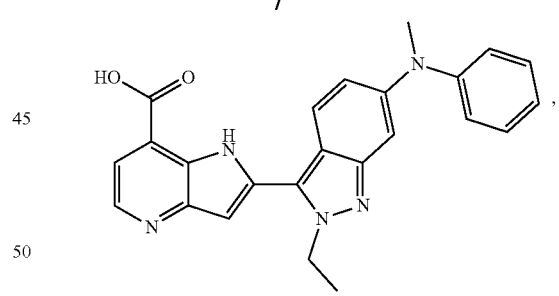
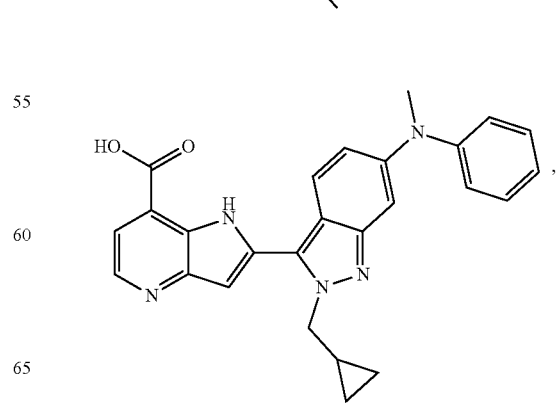

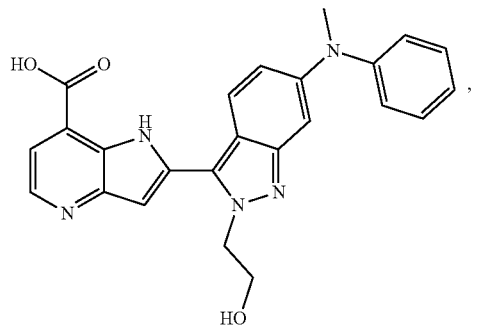
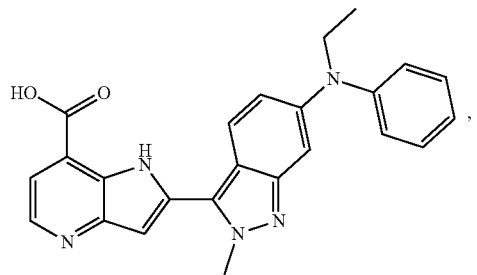
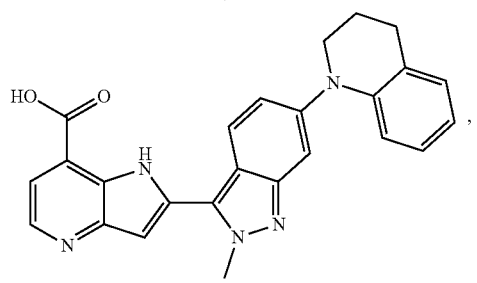
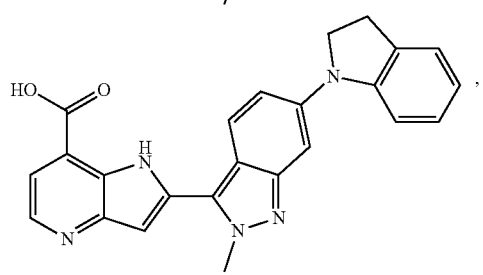
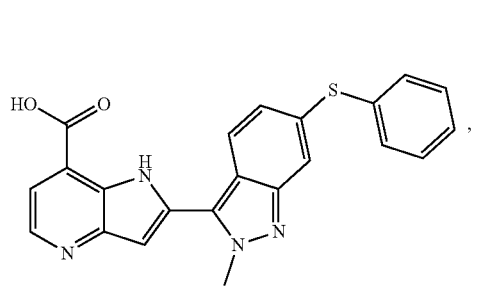
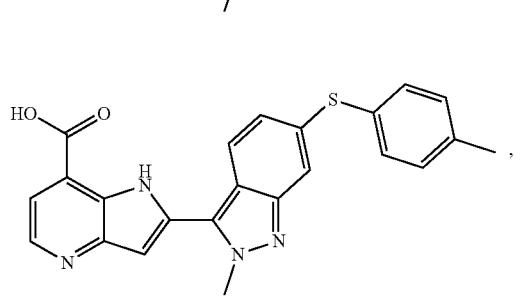
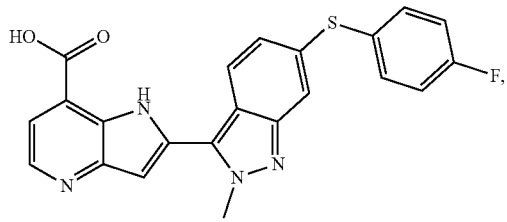
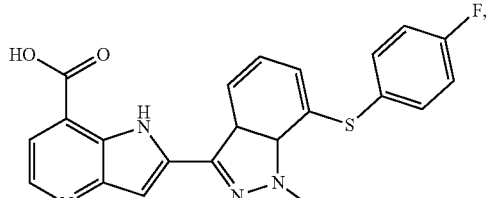
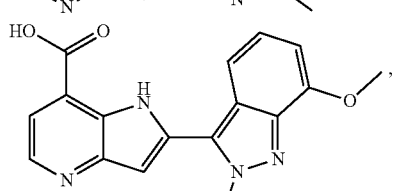
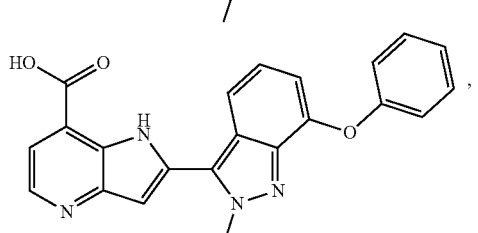
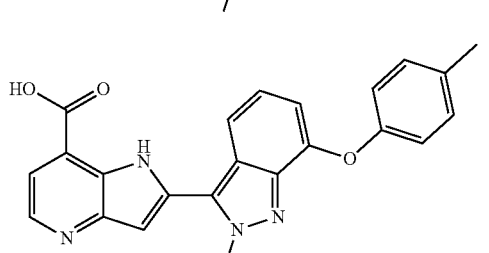
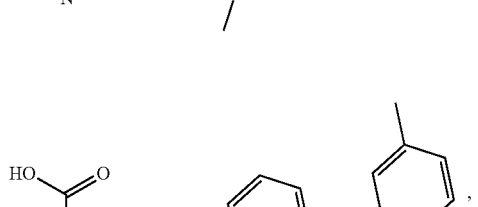
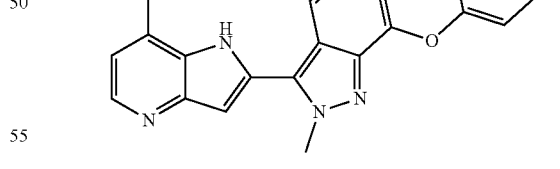
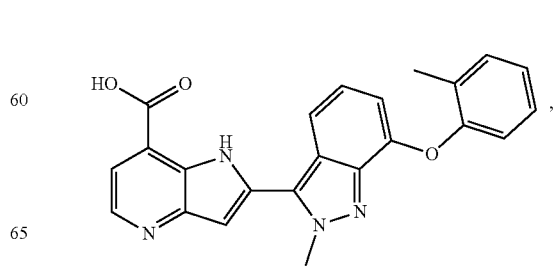

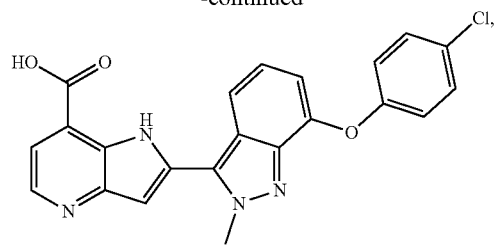
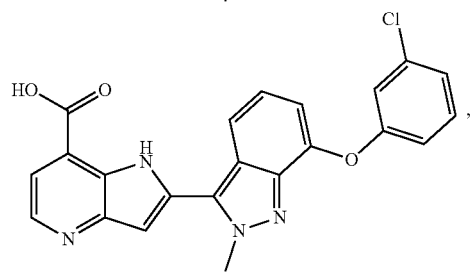
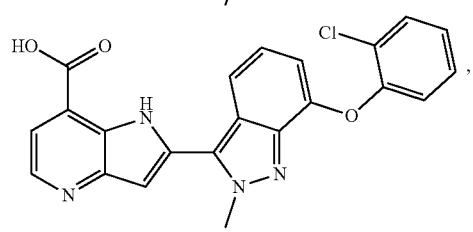
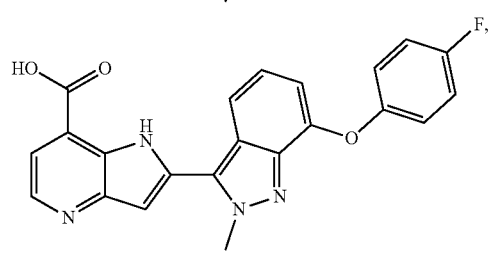
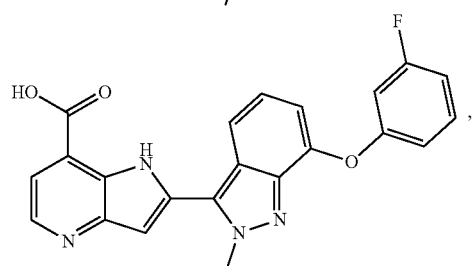
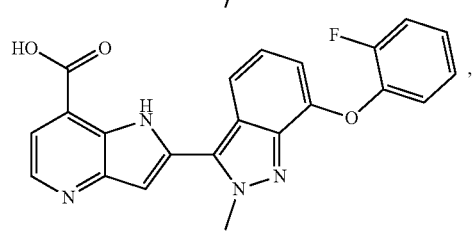
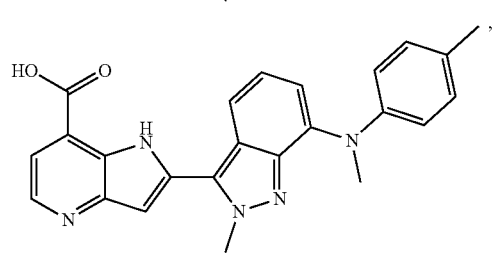
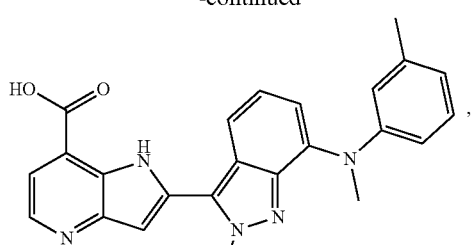
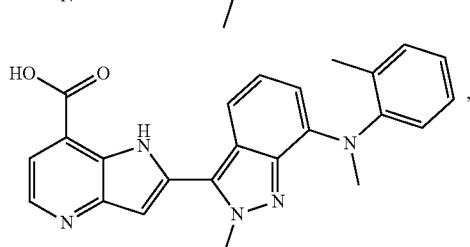
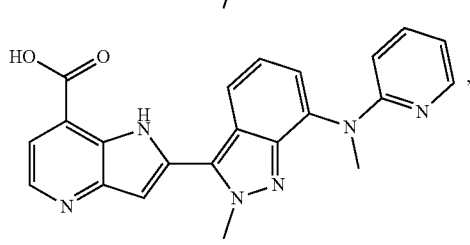
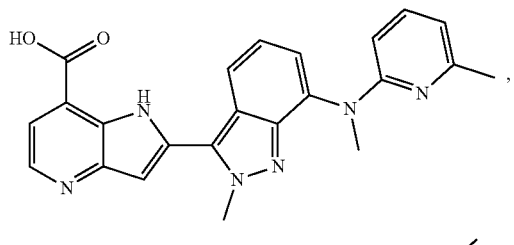
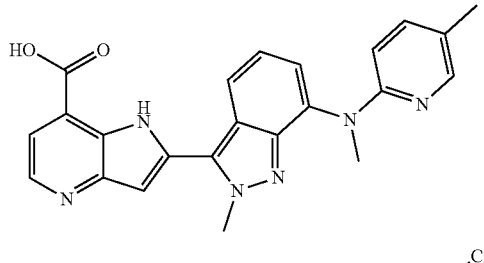
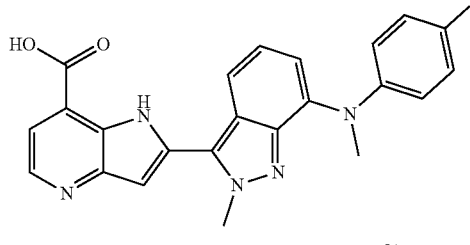
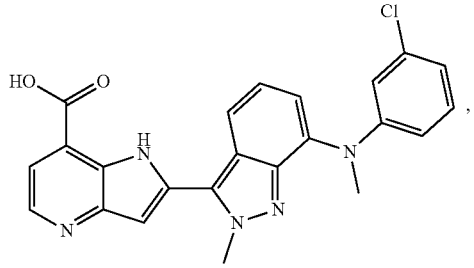

101
-continued
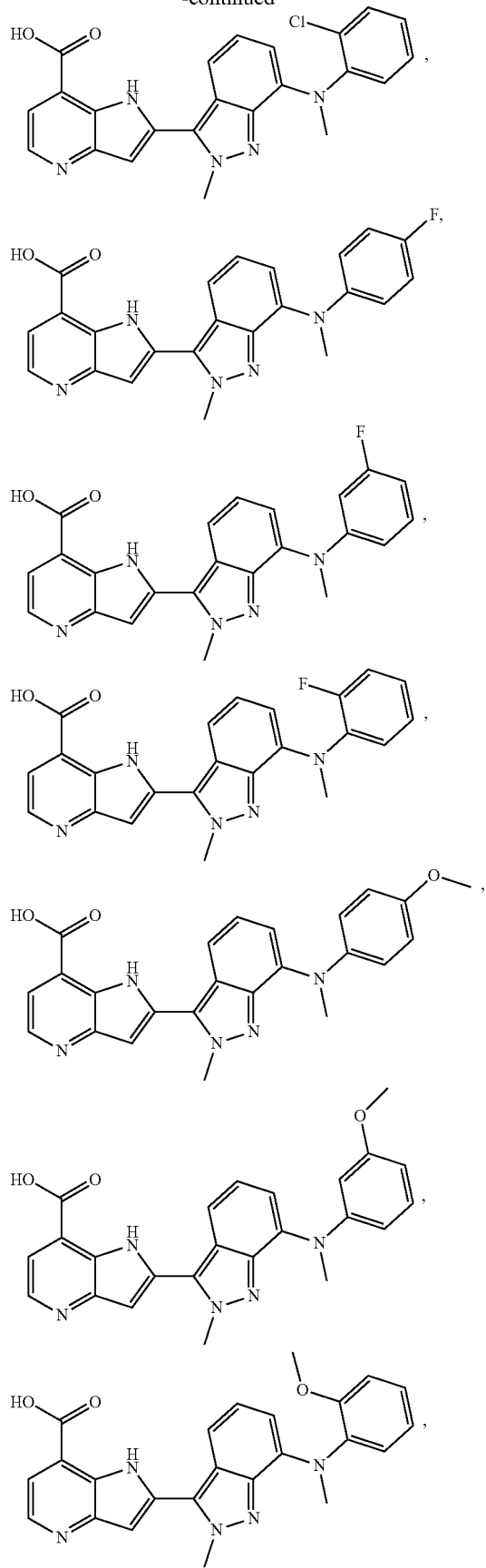
102
-continued
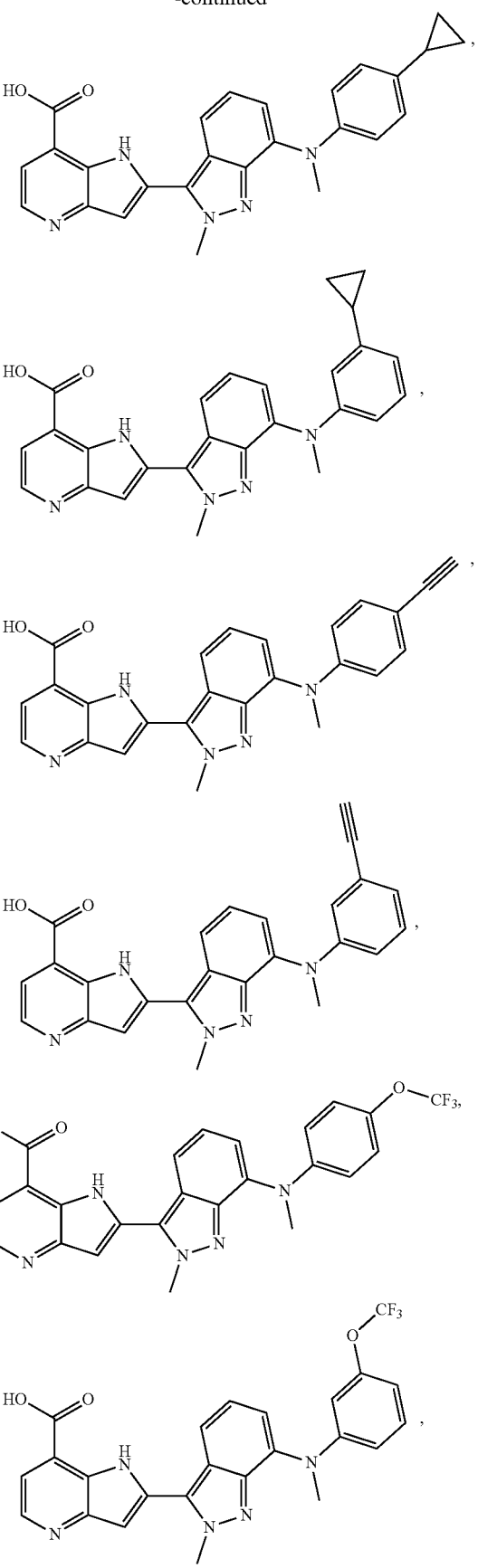

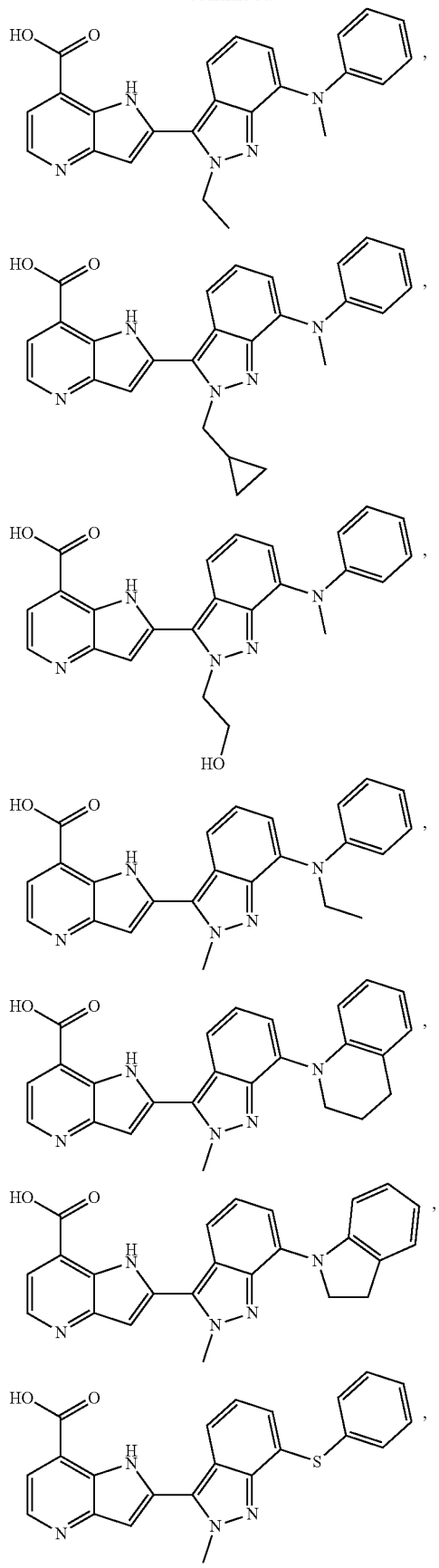
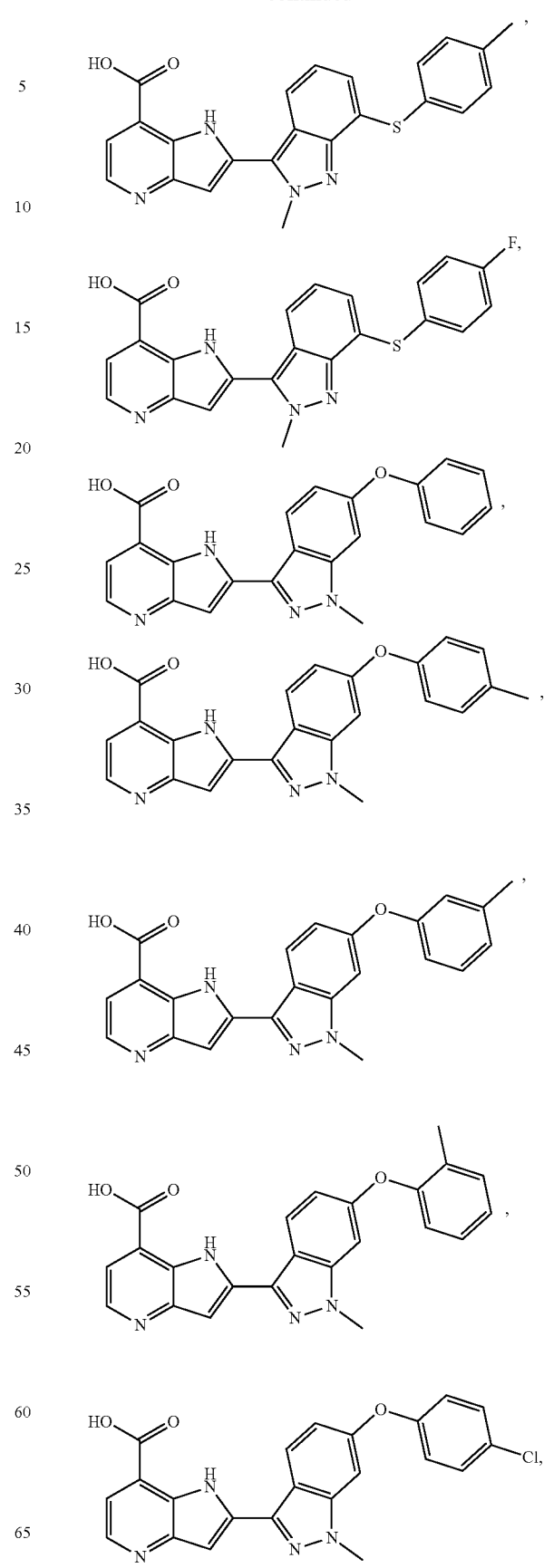

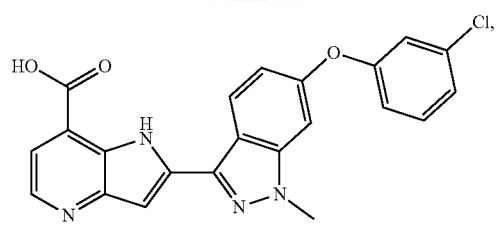
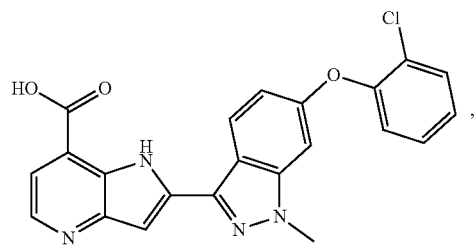
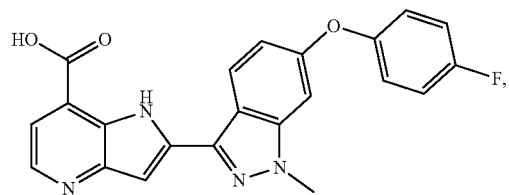
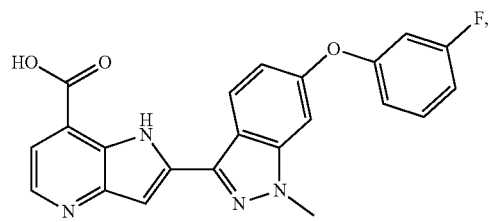
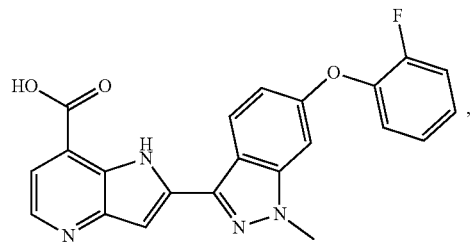
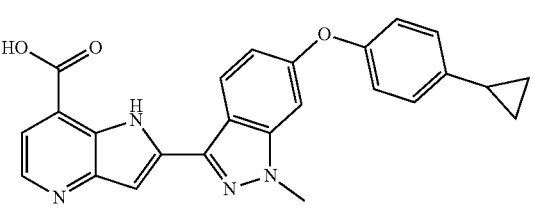
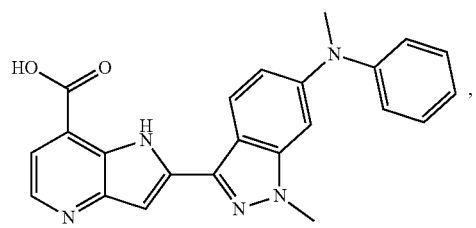
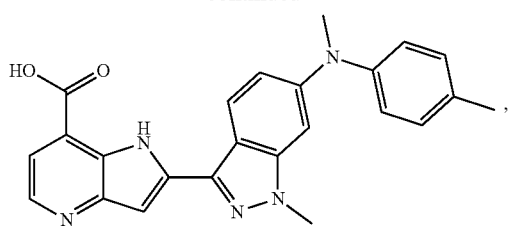
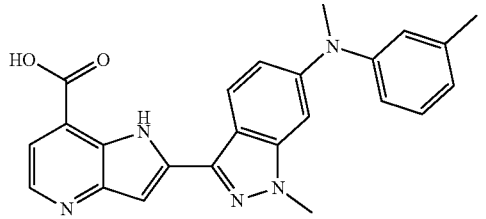
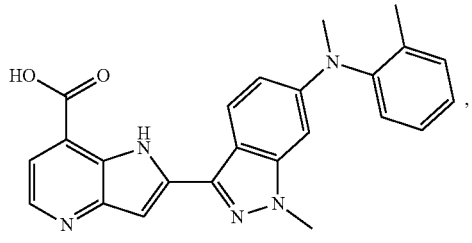
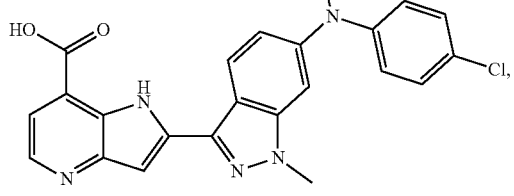
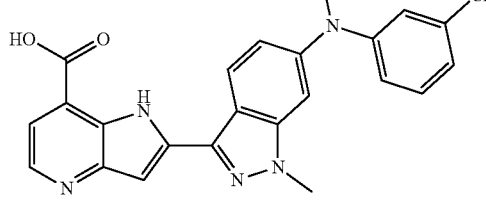
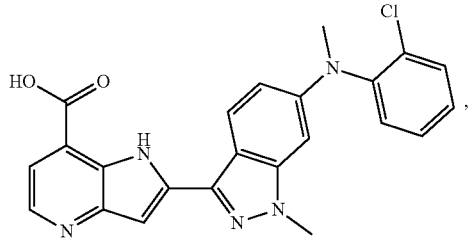
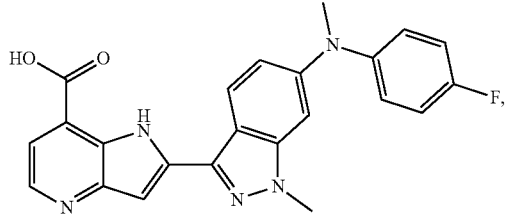

107
-continued
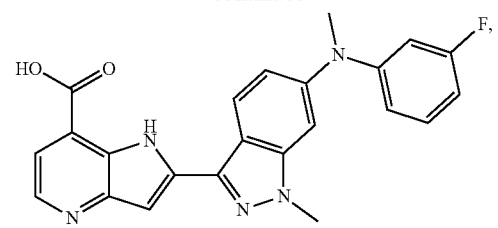
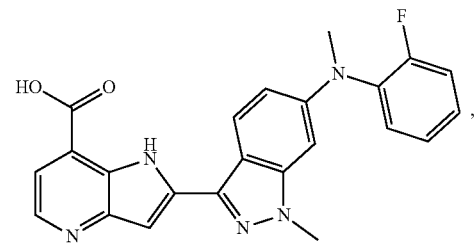
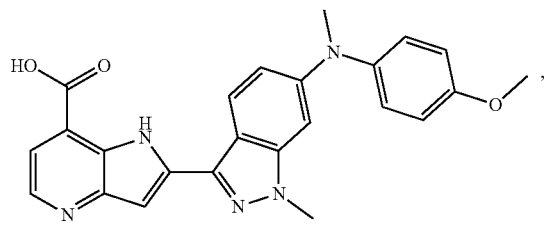
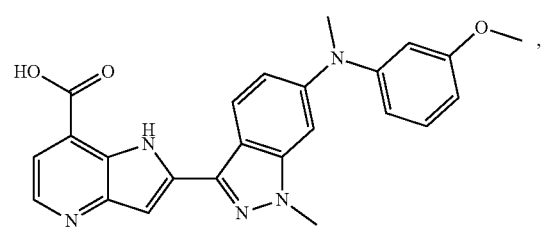
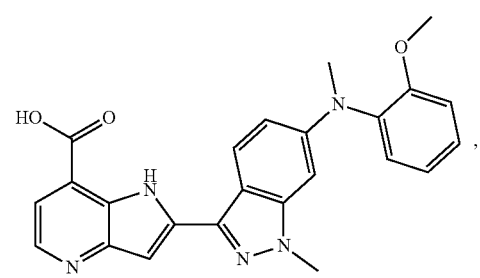
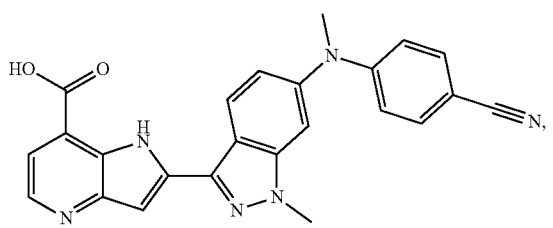
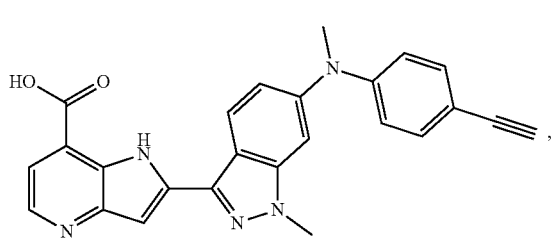
108
-continued
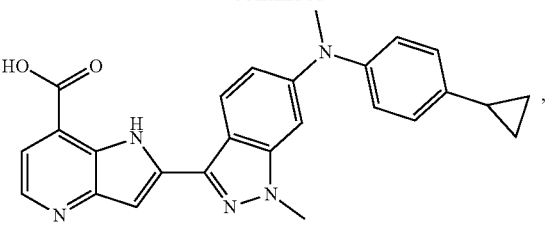
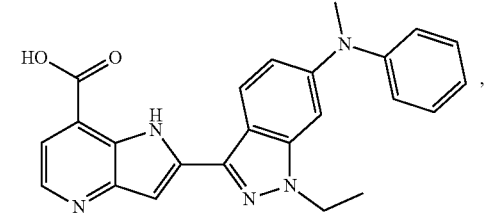
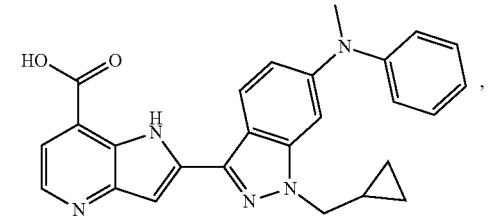
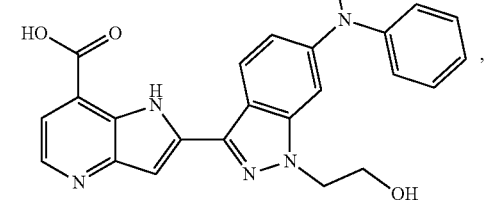
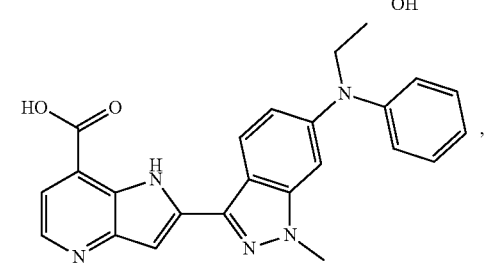
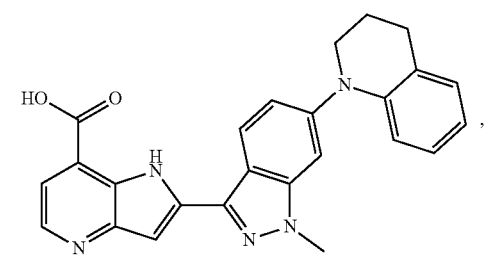
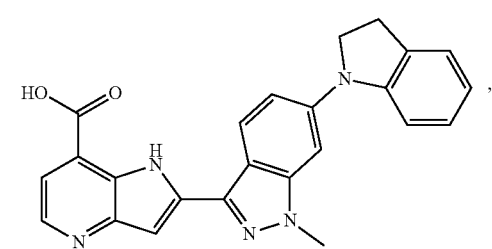

-continued

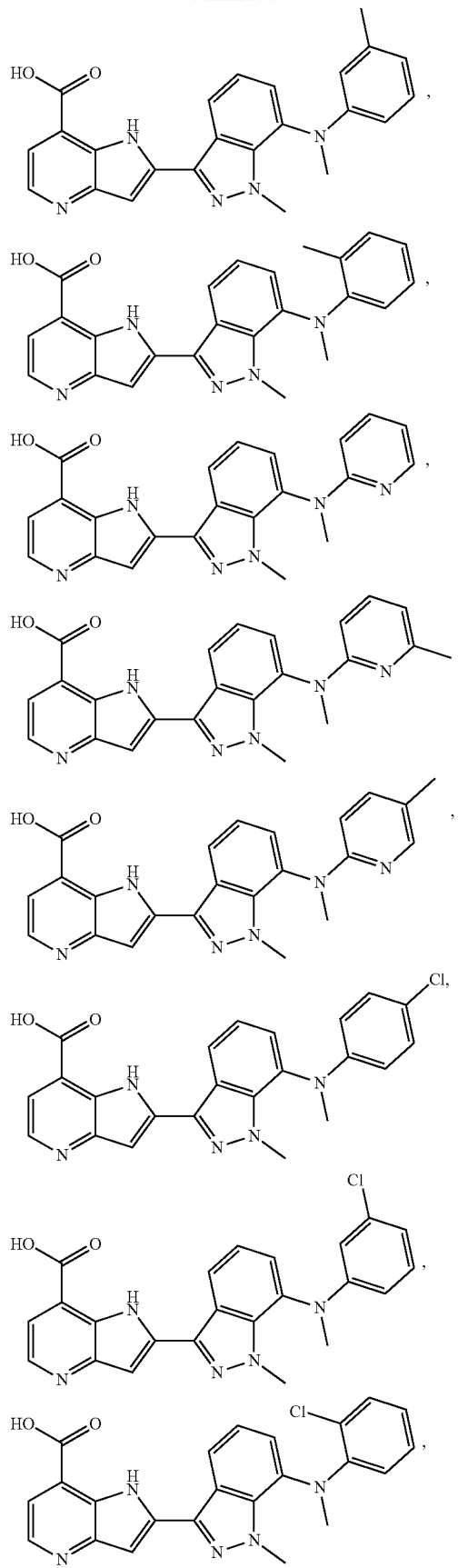
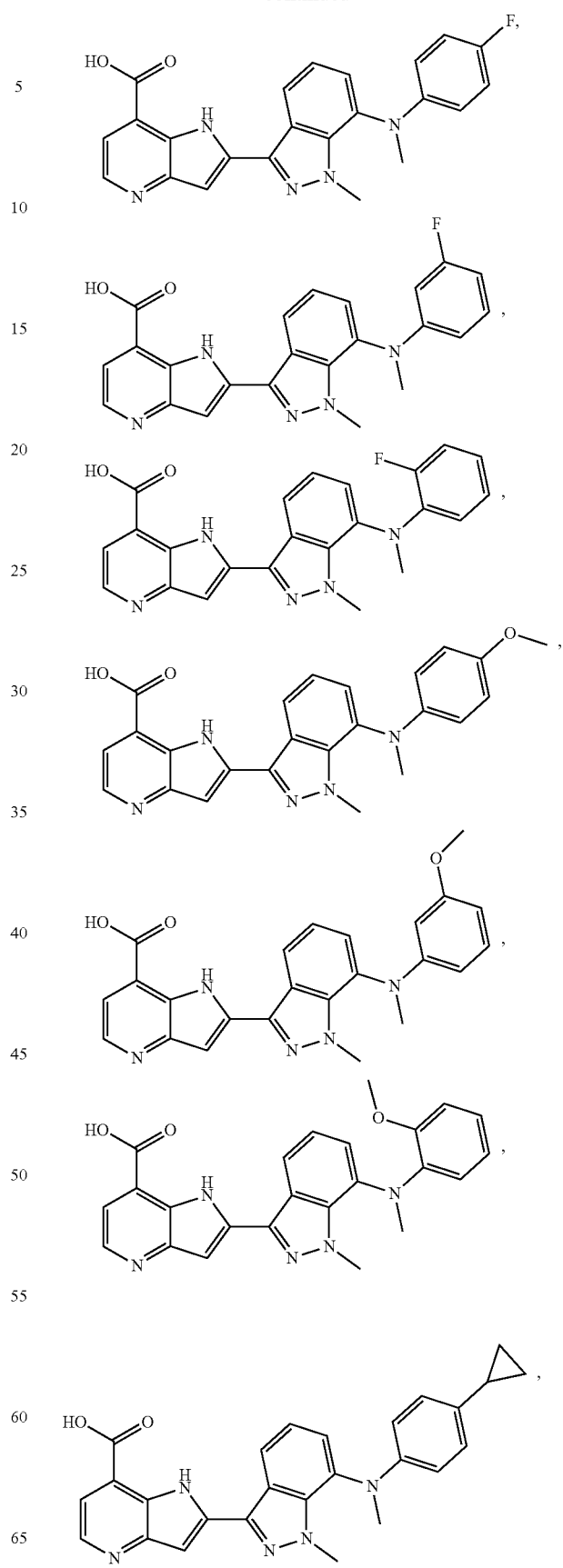

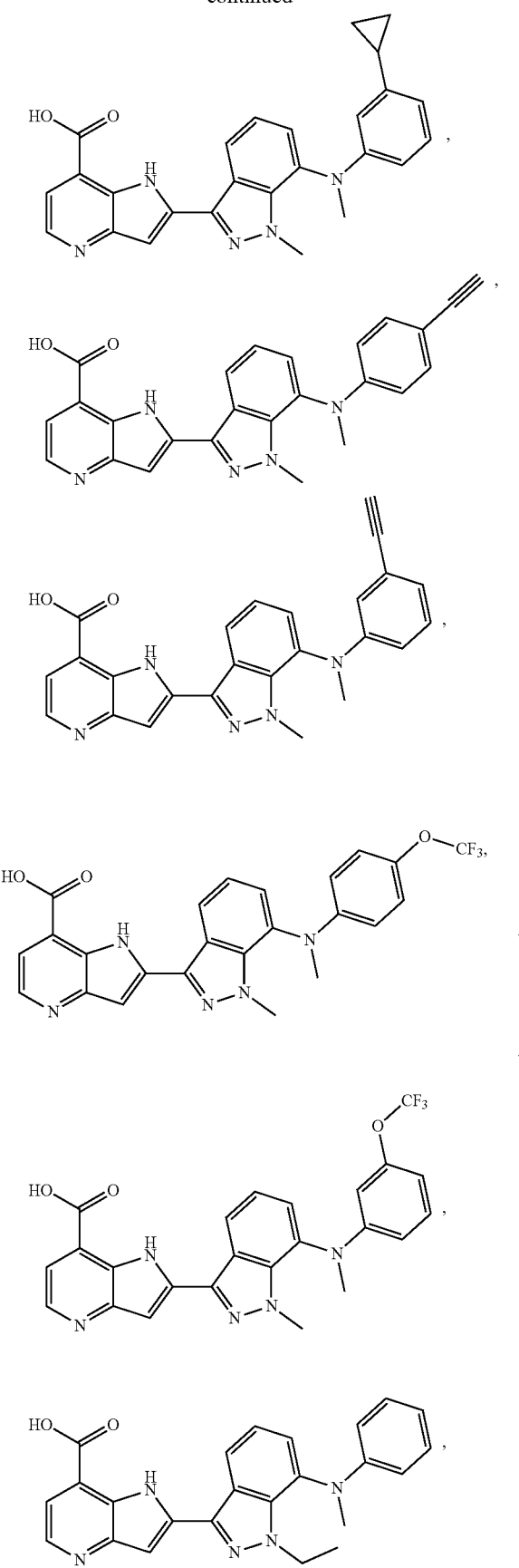
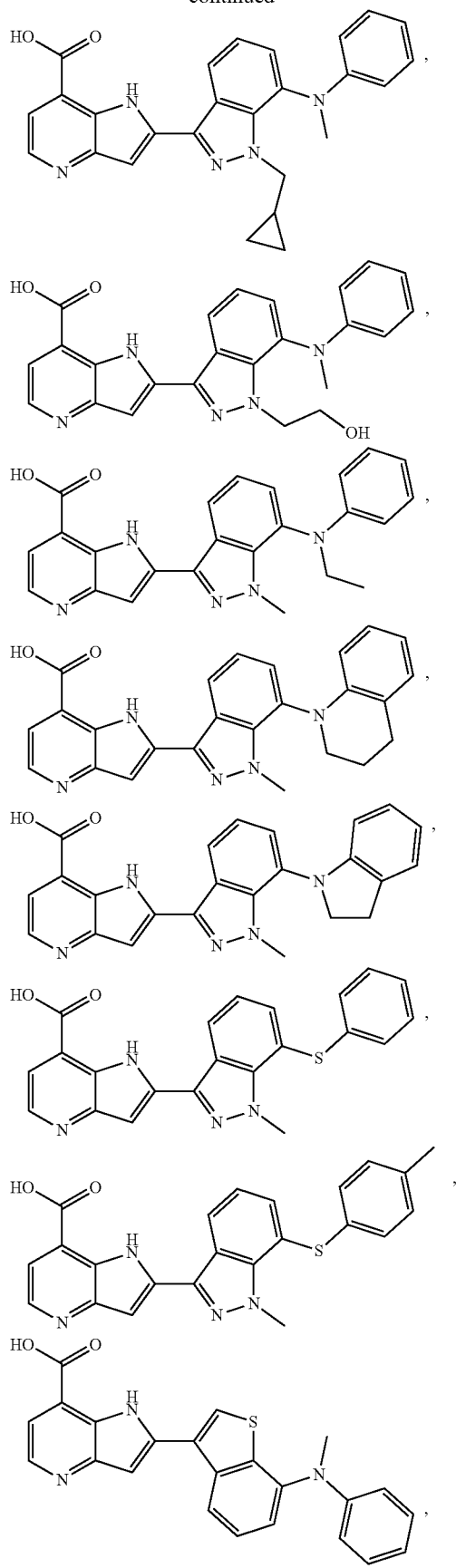

-continued
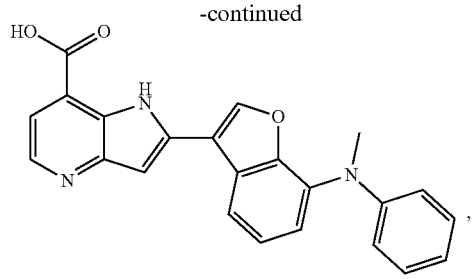
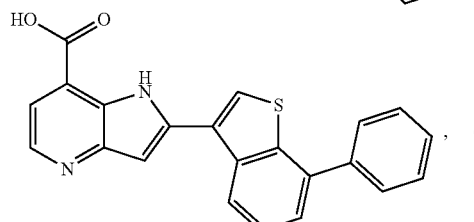, or
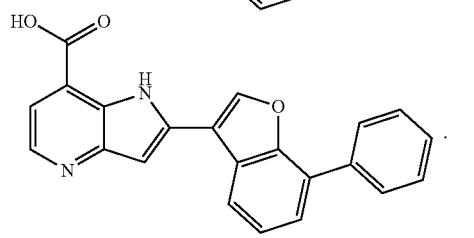.
4. A pharmaceutical composition comprising the compound of claim 3 and at least one pharmaceutically acceptable excipient.
* * * * *